US012797393B2

(12) United States Patent
Chandra et al.

(10) Patent No.: US 12,797,393 B2
(45) Date of Patent: Nov. 17, 2026

(54) METHODS AND COMPOSITIONS FOR TREATING RESISTANT AND RECURRENT FORMS OF CANCER

(71) Applicant: Health Research, Inc., Buffalo, NY (US)

(72) Inventors: Dhyan Chandra, Buffalo, NY (US); Rahul Kumar, Buffalo, NY (US); Neelu Yadav, Buffalo, NY (US)

( * ) Notice: Subject to any disclaimer, the term of this patent is extended or adjusted under 35 U.S.C. 154(b) by 850 days.

(21) Appl. No.: 17/423,959

(22) PCT Filed: Jan. 31, 2020

(86) PCT No.: PCT/US2020/016177
§ 371 (c)(1),
(2) Date: Jul. 19, 2021

(87) PCT Pub. No.: WO2020/160450
PCT Pub. Date: Aug. 6, 2020

(65) Prior Publication Data

US 2022/0088031 A1 Mar. 24, 2022

Related U.S. Application Data

(60) Provisional application No. 62/800,071, filed on Feb. 1, 2019.

(51) Int. Cl.
*A61K 31/555* (2006.01)
*A61K 31/136* (2006.01)
(Continued)

(52) U.S. Cl.
CPC .......... *A61K 31/555* (2013.01); *A61K 31/136* (2013.01); *A61K 31/19* (2013.01);
(Continued)

(58) Field of Classification Search
CPC .... A61K 31/555; A61K 31/136; A61K 31/19; A61K 31/337; A61K 31/426; A61K 31/565; A61P 35/00
See application file for complete search history.

(56) References Cited

U.S. PATENT DOCUMENTS

2003/0087861 A1 5/2003 Iversen
2007/0027169 A1* 2/2007 Mohapatra ............. A61K 45/06 514/263.38

(Continued)

FOREIGN PATENT DOCUMENTS

WO WO-2009094619 A1 * 7/2009 ........... G01N 33/574
WO WO-2010009337 A2 * 1/2010 ......... A01K 67/0276
WO WO-2010/009337 A9 3/2010

OTHER PUBLICATIONS

Domingo-Domenech J, Mellado B, Ferrer B, Truan D, Codony-Servat J, Sauleda S, Alcover J, Campo E, Gascon P, Rovira A, Ross JS, Fernández PL, Albanell J. Activation of nuclear factor-kappaB in human prostate carcinogenesis and association to biochemical relapse. Br J Cancer. Nov. 28, 2005;93(11):1285-94 (Year: 2005).*

(Continued)

*Primary Examiner* — Clinton A Brooks
*Assistant Examiner* — Izabela Schmidt
(74) *Attorney, Agent, or Firm* — Harris Beach Murtha Cullina PLLC; Laura W. Smalley

(57) ABSTRACT

A method for treating prostate cancer in a subject involves selecting a subject having prostate cancer and cytochrome c-deficiency, and administering, to the selected subject, a therapeutically effective amount of one or more agents capable of restoring cytochrome-c activity. Also presented is a method of inducing apoptosis in drug resistant cancer cells involving selecting drug resistant cancer cells having cytochrome-c deficiency, and administering to the selected cells, one or more agents that restore cytochrome-c activity (Continued)

Figure 1A:
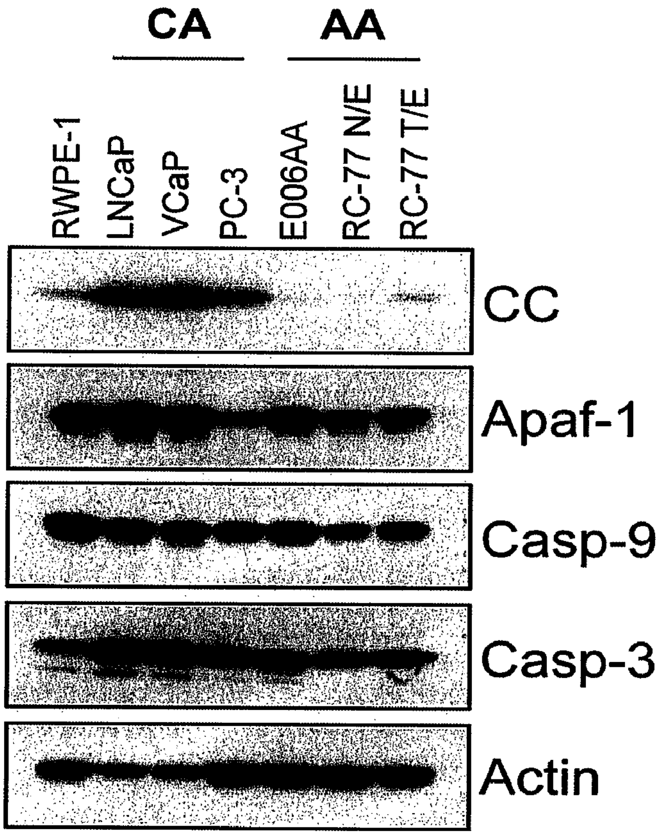

in an amount effective to sensitize said cancer cells to drug induced apoptosis. A combination therapeutic comprising one or more agents increases cytochrome-c activity and efficacy of a chemotherapeutic agent. Another method involves selecting a subject having cancer, and obtaining a cell sample including tumor tissues/biopsy and blood samples from said subject, and further involves measuring cytochrome-c expression levels and Drp1 phosphorylation levels in said sample.

20 Claims, 32 Drawing Sheets

Specification includes a Sequence Listing.

(51) Int. Cl.

| | |
|---|---|
| ***A61K 31/19*** | (2006.01) |
| ***A61K 31/337*** | (2006.01) |
| ***A61K 31/426*** | (2006.01) |
| ***A61K 31/565*** | (2006.01) |
| ***A61K 31/655*** | (2006.01) |
| ***A61P 35/00*** | (2006.01) |

(52) U.S. Cl.

CPC .......... *A61K 31/337* (2013.01); *A61K 31/426* (2013.01); *A61K 31/565* (2013.01); *A61P 35/00* (2018.01)

(56) References Cited

U.S. PATENT DOCUMENTS

| | | | | |
|---|---|---|---|---|
| 2007/0105751 | A1* | 5/2007 | Baldwin | A61K 31/4745 514/19.5 |
| 2007/0203098 | A1 | 8/2007 | Garlich et al. | |
| 2010/0010078 | A1* | 1/2010 | Mukhtar | A61P 35/00 514/456 |
| 2011/0206689 | A1* | 8/2011 | Hahn | C12Y 207/10002 204/450 |

OTHER PUBLICATIONS

Lavinia A. Carabet et al., European Journal of Medicinal Chemistry 160 (2018) 108-119 (Year: 2018).*

Kavathia, Nilay; Jain, Alka; Walston, Jeremy; Beamer, Brock A.; Fedarko, Neal S. Aging (2009), 1(7), 652-663 (Year: 2009).*

Sheng, S.L., Liu, J.J., Dai, Y.H., Sun, X.G., Xiong, X.P. and Huang, G. (2012), Knockdown of lactate dehydrogenase A suppresses tumor growth and metastasis of human hepatocellular carcinoma. FEBS J, 279: 3898-3910 (Year: 2012).*

Nakano A, Tsuji D, Miki H, Cui Q, Sayed SME, et al. (2011) Glycolysis Inhibition Inactivates ABC Transporters to Restore Drug Sensitivity in Malignant Cells. PLOS ONE 6(11): e27222. https://doi.org/10.1371/journal.pone.0027222 (Year: 2011).*

Xin, Li, et al. "Progression of Prostate Cancer by Synergy of AKT with Genotropic and Nongenotropic Actions of the Androgen Receptor." Proceedings of the National Academy of Sciences of the United States of America, vol. 103, No. 20, 2006, pp. 7789-7794 (Year: 2006).*

AACR Annual Meeting—Apr. 18-22, 2009, Denver, CO—made of record on the IDS (Year: 2009).*

Barfeld SJ, Urbanucci A, Itkonen HM, Fazli L, Hicks JL, Thiede B, Rennie PS, Yegnasubramanian S, DeMarzo AM, Mills IG. c-Myc Antagonises the Transcriptional Activity of the Androgen Receptor in Prostate Cancer Affecting Key Gene Networks. EBioMedicine. Apr. 2017; 18:83-93 (Year: 2017).*

Kim et al., Anticancer Research 36: 6109-6116 (2016), doi:10.21873/anticanres.11201 (Year: 2016).*

Liu et al. Cell, vol. 86, 147-157, Jul. 12, 1996 (Year: 1996).*

Kalpage et al., FASEB J. Feb. 2019;33(2):1540-1553. doi: 10.1096/fj.201801417R (Year: 2019).*

Andrea Renz, Wolfgang E. Berdel, Michael Kreuter, Claus Belka, Klaus Schulze-Osthoff, Marek Los, Rapid extracellular release of cytochrome c is specific for apoptosis and marks cell death in vivo, Blood, vol. 98, Issue 5, 2001, pp. 1542-1548, ISSN 0006-4971 (Year: 2001).*

Mukhtar et al., Mol Cancer Ther. Dec. 2016; 15(12): 2863-2874. doi:10.1158/1535-7163.MCT-16-0515) evidenced by Abidi (Abidi A. Cabazitaxel: A novel taxane for metastatic castration-resistant prostate cancer-current implications and future prospects. J Pharmacol Pharmacother. Oct. 2013;4(4):230-7. (Year: 2013).*

Abidi A. Cabazitaxel: A novel taxane for metastatic castration-resistant prostate cancer-current implications and future prospects. J Pharmacol Pharmacother. Oct. 2013;4(4):230-7. doi: 10.4103/0976-500X. 119704. PMID: 24250198 (Year: 2013).*

Antonio Galina, Mitochondria: 3-bromopyruvate vs. mitochondria? A small molecule that attacks tumors by targeting their bioenergetic diversity, The International Journal of Biochemistry & Cell Biology, vol. 54, 2014, pp. 266-271 (Year: 2014).*

Barfeld et al.,EBioMedicine. Apr. 2017;18:83-93. doi: 10.1016/j.ebiom.2017.04.006. Epub Apr. 5, 2017. (Year: 2017).*

Xian et al., Tumor Biol. (2015) 36:8093-8100 (Year: 2015).*

Chu-Chiao Wu and Shawn B. Bratton, Antioxidants & Redox Signaling, vol. 19, No. 6, 2013 (Year: 2013).*

Https://en.wikipedia.org/wiki/Taxane , printed Jun. 12, 2025. (Year: 2025).*

D.I. Quinn, H.M. Sandler, L.G. Horvath, A. Goldkorn, J.A. Eastham, The evolution of chemotherapy for the treatment of prostate cancer, Annals of Oncology, vol. 28, Issue 11, 2017, pp. 2658-2669. (Year: 2017).*

PCT International Search Report and Written Opinion of the International Searching Authority for corresponding International Application No. PCT/US20/016177 with a date of mailing of Jul. 6, 2020.

Kavathia, N., et al., "Serum markers of apoptosis decrease with age and cancer stage", Aging, Jul. 14, 2009, vol. 1, No. 7, (pp. 652-663).

Lee, S., et al., "Alpha-Tomatine Induces Apoptosis and Inhibits Nuclear Factor-Kappa B Activation on Human Prostatic Adenocarcinoma PC-3 Cells." PLoS One, Apr. 26, 2011, vol. 6, Issue 4, (pp. 1-14).

Sheng, S., et al., "Knockdown of lactate dehydrogenase A suppresses tumor growth and metastasis of human hepatocellular carcinoma." The FEBS Journal, 2012, vol. 279, (pp. 3898-3910).

Nakano, A., et al., "Glycolysis Inhibition Inactivates ABC Transporters to Restore Drug Sensitivity in Malignant Cells." PLoS One, Nov. 2, 2011, vol. 6, Issue 11, (pp. 1-10).

Bernard, D., et al., "Myc confers androgen-independent prostate cancer cell growth". The Journal of Clinical Investigation. Dec. 2003, vol. 112 (pp. 1724-1731).

Choudhary, V., et al., "Dynamin-related protein (Drp1) is regulated by androgens in prostate cancer LNCaP cells", Abstract #5294, Cancer Research, May 2009, vol. 69, Supp. 9 (4 pages).

Kumar, R., et al. "Cytochrome c Deficiency Confers Apoptosome and Mitrochondrial Dysfunction in African-American Men with Prostate Cancer." Metabolism and Chemical Biology, Feb. 14, 2019, (pp. 1353-1368).

D3: Sharmila Shankar et al. "Molecular mechanisms of resveratrol (3,4,5-trihydroxy-trans-stilbene) and its interaction with TNF-related apoptosis inducing ligand (TRAIL) in androgen-insensitive prostate cancer cells." Mol Cell Biochem (2007) 304:273-285, Published on-Line Jul. 17, 2007. © Springer Science+Business Media B.V. 2007.

D5: Rahul Kumar et al. "Cytochrome c Deficiency Confers Apoptosome and Mitochondrial Dysfunction in African-American Men with Prostate Cancer." Metabolism and Chemical Biology, Downloaded from cancerres.aacrjoumais.org <http://cancerres.aacrjoumais.org> on Aug. 31, 2020. 2019 American Association for Cancer Research; Published OnlineFirst Feb. 14, 2019; DOI: 10.1158/0008-5472.CAN-18-2383.

(56) References Cited

OTHER PUBLICATIONS

D6: Jonathan P. Carson et al. (*Departments of Microbiology If. P. C., M. B., M. J. W., G. K../ and Chemistry U. N. S., D. F. H.) at the University of Virginia, Charlottesville, Virginia 22908, and Howard Hughes Medical institute, Department of Biochemistry. University of Texas Southwestern Medical Center, Dallas, Texas 75235* [*C. D., X. W.*] "Smac is Required for Cytochrome c-induced Apoptosis in Prostate Cancer I,NCaP Cells 1." *Advances in Brief*: [Cancer Research 62, 18-23, Jan. 1, 2002).

D8: Supplementary European Search Report and the European Search Opinion, dated Jan. 25, 2023. (13 pages).

* cited by examiner

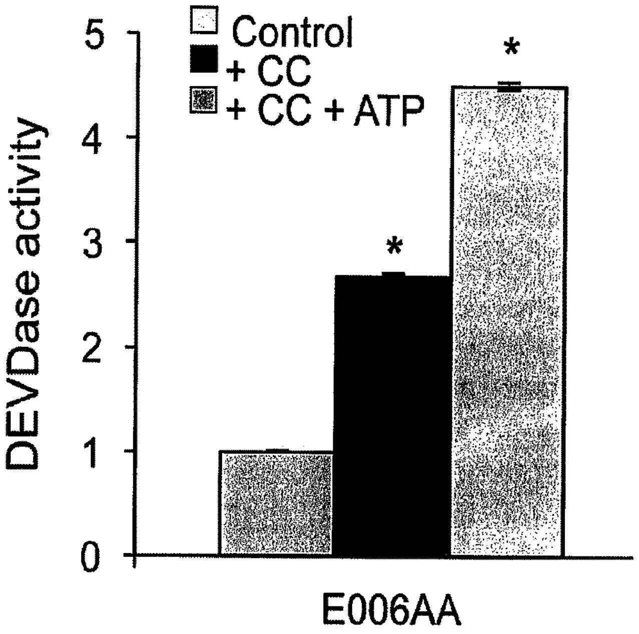
FIG. 2A
FIG. 2B
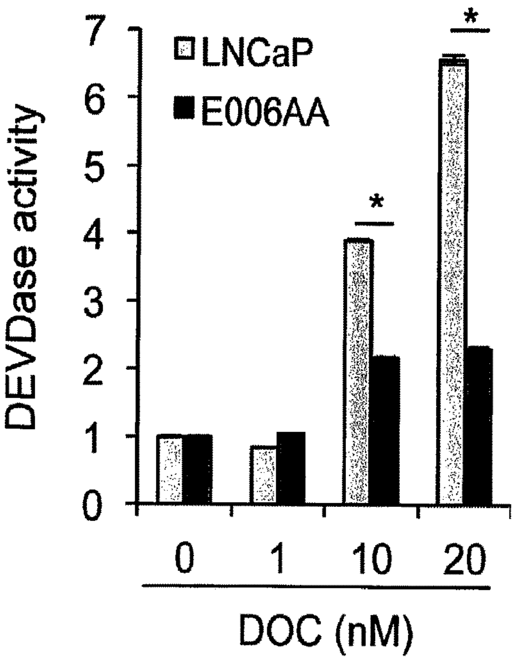
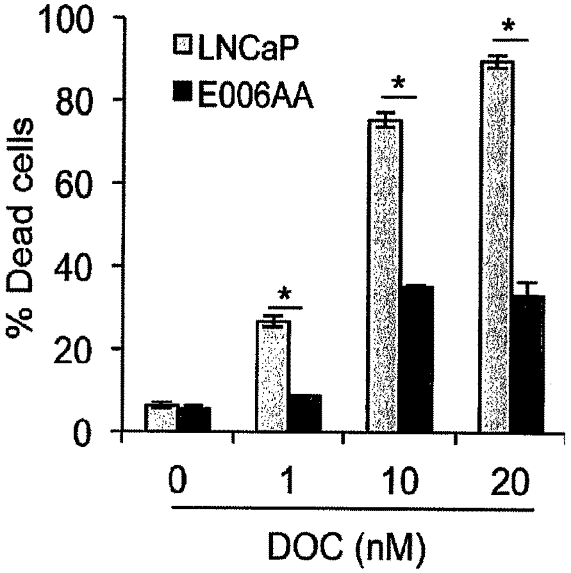
FIG. 2C

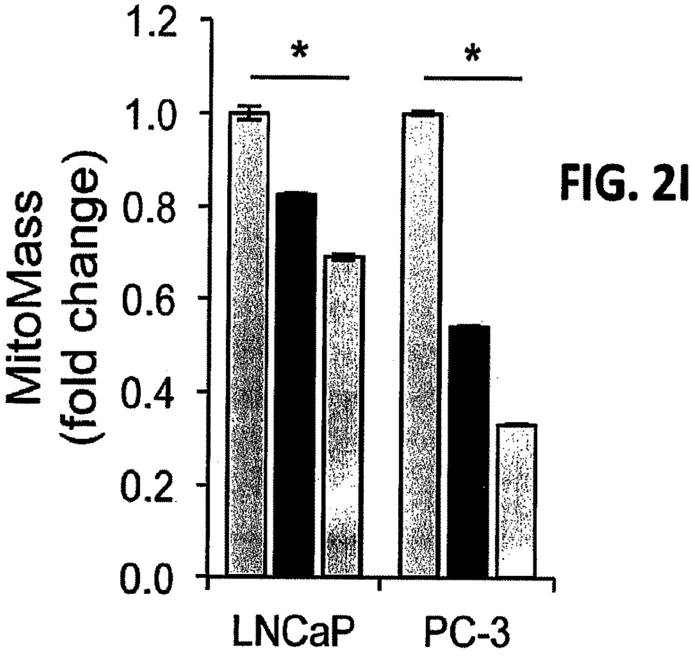
FIG. 2I
FIG. 2J
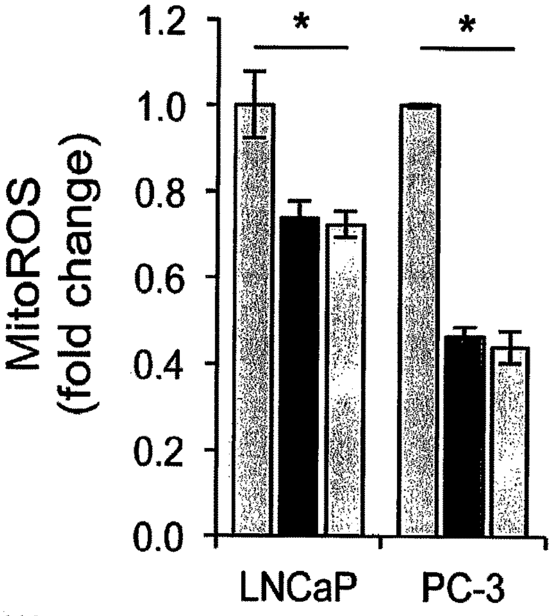
FIG. 2K
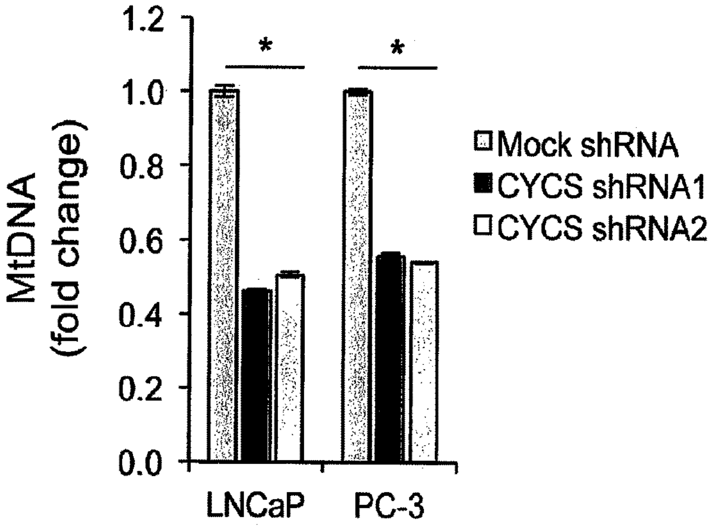

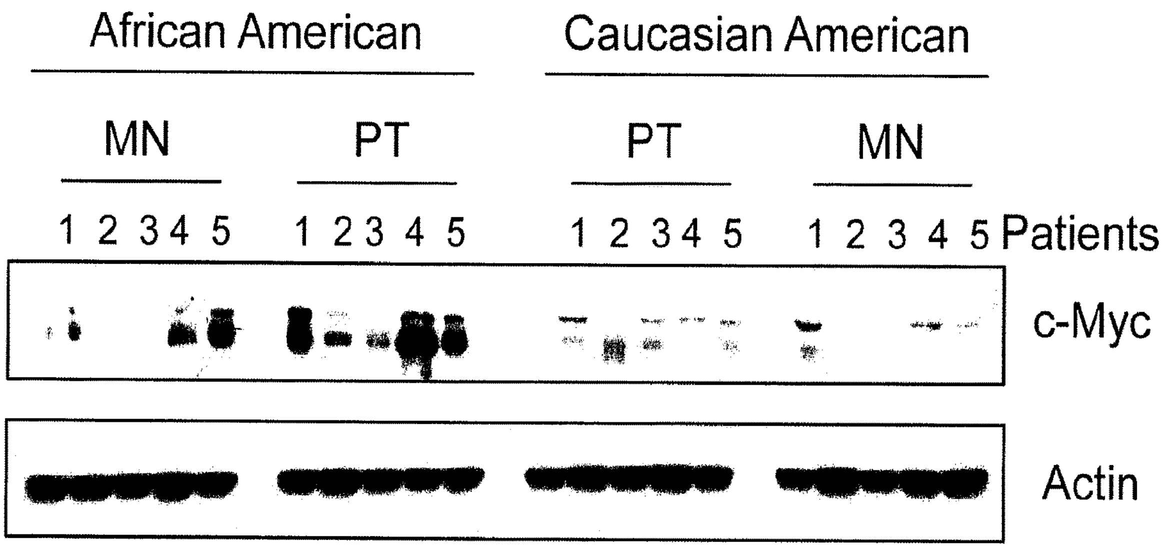
FIG. 3E
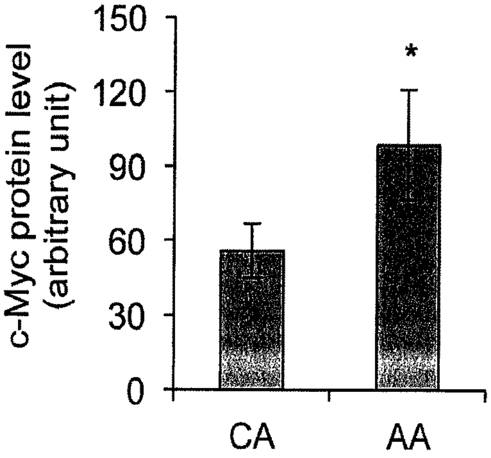
FIG. 3F
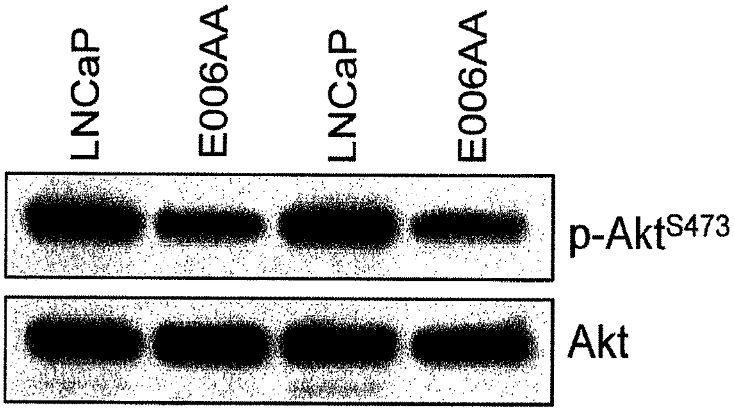

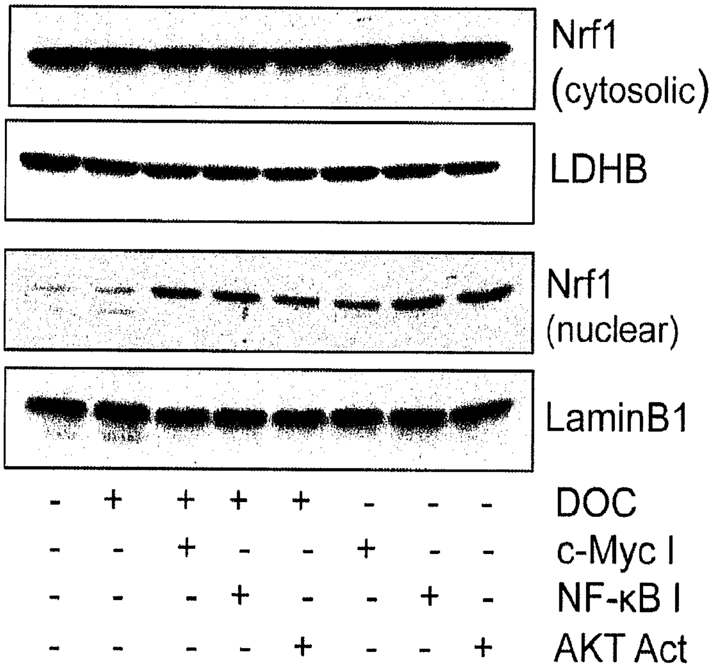
FIG. 4E
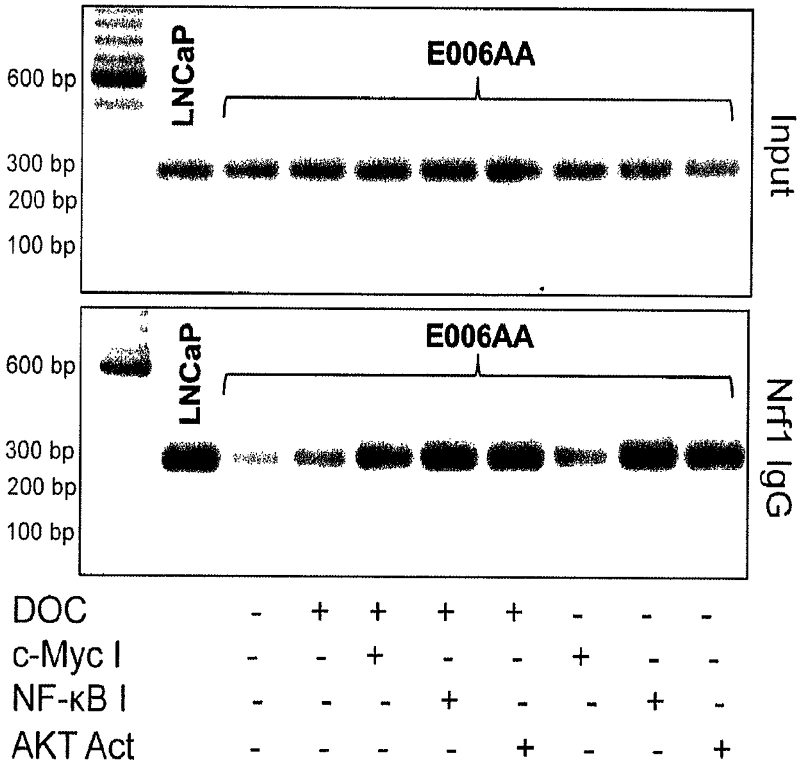

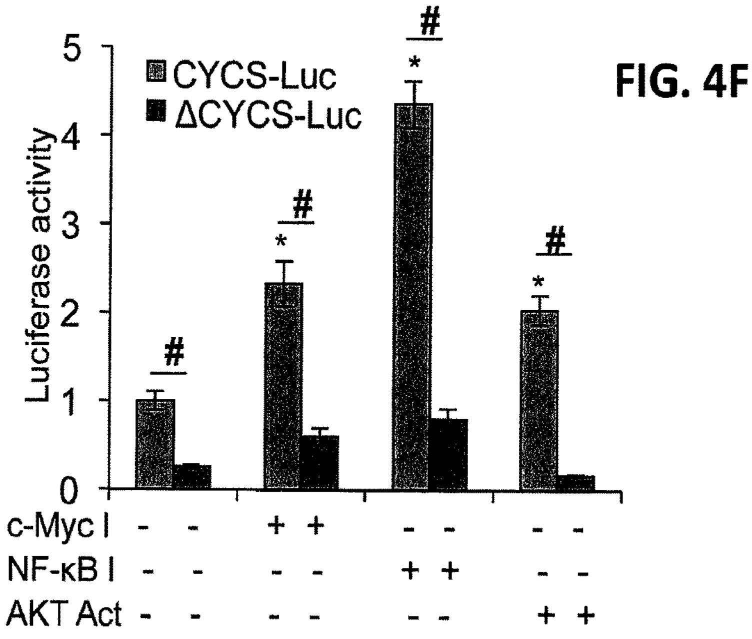
FIG. 4F
FIG. 4G
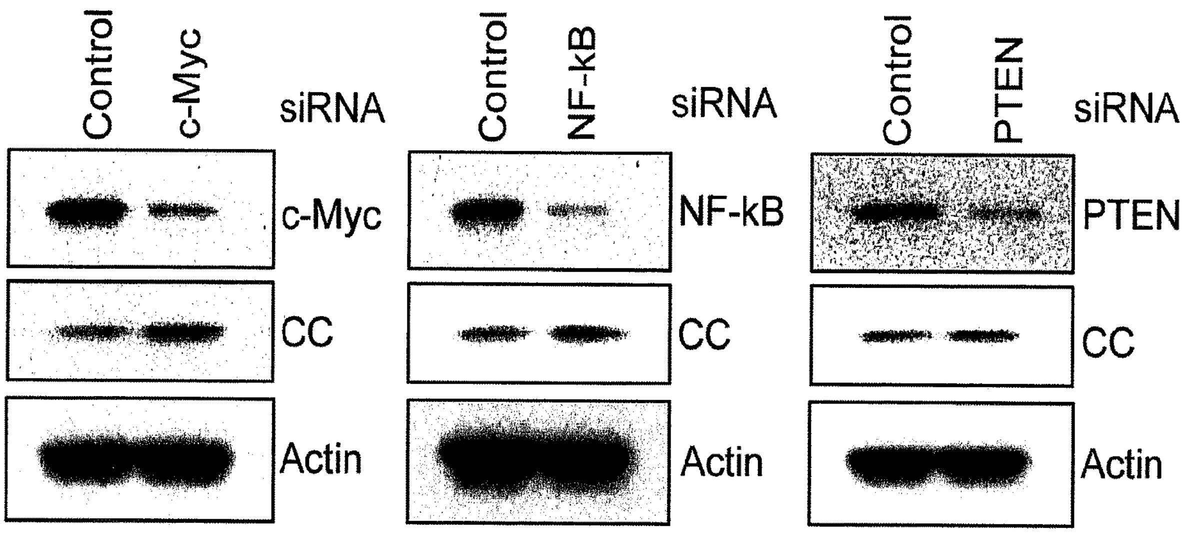

FIG. 5E
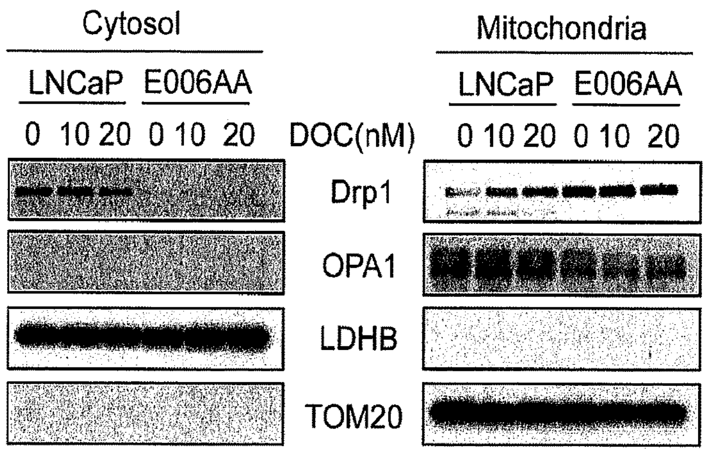
FIG. 5F
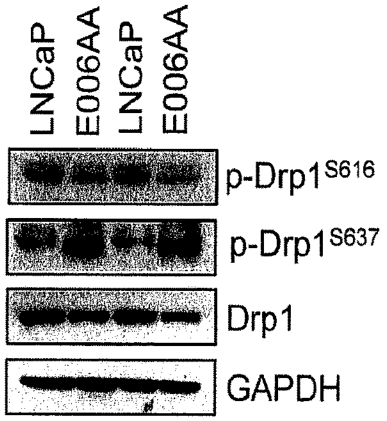
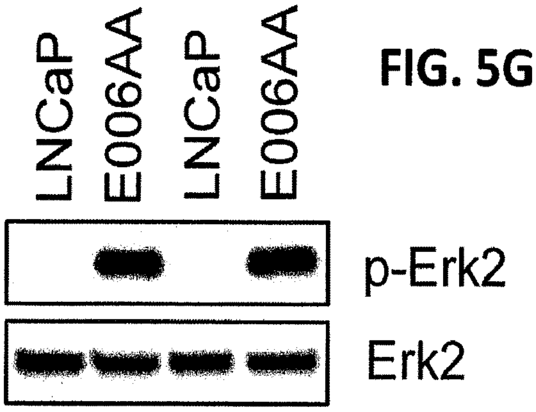
FIG. 5G
FIG. 5H
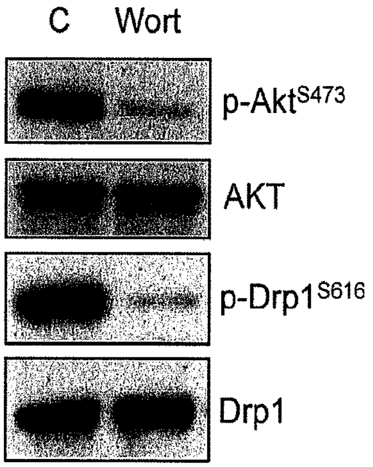

FIG. 6A
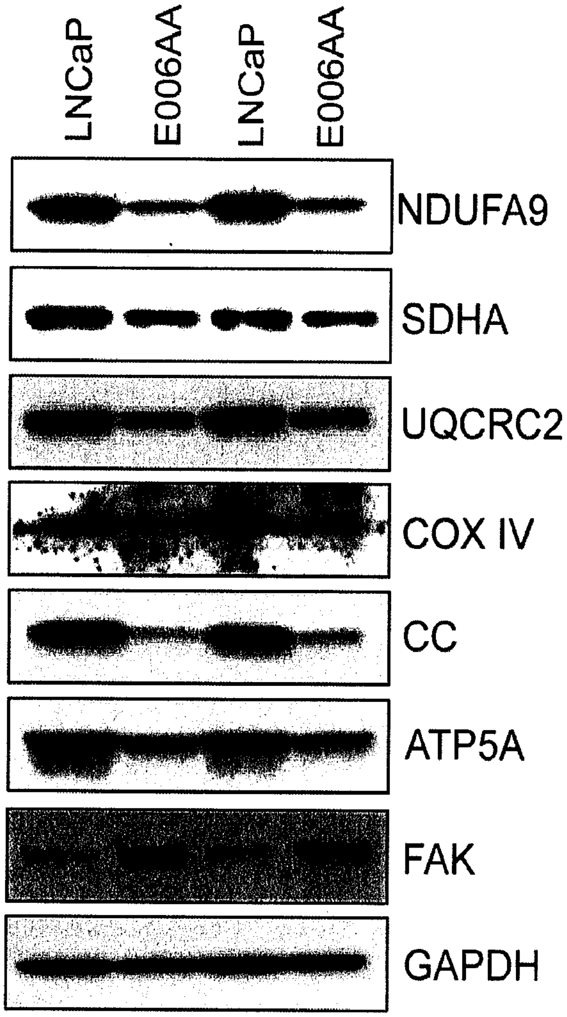
FIG. 6B
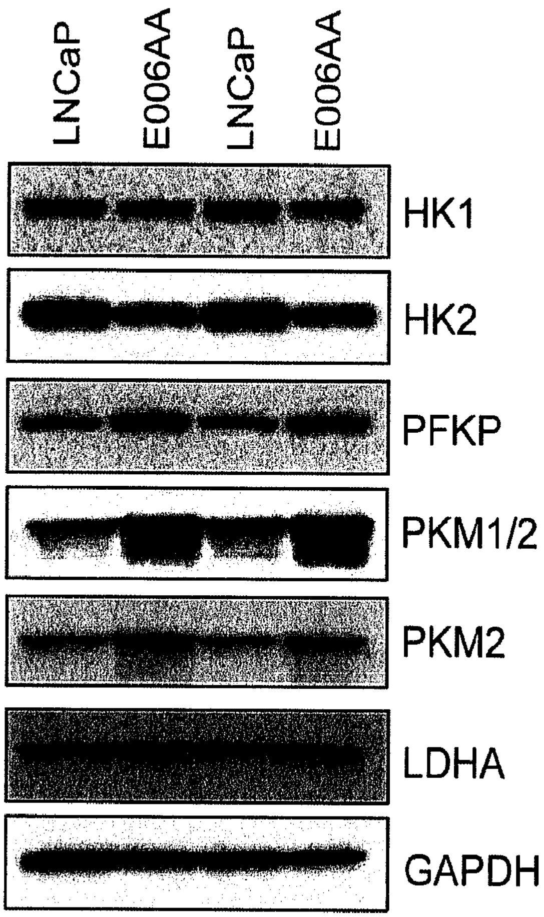
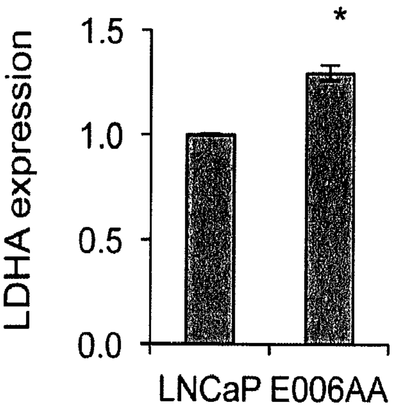
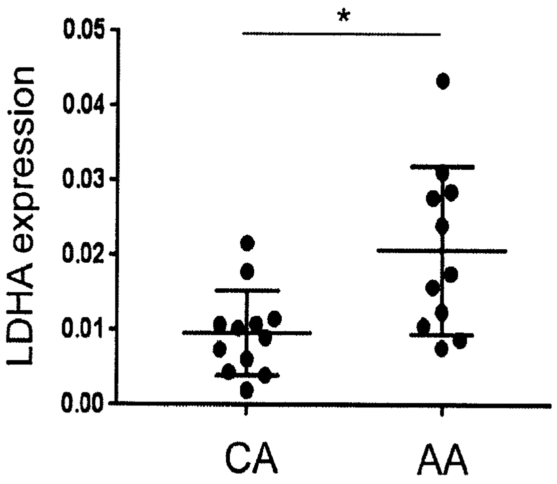
FIG. 6C
FIG. 6D

FIG. 9A
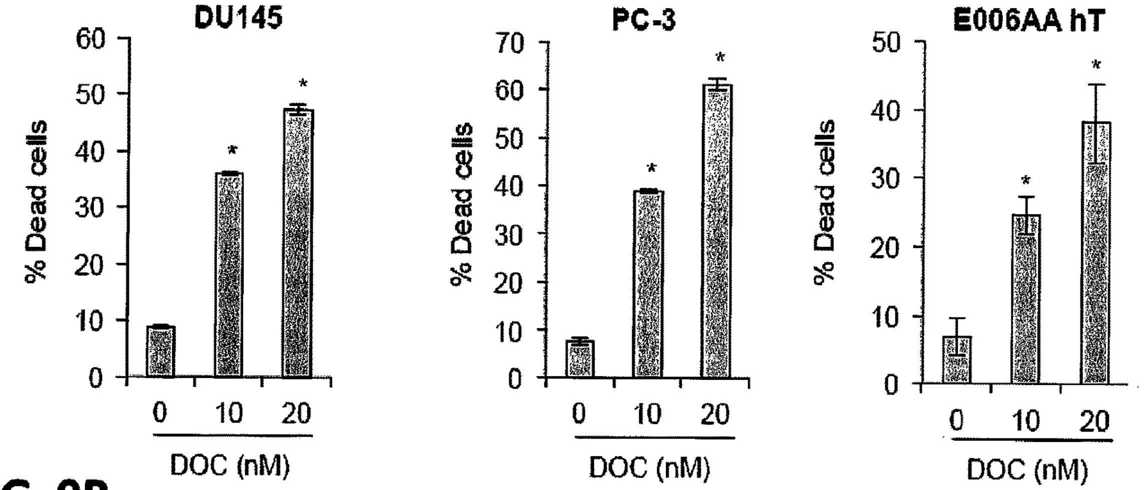
FIG. 9B
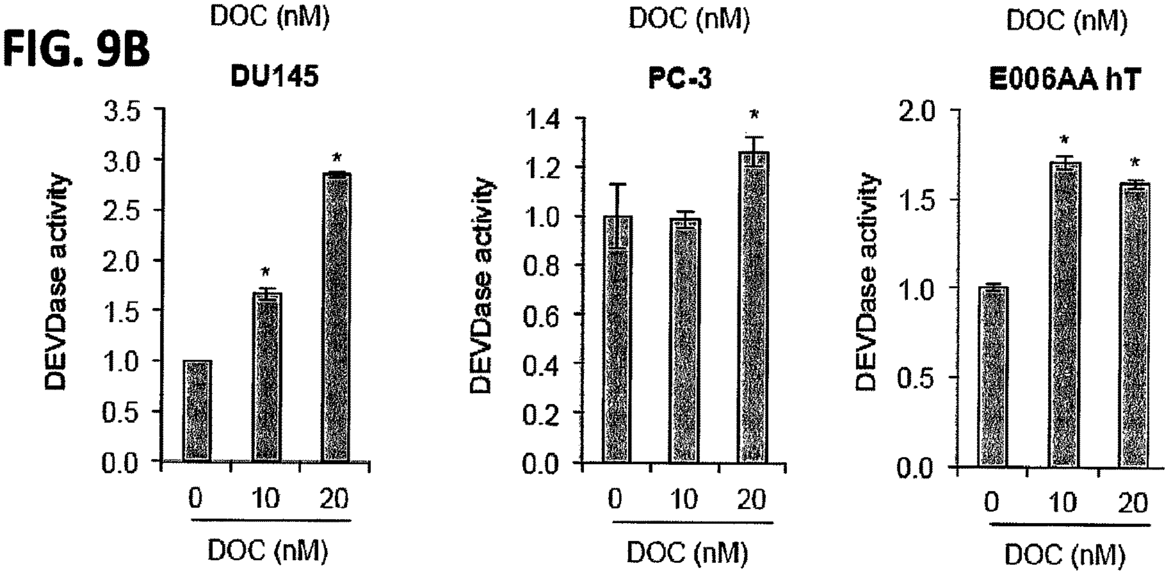
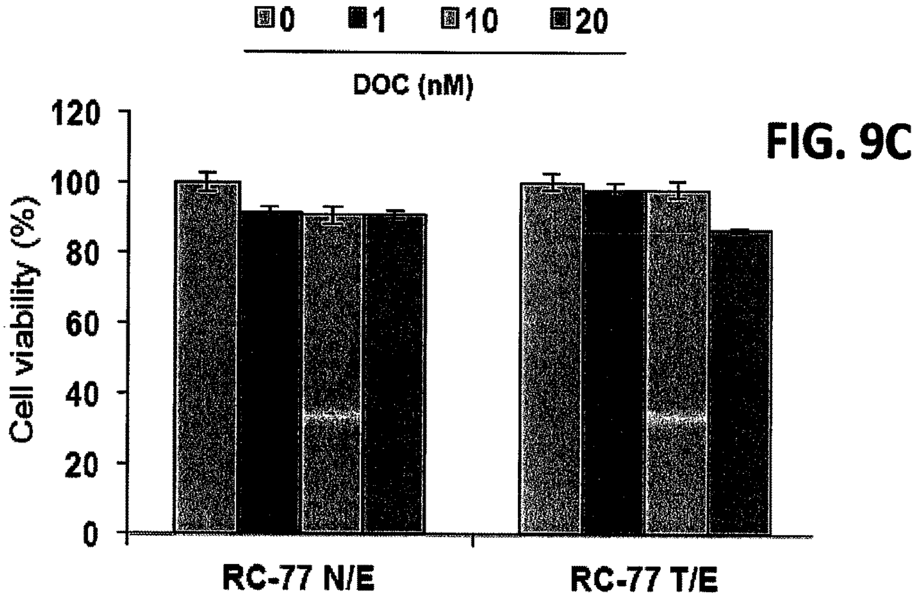
FIG. 9C

METHODS AND COMPOSITIONS FOR TREATING RESISTANT AND RECURRENT FORMS OF CANCER

CROSS-REFERENCE TO RELATED APPLICATIONS

This application is a national stage (371) application of International Application No. PCT/US2020/016177, filed Jan. 31, 2020, which claims priority to and the benefit of U.S. provisional patent application Ser. No. 62/800,071, entitled Methods and Compositions for Treating Resistant and Recurrent Forms of Cancer, filed Feb. 1, 2019. These applications are incorporated herein by reference in their entirety.

STATEMENT REGARDING FEDERALLY SPONSORED RESEARCH OR DEVELOPMENT

This invention was made with government support under CA160685 awarded by National Institutes of Health. The government has certain rights in this invention.

I. FIELD OF THE INVENTION

The present invention is directed to methods and compositions for treating drug resistant and aggressive forms of prostate cancer.

II. SUMMARY OF THE INVENTION

A first aspect of the present invention is directed to a method for treating prostate cancer in a subject. This method involves selecting a subject having prostate cancer and cytochrome c-deficiency, and administering, to the selected subject, a therapeutically effective amount of one or more agents capable of restoring cytochrome-c activity, thereby treating the prostate cancer.

Another aspect of the present invention is directed to a method of inducing apoptosis in drug resistant cancer cells. This method involves selecting drug resistant cancer cells having cytochrome-c deficiency, and administering to the selected cells, one or more agents that restore cytochrome-c activity in an amount effective to sensitize said cancer cells to drug induced apoptosis.

Another aspect of the present invention is directed to a combination therapeutic that comprises one or more agents that increases cytochrome-c activity and efficacy of a chemotherapeutic agent.

Another aspect of the present invention is directed to a method that involves selecting a subject having cancer, and obtaining a cell sample including tumor tissues/biopsy and blood samples from said subject. This method further involves measuring cytochrome-c expression levels and Drp1 phosphorylation levels in said sample.

Another aspect of the invention is directed to a method that involves determining whether a cytochrome c-deficiency is present by measuring a glycolytic marker. The glycolytic marker may preferably be lactate dehydrogenase A (LDHA).

A subset of men diagnosed with prostate cancer tends to develop greater therapeutic resistance and faster prostate cancer recurrence compared to other men. However, because the molecular mechanisms of this disparity have remained undefined, a therapeutic strategy for overcoming this resistance and treating these patients is currently not available. The experimental data provided herein provides the first comprehensive evidence that cytochrome-c deficiency in primary tumors and cancer cells abrogates apoptosome-mediated caspase activation and contributes to mitochondrial dysfunction, thereby promoting therapeutic resistance and prostate cancer aggressiveness in this subset of men. The cytochrome-c deficiency is mediated by inhibition of both Nrf1 nuclear accumulation and binding to the cytochrome-c promoter in resistant prostate cancer cells. Mechanistic analysis revealed that activation of c-Myc and NF-κB, or inhibition of Akt1, prevents Nrf1 nuclear translocation. In addition, a decrease in phosphorylated $Drp1^{S616}$ also contributes to defective cytochrome-c release and apoptosis resistance in certain prostate cancer cells. Genetic and pharmacological inhibition of c-Myc and NF-κB promotes Nrf1 binding to the cytochrome-c promoter, cytochrome-c expression, caspase activation, and cell death. Likewise, activation of Akt1 also promotes Nrf1 binding and cytochrome-c expression and well as cytochrome-c release from the mitochondrial via downstream activation of Drp1. Thus, while cytochrome-c deficiency promotes acquisition of glycolytic phenotypes and mitochondrial dysfunction, cytochrome-c restoration via inhibition of c-Myc and NF-κB, or activation of Akt1 restoration attenuates glycolysis in these resistant prostate cancer cells. Moreover, inhibition of c-Myc and NF-κB enhances efficacy of docetaxel in resistant tumor xenografts. Therefore, restoring cytochrome-c activity and/or expression in patients having a resistant form of prostate cancer will overcome therapeutic resistance and prostate cancer aggressiveness.

III. BRIEF DESCRIPTION OF THE DRAWINGS

Figure 1B:
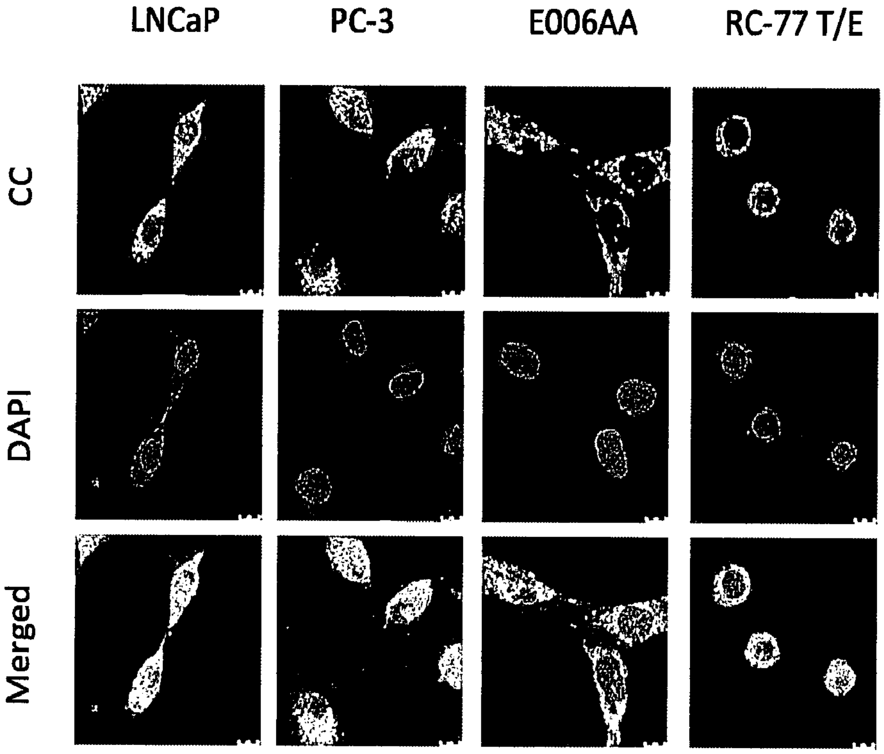
Figure 1C:
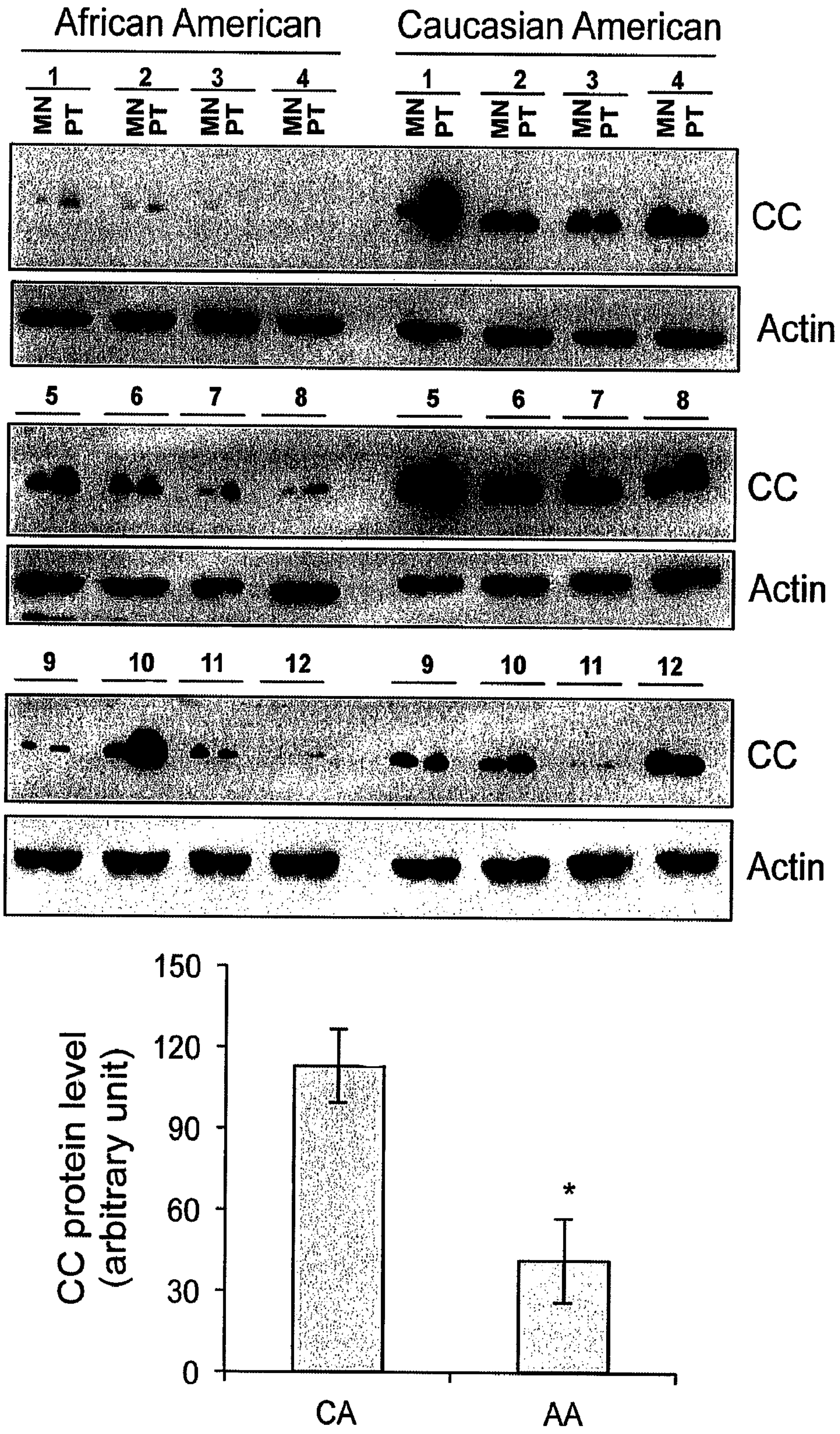
Figure 1D:
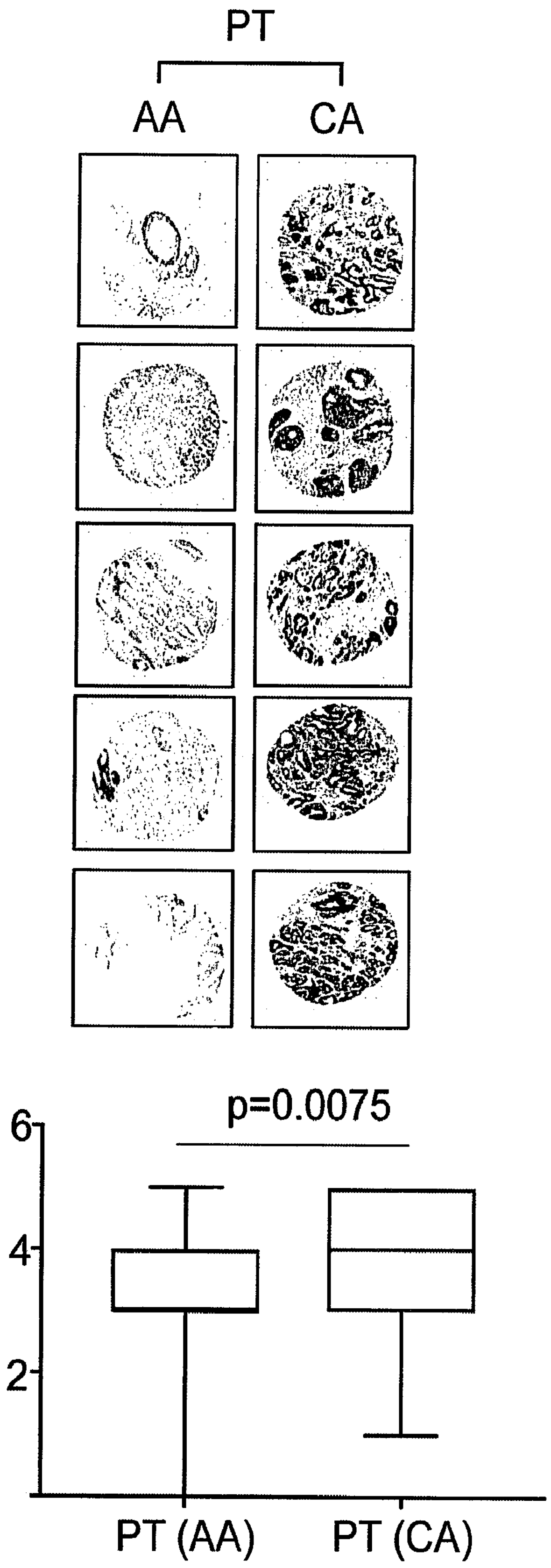

FIGS. 1A-1D. CC, a key component of apoptosome and OXPHOS system, is reduced in PCa cell lines and tumor specimens derived from AA men with PCa. FIG. 1A: Expression of the components of apoptosome complex, which include CC, Apaf-1, caspase-9 (Casp-9), and caspase-3 (Casp-3) were examined using immunoblotting in RWPE-1 (normal prostate epithelial cells), LNCaP, VCaP, PC-3, E006AA, RC-77 N/E and RC-77 T/E cells. Actin serves as a loading control. FIG. 1B: Expression of CC in LNCaP, PC-3, E006AA and RC-77 T/E cells using immunofluorescence. FIG. 1C: Immunoblot analysis of CC in primary tumor (PT) and matched non-tumor (MN) prostatic tissues from AA and CA men with PCa. Actin serves as a loading control. Densitometry analysis of immunoblots of CC in PT tissues from AA and CA men with PCa (n=12 for each race). FIG. 1D: Immunohistochemistry (IHC) analysis of CC expression in PT in AA and CA men with PCa using tissue microarray (TMA) sections. Scoring analysis of IHC of CC in PT tissues from AA (n=92) and CA (n=89) men with PCa. Data in FIG. 1C represent mean±SD of n=12. Significant differences between means were assessed using analysis of variance (ANOVA) and GraphPad Prism Version 6.0. *p<0.05 vs CA primary tumor.

Figure 2D:
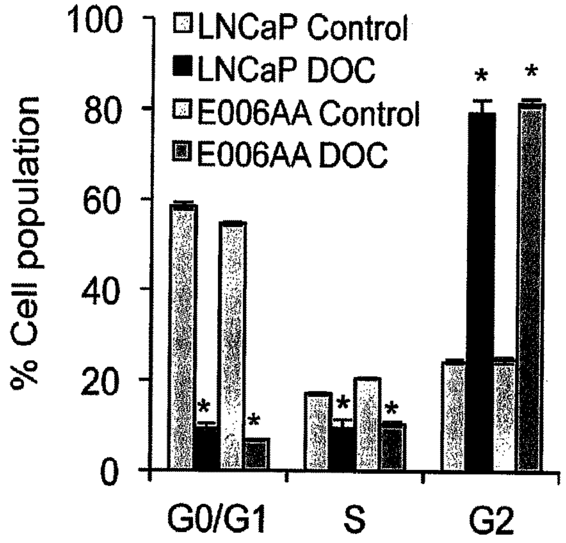
Figure 2E:
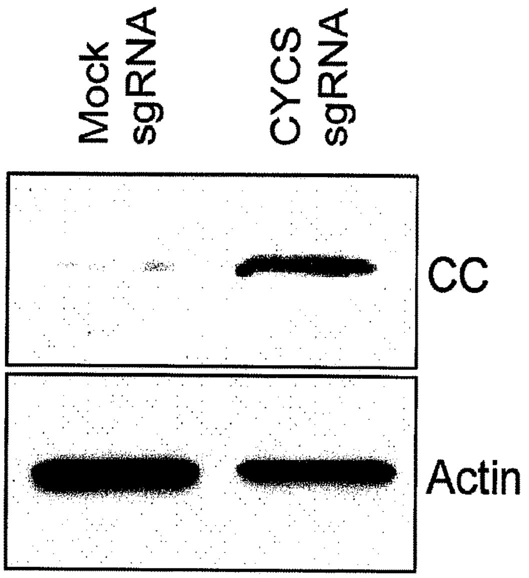
Figure 2F:
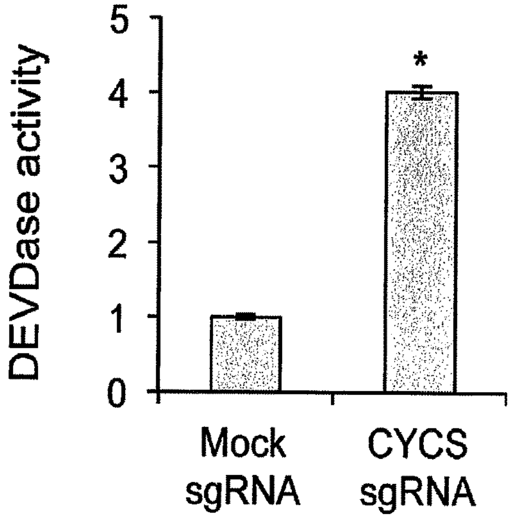
Figure 2G:
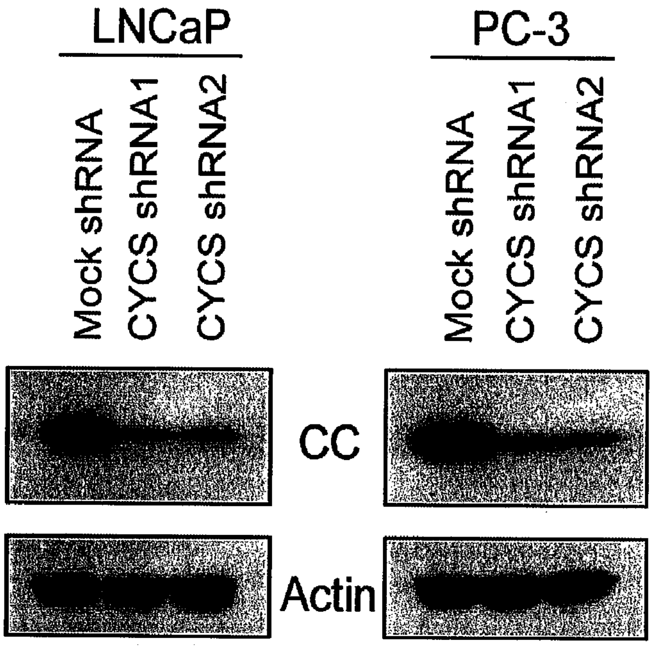
Figure 2H:
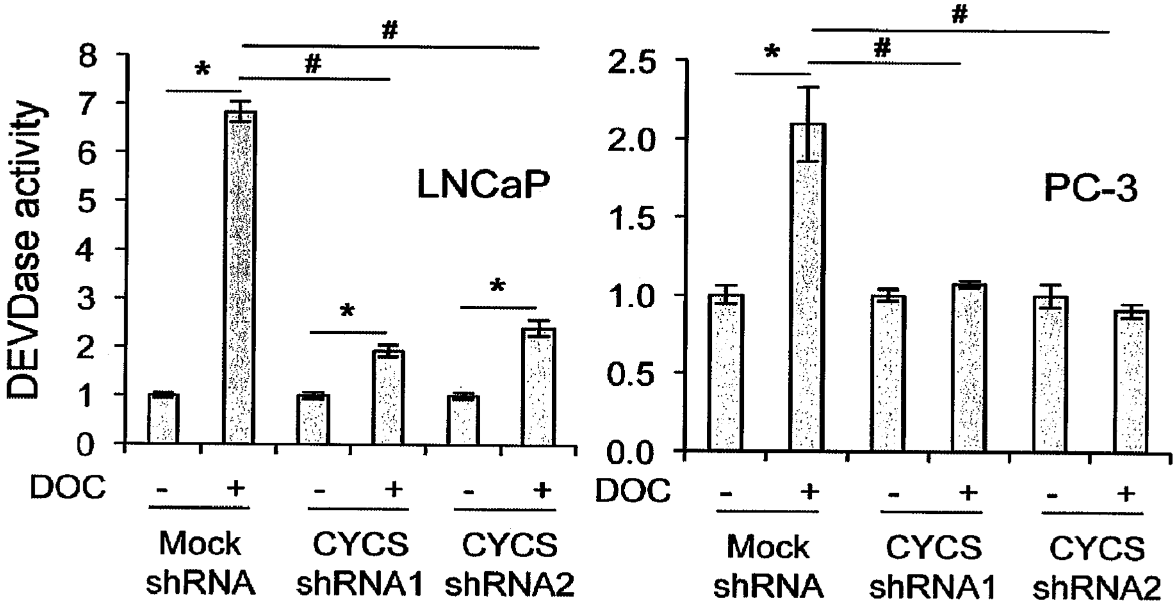

FIGS. 2A-2K. Lack of CC causes apoptosome dysfunction and apoptosis resistance in AA PCa cells whereas CC-silencing induces mitochondrial/apoptosome dysfunction in CA PCa cells. FIG. 2A: Purified cytosol isolated from E006AA cells was reconstituted with CC with or without ATP to quantitate apoptosome-mediated caspase-3 activity using a substrate cleavage (DEVDase) assay. FIG. 2B: Cell death in LNCaP and E006AA cells upon docetaxel (DOC) treatment (for 24 hrs.) was quantified using a Trypan blue assay. FIG. 2C: Caspase-3 activity (i.e., DEVDase activity) was determined in LNCaP and E006AA cells after treatment with DOC for 24 hrs. FIG. 2D: Cell cycle phase analysis was quantified in LNCaP and E006AA cells after treatment with DOC for 24 hrs. FIG. 2E: Endogenous CC was overexpressed in E006AA cells using a CRISPR-SAM approach and expression of CC was determined using immunoblotting. Actin serves as a loading control. FIG. 2F: Endogenous CC was overexpressed in E006AA cells using a CRISPR-SAM approach and caspase-3 activity was measured using a DEVDase assay. FIG. 2G: CC was knocked down in LNCaP and PC-3 cells using shRNAs and expression of CC was determined using immunoblotting. Actin serves as a loading control. FIG. 2H: Caspase-3 activity (DEVDase activity) was measured in mock- and CC-silenced LNCaP and PC-3 cells treated with DOC (10 nM) for 24 hrs. FIG. 2I: Mitochondrial mass (mitoMass) was measured in mock- and CC-silenced LNCaP and PC-3 cells using flow cytometry. FIG. 2J: Mitochondrial ROS (mitoROS) was measured in mock- and CC-silenced LNCaP and PC-3 cells using flow cytometry. FIG. 2K: MtDNA copy number was analyzed in mock- and CC-silenced LNCaP and PC-3 cells. Data represent mean±SD of 3 independent experiments. Significant differences between means were assessed using analysis of variance (ANOVA) and GraphPad Prism Version 6.0. $^{*}p<0.05$ vs respective controls or groups. $^{\#}p<0.05$ vs mock shRNA.

Figure 3A:
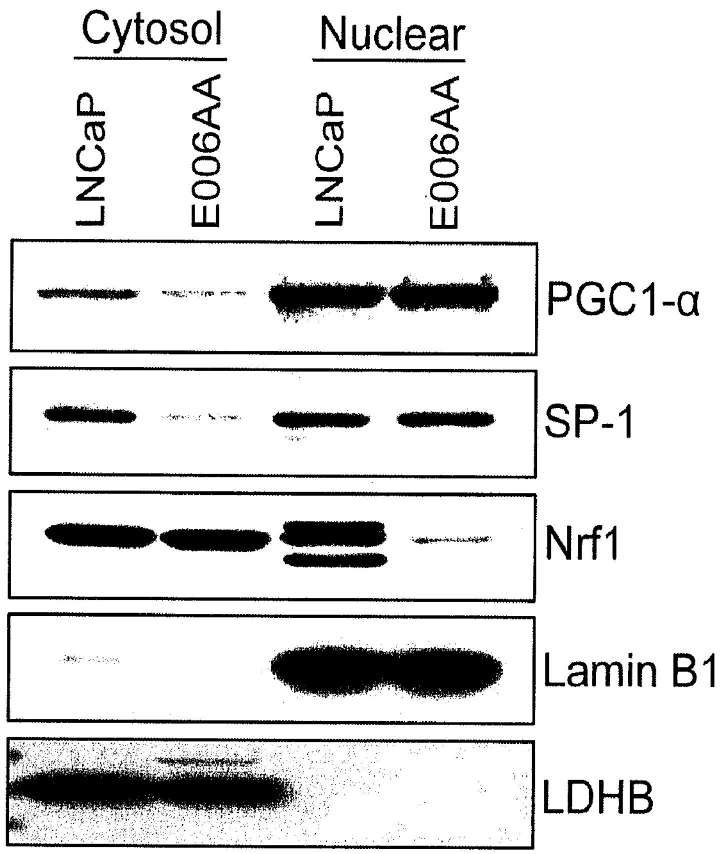
Figure 3B:
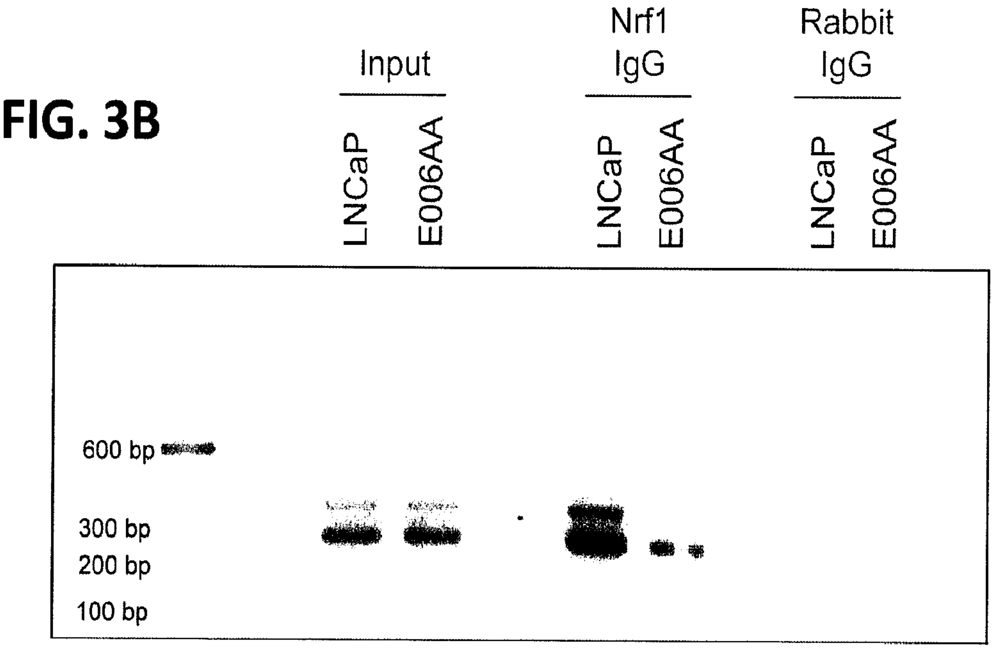
Figure 3C:
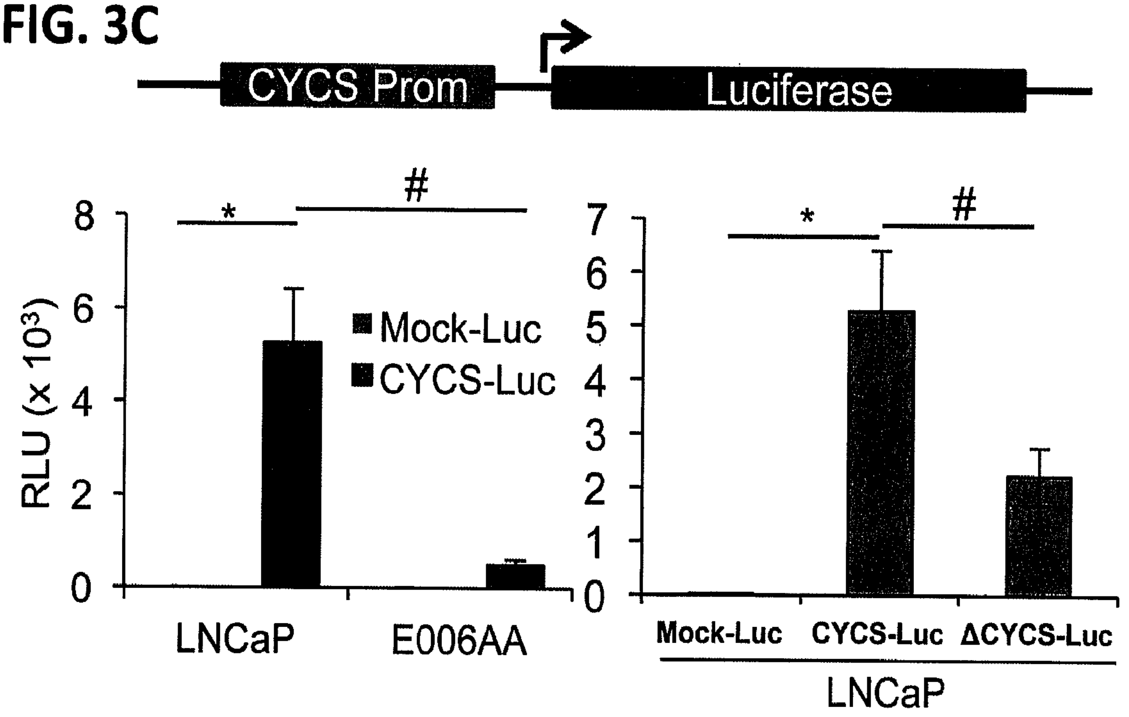
Figure 3D:
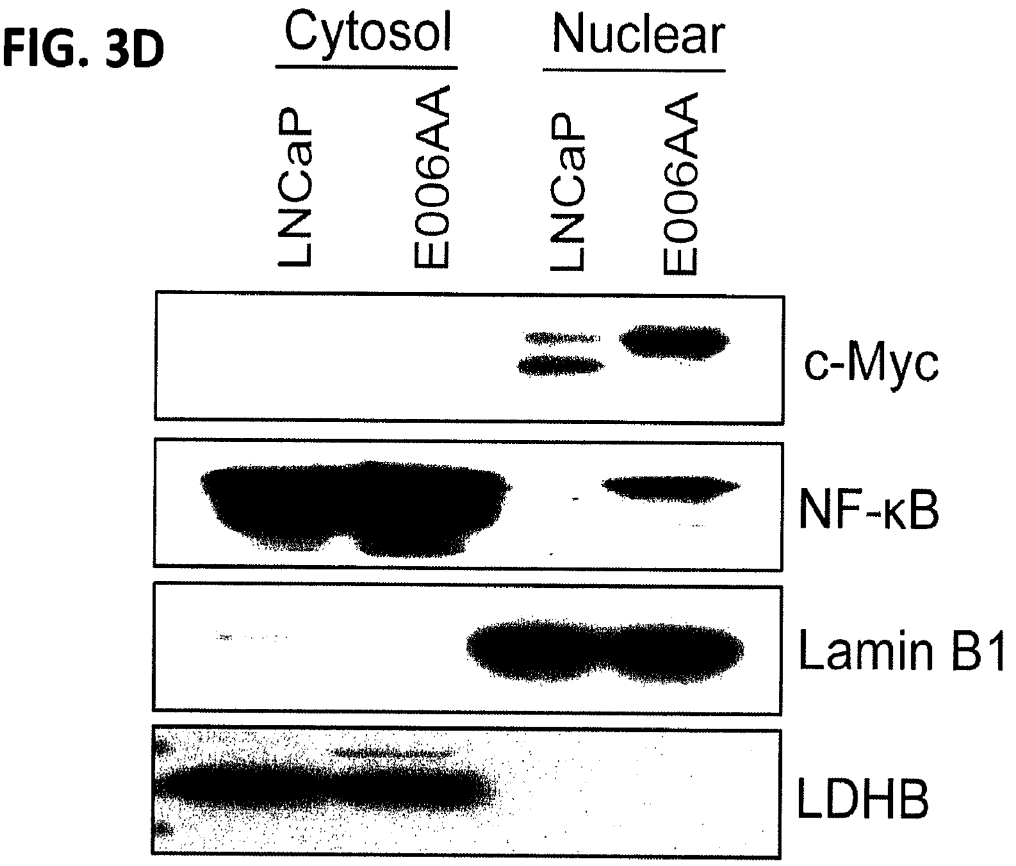
Figure 3G:
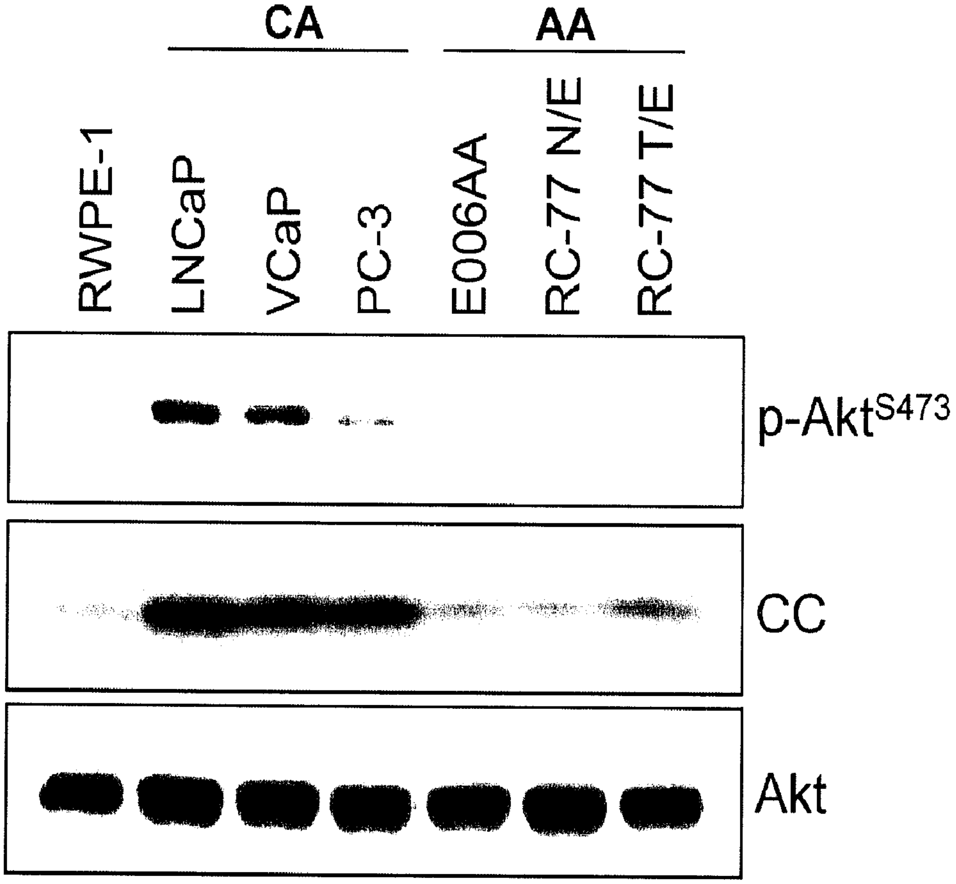

FIGS. 3A-3G. Inhibition of nuclear respiration factor-1 (Nrf1) translocation to nucleus contributes to reduced CC expression in AA PCa cells. FIG. 3A: Cytosolic and nuclear levels of PGC1-α, SP-1, and Nrf1 in LNCaP and E006AA cells were determined using immunoblot analysis. Lamin B1 and LDHB serve as marker proteins as well as loading controls for nuclear and cytosolic fractions, respectively. FIG. 3B: Nrf1 binding efficiency with CC promoter in LNCaP and E006AA cells was determined using a chromatin immunoprecipitation (ChIP) assay. FIG. 3C: LNCaP and E006AA cells were transfected with CC promoter constructs. Luciferase assay detected CC promoter activity. Deletion of Nrf1 binding site on CC promoter inhibited luciferase activity in LNCaP cells. FIG. 3D: Cytosolic and nuclear level of c-Myc and NF-κB in LNCaP and E006AA cells were determined using immunoblot analysis. Lamin B1 and LDHB serve as marker proteins as well as loading controls for nuclear and cytosolic fractions, respectively. FIG. 3E: Representative immunoblot analysis of c-Myc in MN and PT tissue AA and CA men with PCa. Actin serves as a loading control. Densitometry analysis of immunoblots of c-Myc in PT tissues from AA and CA men with PCa (n=12 for each race). FIG. 3F: Expression level of phosphorylated form of Akt (p-$Akt^{S473}$) in LNCaP and E006AA cells. Total Akt serves as a loading control. FIG. 3G: Expression of p-$Akt^{S473}$ and CC using immunoblotting in RWPE-1 (normal prostate epithelial cells), LNCaP, VCaP, PC-3, E006AA, RC-77 N/E and RC-77 T/E cells. Total Akt serves as a loading control. Data represent mean±SD of 3 independent experiments. Significant differences between means were assessed using analysis of variance (ANOVA) and GraphPad Prism Version 6.0. $^{*}p<0.05$ vs respective controls, and $^{\#}p<0.05$ vs respective groups.

Figure 4A:
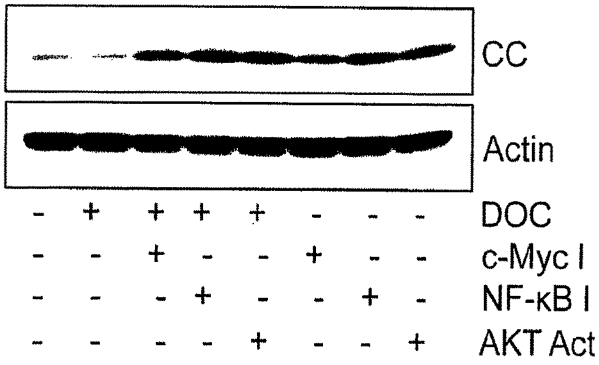
Figure 4B:
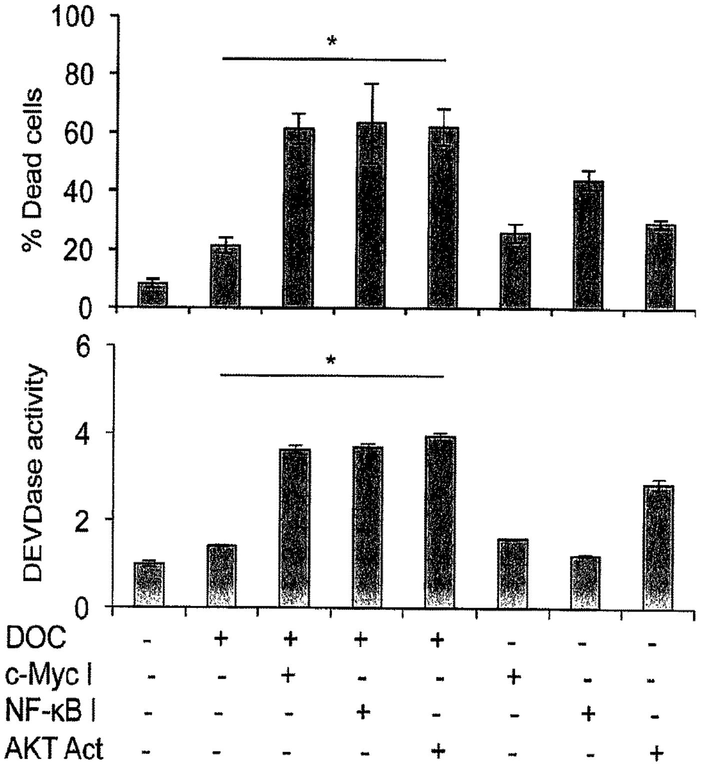
Figure 4C:
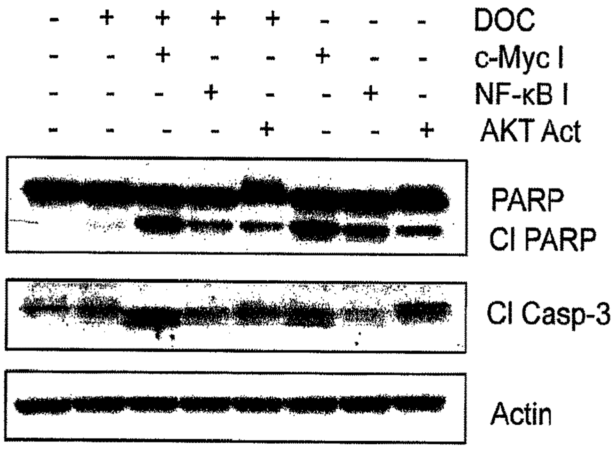

FIGS. 4A-4G. Inhibition of c-Myc and/or NF-κB and activation of AKT enhance Nrf1 nuclear translocation, restores CC expression, and induces cell death. FIG. 4A: Immunoblot analysis of CC in E006AA cells after treatment with DOC (10 nM for 24 hrs.) alone or in combination with either c-Myc inhibitor (c-Myc I, 75 μM) or NF-κB inhibitor (NF-κB I, 50 μM) or AKT activator (AKT Act, 5 μM). Actin serves as a loading control. FIG. 4B: Quantification of cell death using Trypan blue assay and caspase-3 activity determination in E006AA cells upon treatment with DOC (for 24 hrs.) alone or in combination with either c-Myc inhibitor or NF-κB inhibitor or AKT activator. $^{*}p<0.05$ vs DOC treated cells. FIG. 4C: Immunoblot analysis of cleaved PARP (Cl PARP) and cleaved caspase-3 (Cl Casp-3) in E006AA cells treated with DOC alone, c-Myc inhibitor alone, NF-κB inhibitor alone, AKT activator alone or DOC in combination with Myc inhibitor or NF-κB inhibitor or AKT activator. Actin serves as a loading control. FIG. 4D: Immunoblot analysis of Nrf1 in cytosolic and nuclear fractions isolated from E006AA cell treated with DOC (for 24 hrs.) alone or in combination with either c-Myc inhibitor or NF-κB inhibitor or AKT activator. LDHB and TBP serve as marker proteins and loading controls for cytosolic and nuclear fractions, respectively. FIG. 4E: Nrf1 binding efficiency with CC promoter in E006AA cells upon treatment with DOC (for 24 hrs.) alone or in combination with either c-Myc inhibitor or NF-κB inhibitor or AKT activator using ChIP analysis. LNCaP cells were used as positive controls. FIG. 4F: E006AA cells were transfected with CC promoter constructs (CYCS-Luc or ΔCYCS-Luc) and treated with either c-Myc inhibitor or NF-κB inhibitor or AKT activator, followed by luciferase assay after 24 hrs. to detect CC promoter activity. $^{*}p<0.05$ vs untreated control, $\#p<0.05$ vs respective groups. FIG. 4G: c-Myc, p65 subunit of NF-κB and PTEN was knock down in E006AA cells using siRNA. Expression of these proteins and CC was determined using immunoblotting. Actin serves as a loading control. Data represent mean±SD of 3 independent experiments.

Figure 5A:
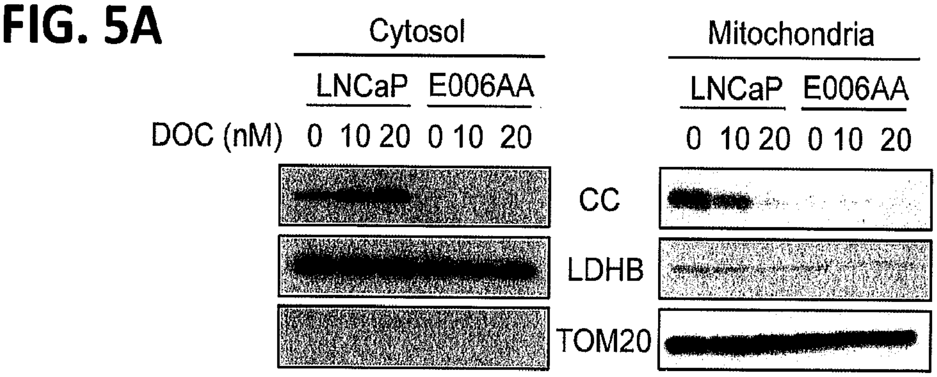
Figure 5C:
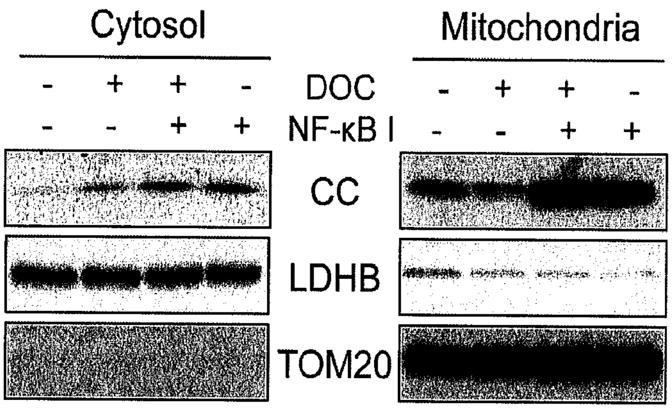
Figure 5B:
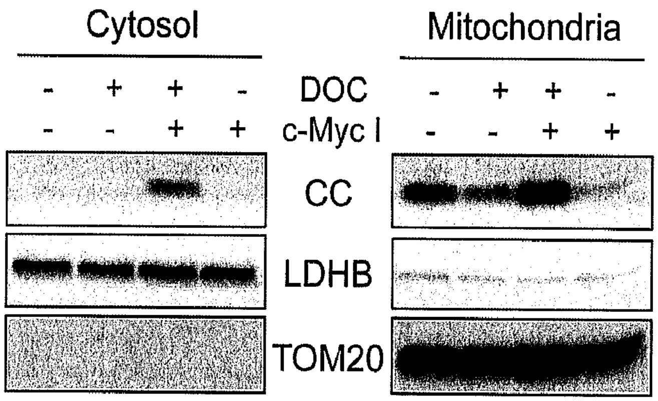
Figure 5D:
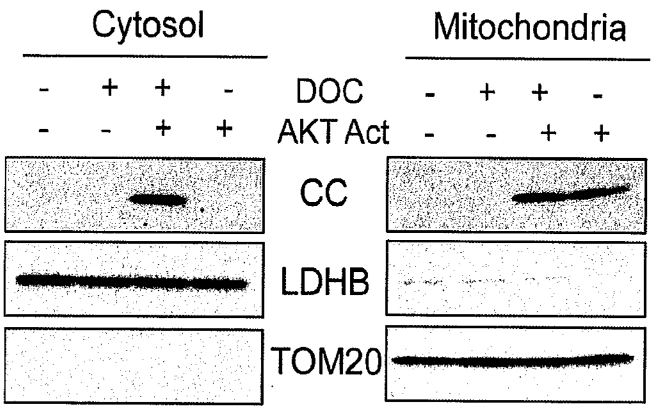
Figure 5I:
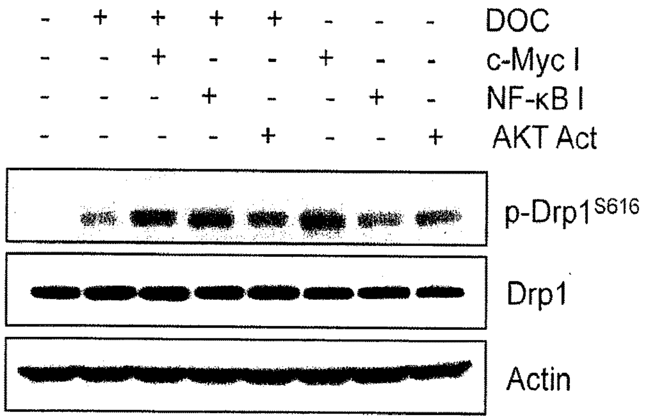
Figure 5J:
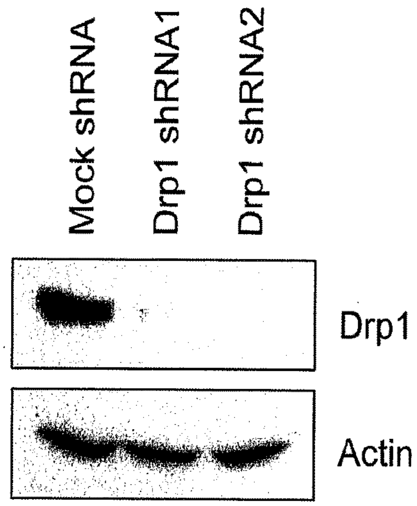
Figure 5K:
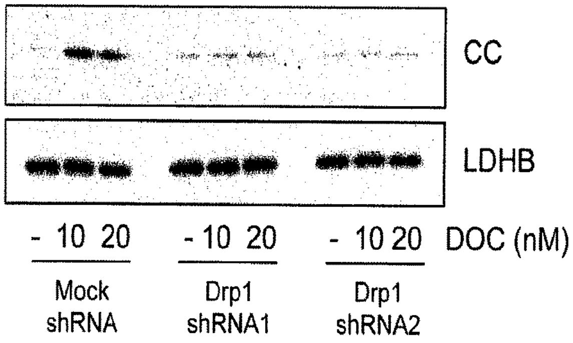

FIGS. 5A-5L. CC release machinery at the mitochondrial outer membrane is defective and deficiency of Drp1 phosphorylation at serine 616 contributes to defective CC release in AA cells. FIG. 5A: Immunoblot analysis of CC in LNCaP and E006AA cells after treatment with DOC for 24 hrs. LDHB and TOM20 serve as markers and loading controls for cytosolic and mitochondrial fractions, respectively. FIGS. 5B-D: Immunoblot analysis of CC in cytosolic and mitochondrial fractions isolated from E006AA cells upon treatment with DOC (for 24 hrs.) alone or c-Myc inhibitor alone or c-Myc inhibitor and DOC (FIG. 5B); DOC alone or NF-κB inhibitor alone or NF-κB inhibitor and DOC (FIG. 5C); DOC alone or AKT activator alone; or AKT activator and DOC (FIG. 5D). LDHB and TOM20 serve as markers and loading controls for cytosolic and mitochondrial fractions, respectively. FIG. 5E: Immunoblot analysis of Drp1 and Opal in cytosolic and mitochondrial fractions isolated from LNCaP and E006AA cells treated with DOC alone. LDHB and TOMM20 serve as markers and loading controls for cytosolic and mitochondrial fractions, respectively. FIG. 5F: Immunoblot analysis of total Drp1, p-$Drp1^{S616}$, and p-$Drp1^{S637}$ in LNCaP and E006AA cells. GAPDH serves as a loading control. FIG. 5G: Immunoblot analysis of total Erk2 and its phosphorylated form in LNCaP and E006AA cells. Total Erk2 serves as a loading control. FIG. 5H: Expression level of total Akt, p-$Akt^{S473}$, total Drp1, and p-$Drp1^{S616}$ in LNCaP cells treated with AKT inhibitor wortmanin (Wort, 1 μM). Total Akt and Drp1 serve as loading controls. FIG. 5I: Immunoblot analysis of p-$Drp1^{S616}$ and Drp1 in E006AA cells after treatment with DOC (10 nM for 24 hrs.) alone or in combination with either c-Myc inhibitor (c-Myc I, 75 μM) or NF-κB inhibitor (NF-κB I, 50 μM) or AKT activator (AKT Act, 5 μM). Actin serves as a loading control. FIG. 5J: Drp1 was knocked down in LNCaP cells using shRNAs and expression of Drp1 was determined using immunoblotting. Actin serves as a loading control. FIG. 5K: Immunoblot analysis of CC expression in cytosolic fractions isolated from mock and Drp1-silenced LNCaP cells treated with DOC for 24 hrs. LDHB serves as a loading control.

Figure 5L:
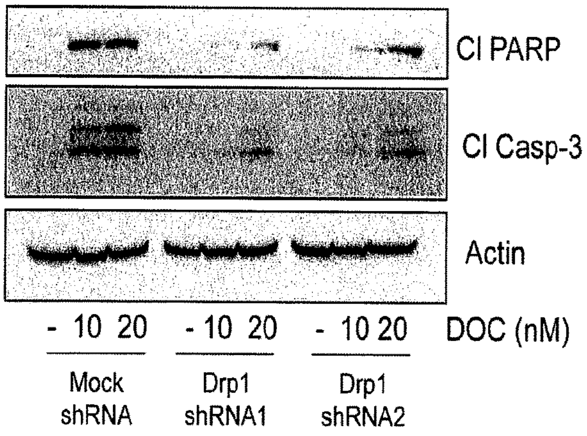

FIG. 5L: Immunoblot analysis of PARP cleavage (Cl PARP) and caspase-3 cleavage (Cl Casp-3) in mock and Drp1-silenced LNCaP cells treated with DOC for 24 hrs. Actin serves as a loading control.

Figure 6E:
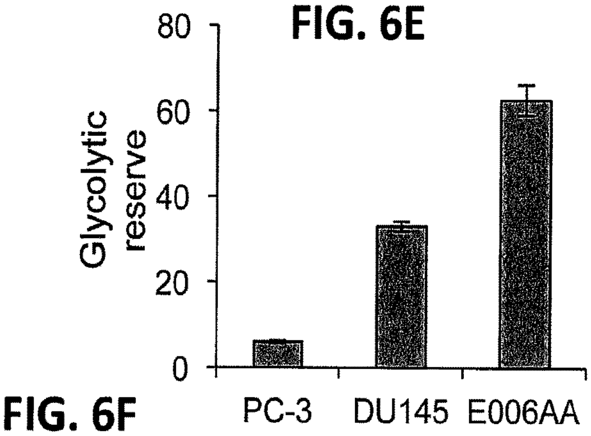
Figure 6G:
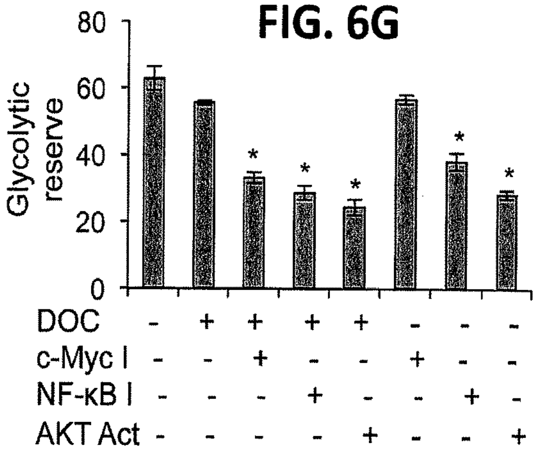
Figure 6F:
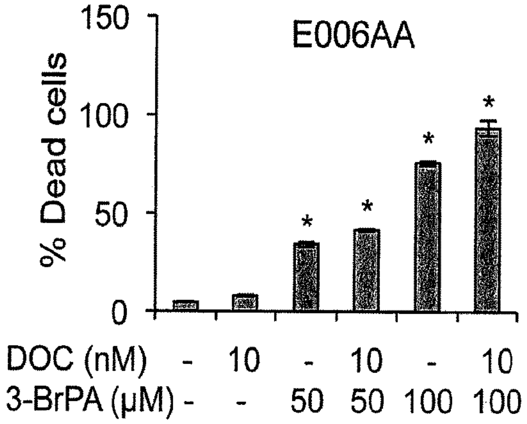
Figure 6H:
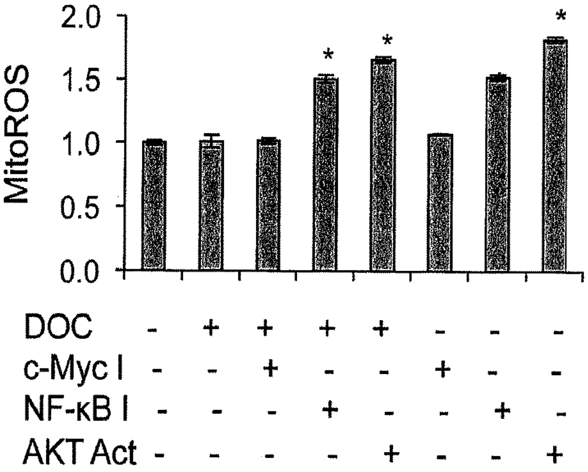
Figure 6I:
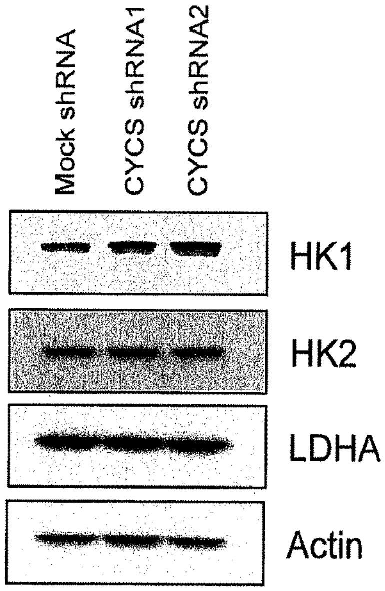

FIGS. 6A-I. CC-deficiency causes metabolic reprogramming in AA primary tumor and AA PCa cells. FIG. 6A: Expression levels of OXPHOS complex subunits and FAK in LNCaP and E006AA cells by immunoblot analysis. NDUFA9 for Complex I, succinate dehydrogenase A (SDHA) for Complex II, UQCRC2 for Complex III, cytochrome c oxidase subunit IV (COX IV) for Complex IV; ATPSA for Complex V. GAPDH serves as a loading control. FIG. 6B: Expression level of glycolytic enzymes including focal adhesion kinase (FAK), hexokinase 1 (HK1), hexokinase 2 (HK2), phosphofructokinase platelet isoform (PFKP), pyruvate kinase M ½ (PKM ½), and lactate dehydrogenase A (LDHA) in LNCaP and E006AA cells using immunoblot analysis. GAPDH serves as a loading control. FIG. 6C: Expression of LDHA at mRNA level using RT-PCR in LNCaP and E006AA cells. FIG. 6D: Expression of LDHA at mRNA level using RT-PCR in primary tumor isolated from AA and CA men with PCa. FIG. 6E: Measurement of glycolytic reserve capacity in PC-3, DU145, and E006AA cells using Seahorse XF analyzer. FIG. 6F: Cell death quantification in E006AA cells treated with DOC alone or DOC in combination with glycolytic disruptor 3-BrPA (3-Bromopyruvate) for 24 hrs. FIG. 6G: Measurement of glycolytic reserve capacity using Seahorse XF analyzer in E006AA cells treated with DOC or DOC in combination with either c-Myc inhibitor or NF-κB inhibitor or AKT activator. FIG. 6H: Measurement of mitochondrial ROS production using MitoSOX dye in E006AA cells treated with DOC or DOC in combination with either c-Myc inhibitor or NF-κB inhibitor or AKT activator using flow cytometry. FIG. 6I: Expression level of glycolytic enzymes including hexokinase 1 (HK1), hexokinase 2 (HK2), phosphofructokinase platelet isoform (PFKP), pyruvate kinase M 2 (PKM2), and lactate dehydrogenase A (LDHA) in mock- and CC-silenced LNCaP cells using immunoblot analysis. Actin serves as a loading control. Data represent mean±SD of 3 independent experiments. Significant differences between means were assessed using analysis of variance (ANOVA) and GraphPad Prism Version 6.0. *p<0.05 vs respective controls.

Figure 7A:
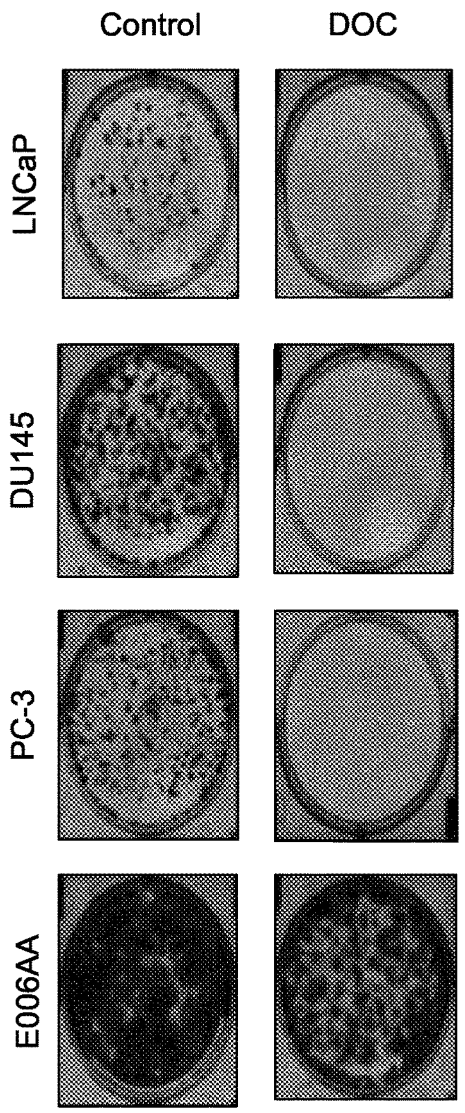
Figure 7B:
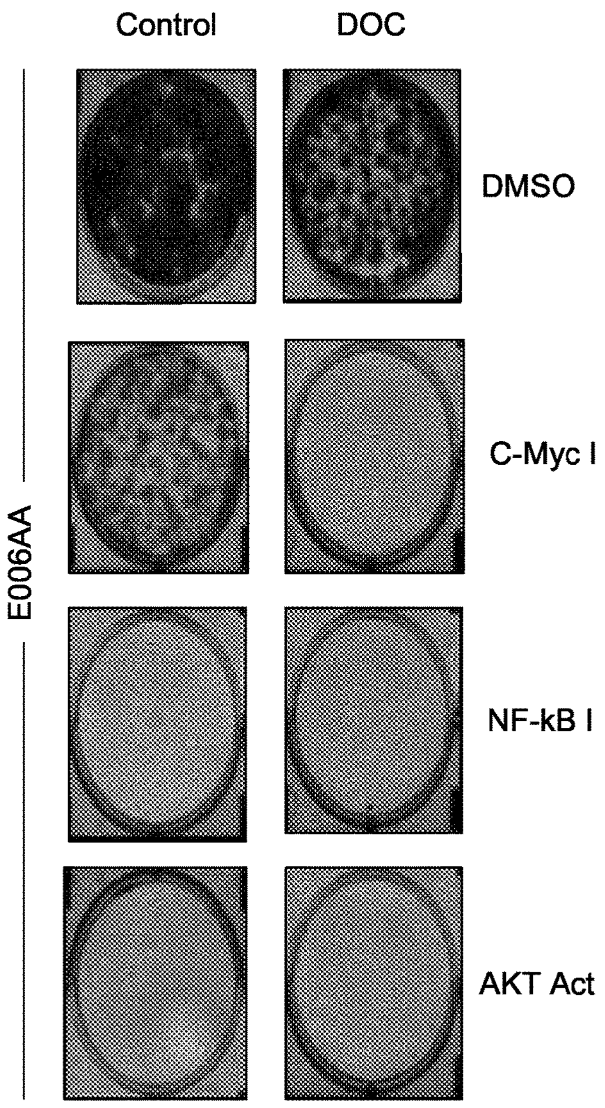
Figures 7C, 7D:
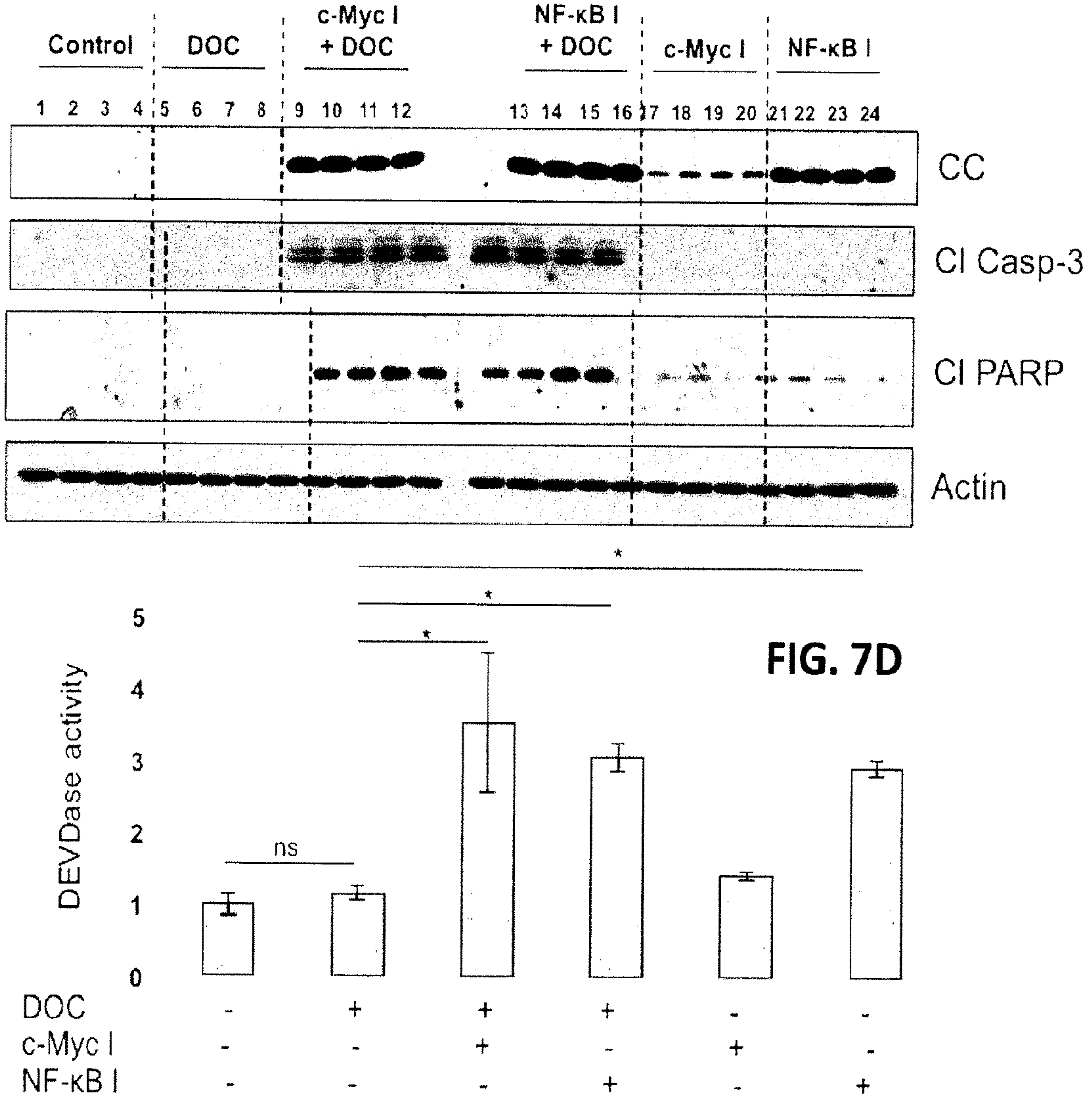

FIGS. 7A-7D. Inhibition of c-Myc or NF-κB enhances therapeutic efficacy of DOC in AA PCa xenografts. FIG. 7A: Clonogenic analysis of LNCaP, DU145, PC-3 and E006AA cells in response to DOC treatment. FIG. 7B: Clonogenic analysis of E006AA cells treated with DOC or DOC in combination with either c-Myc inhibitor or NF-κB inhibitor or AKT activator. FIG. 7C: Immunoblot analysis of CC, caspase-3 cleavage, or PARP cleavage in E006AA hT xenografts treated with DOC or DOC in combination with c-Myc inhibitor or NF-κB inhibitor. FIG. 7D: Caspase-3 activity in E006AA hT xenografts treated with DOC or DOC in combination with c-Myc inhibitor or NF-κB inhibitor. Data represent mean±SD of 4 independent experiments. Significant differences between means were assessed using analysis of variance (ANOVA) and GraphPad Prism Version 6.0. *p<0.05 vs respective controls.

Figure 8A:
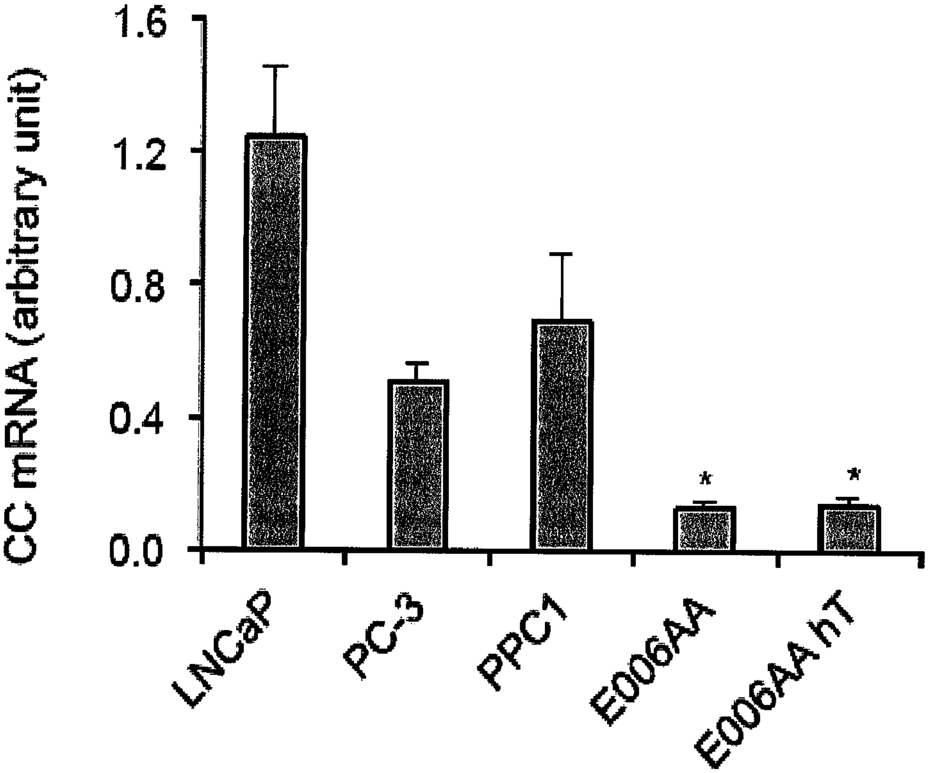
Figure 8B:
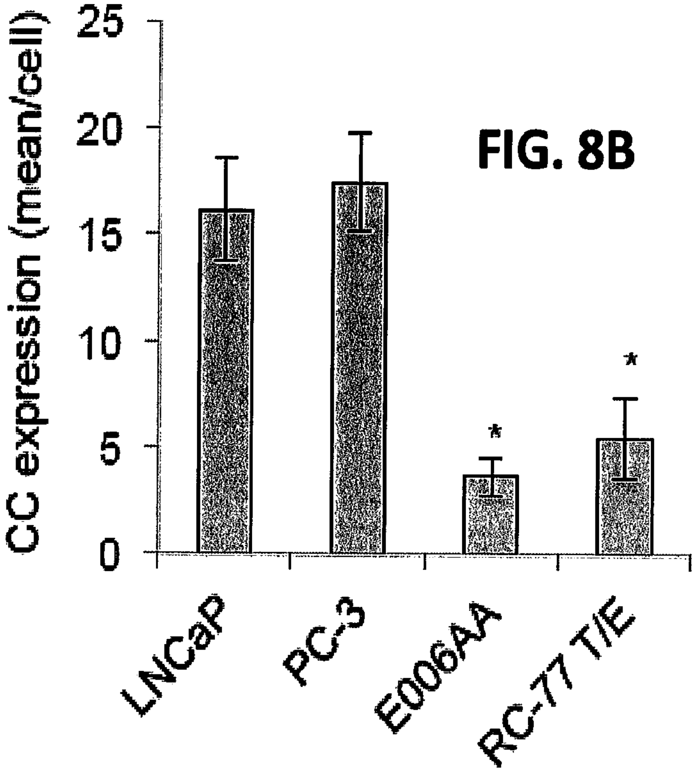

FIGS. 8A-B: FIG. 8A shows the expression of cytochrome c (CC) mRNA in PCa cells using RT-PCR. The mean intensity per cell of CC in immunofluorescence images is shown in FIG. 1B (n=10). Data represent mean±SD of 3 independent experiments. * p<0.05 vs respective groups.

FIGS. 9A-9C: These figures show cell death (FIG. 9A) and DEVDase activity (FIG. 9B) in PCa cells in response to DOC treatment (10 and 20 nM) for 24 hrs. quantified using Trypan blue and DEVDase activity, respectively. Effect of docetaxel (DOC for 24 hrs.) on cell viability in AA PCa cells is shown in FIG. 9C. Data represent mean±SD of 3 independent experiments. * p<0.05 vs controls.

Figure 10A:
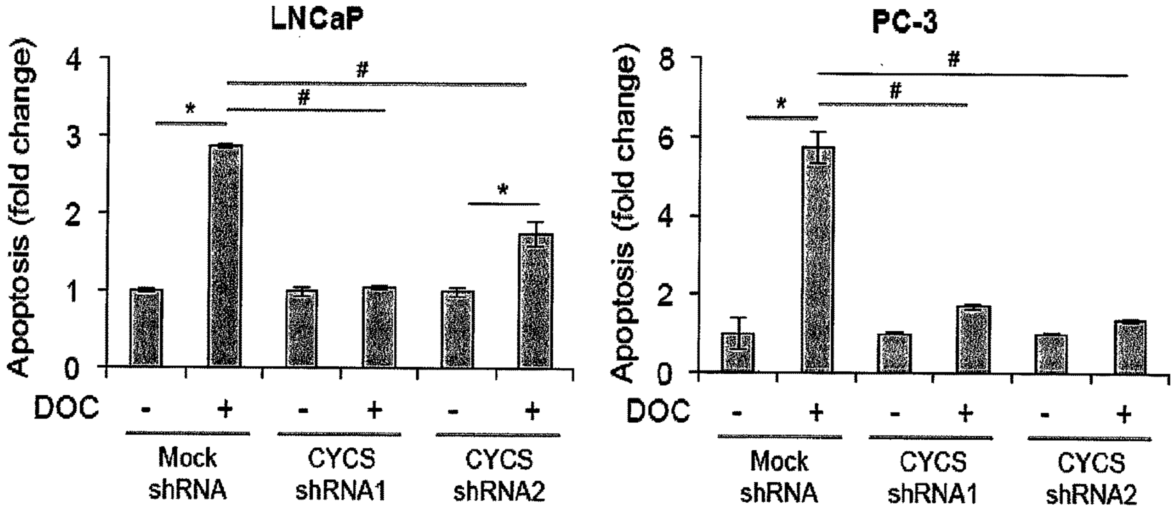
Figure 10B:
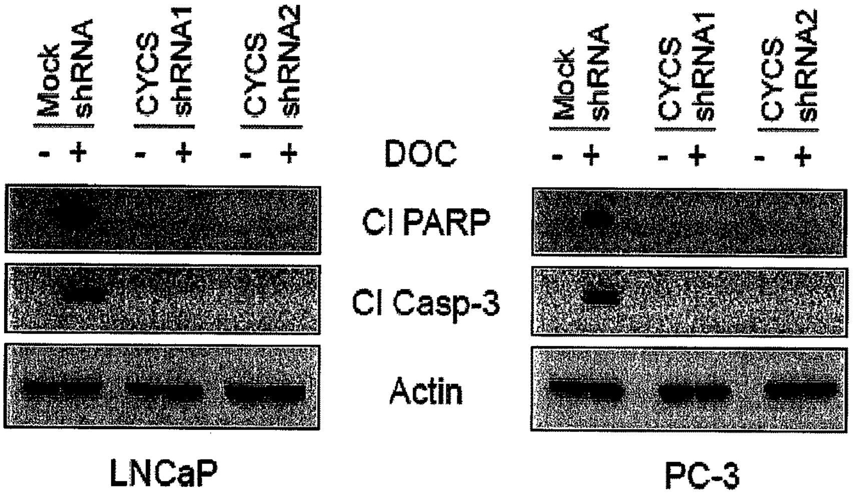
Figure 10C:
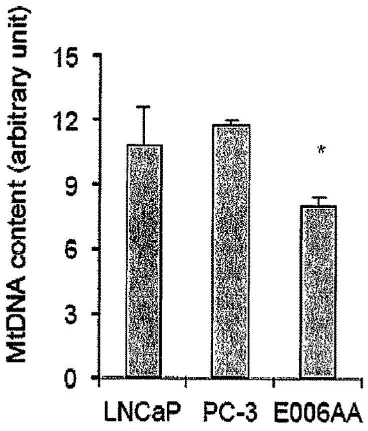

FIGS. 10A-10C: CC expression was knocked down in LNCaP and PC-3 cells using shRNAs followed by treatment with DOC (20 nM) for 24 hrs. (LNCaP) or 48 hrs. (PC-3). Apoptotic cell death was analyzed using annexin V-FITC/PI labeling (as shown in FIG. 10A). Whole cell lysates were prepared and analyzed for cleaved PARP and caspase-3 using immunoblotting (as shown in FIG. 10B). MtNDA content in CA and AA PCa cell was analyzed using RT-PCR as shown in FIG. 10C. Data represent mean±SD of 3 independent experiments. * p<0.05 vs respective groups; #p<0.05 vs respective groups.

Figure 11A:
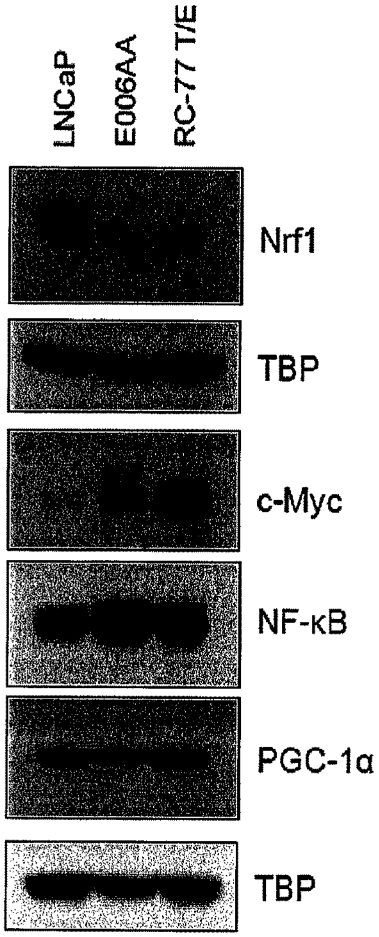
Figure 11B:
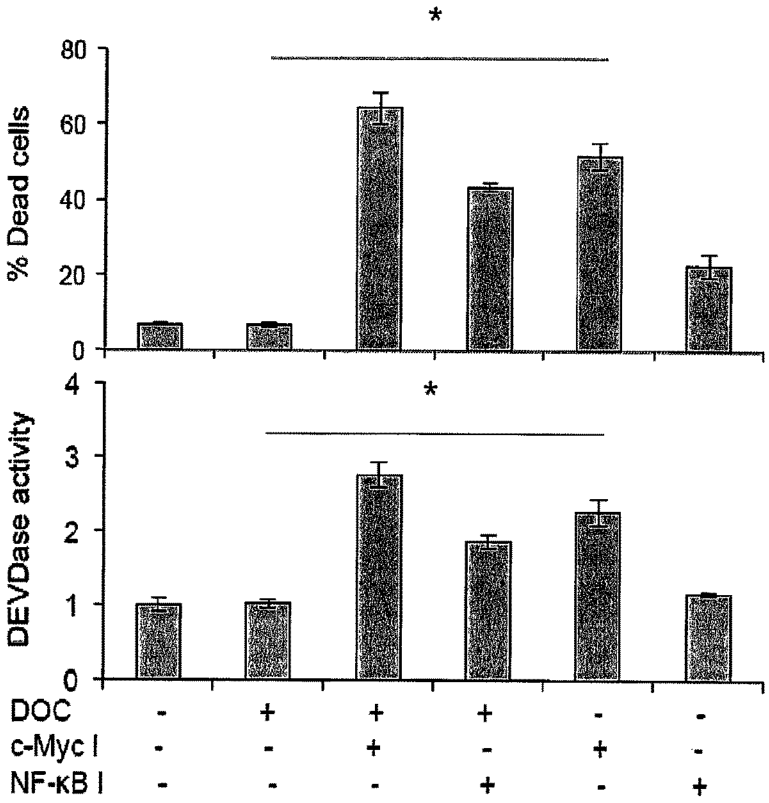
Figure 11C:
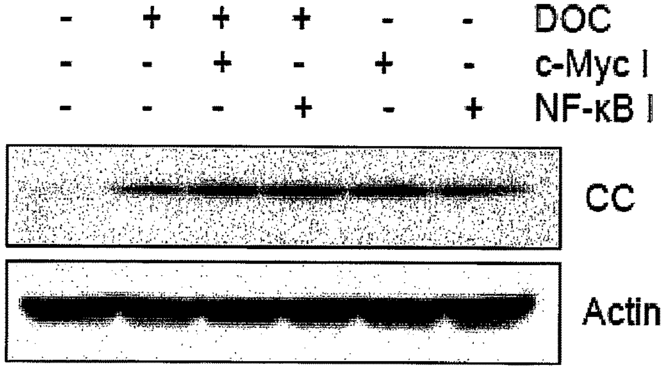

FIGS. 11A-11C: Nuclear levels of Nrf1, c-Myc, NF-κB and PGC-1α in CA and AA PCa cells were analyzed using immunoblotting (as shown in FIG. 11A). Cell death quantification and DEVDase activity measurement is shown in FIG. 11B; and CC expression analysis (as shown in FIG. 11C) were performed in RC-77 T/E AA PCa cells following DOC treatment with or without c-Myc I and NF-κB I treatment for 24 hrs. Data represent mean±SD of 3 independent experiments. *p<0.05 vs respective groups.

Figure 12:
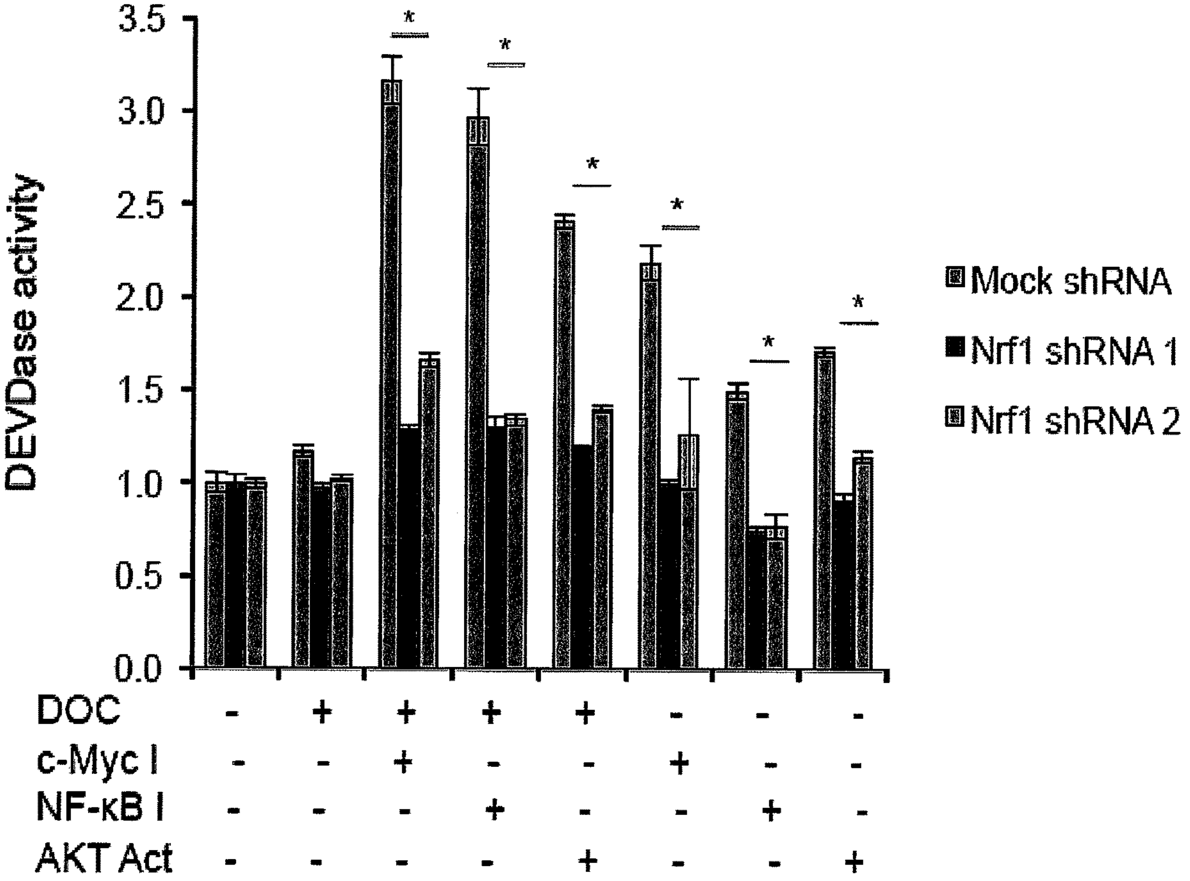

FIG. 12: Knockdown of Nrf1 using shRNA inhibits DEVDase activity in E006AA cells treated with either c-Myc inhibitor (c-Myc I) or NF-κB inhibitor (NF-κB I) or AKT activator (AKT Act) alone or in combination with DOC (10 nM) after 24 hrs. Data represent mean±SD of 3 independent experiments. *p<0.05 vs respective groups.

Figure 13A:
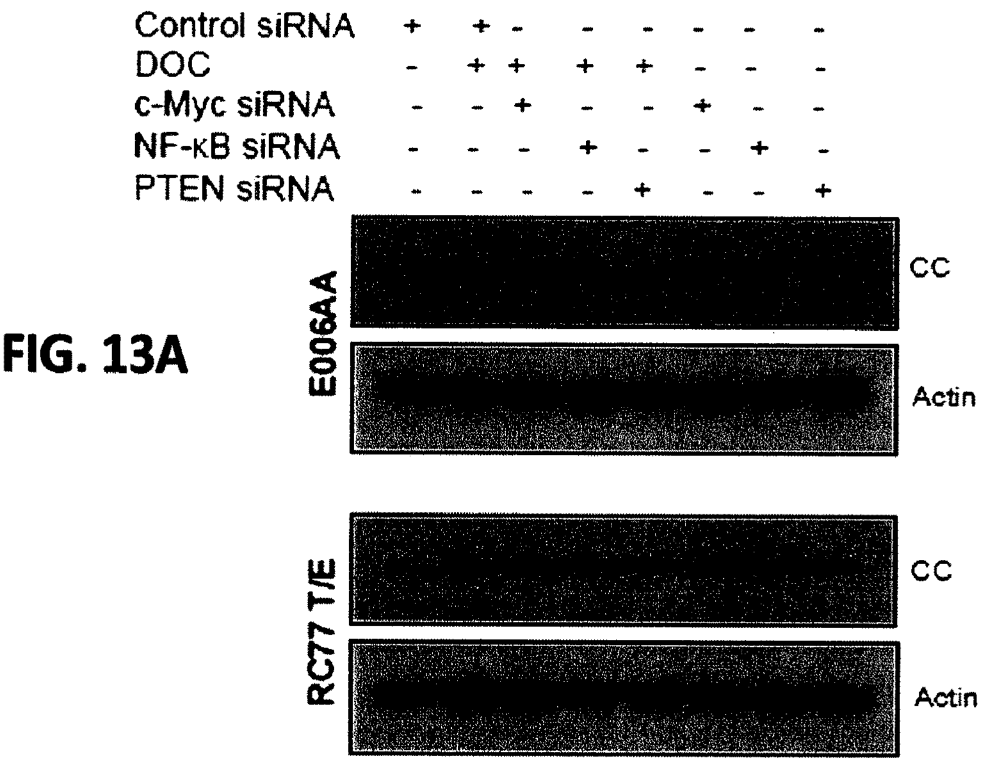
Figure 13B:
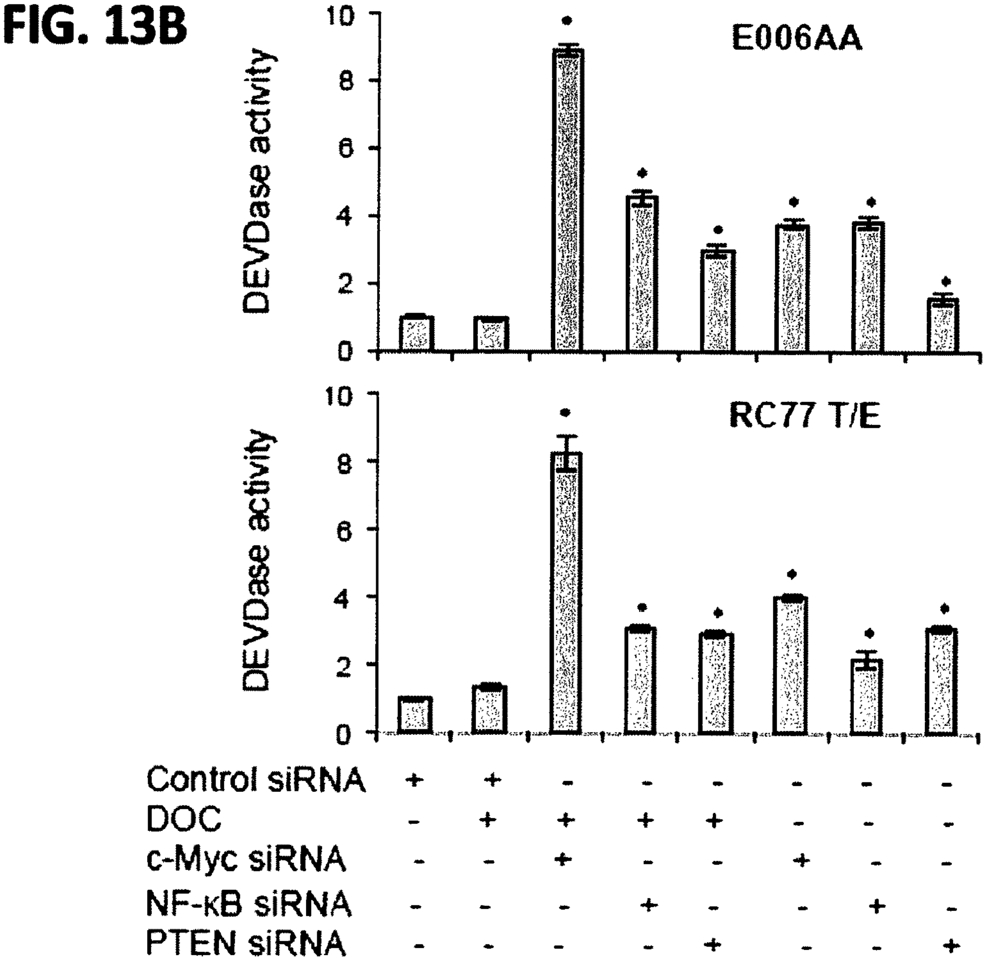

FIGS. 13A-B: Either c-Myc or p65 subunit of NF-kB or PTEN were knocked down in E006AA and RC77 T/E cells using siRNA followed by treatment with DOC (10 nM) for 24 hrs. Whole cell lysate were prepared and analyzed for CC expression (shown in FIG. 13A) and DEVDase activity (shown in FIG. 13B). Data represent mean±SD of 3 independent experiments. *p<0.05 vs respective groups.

Figure 14A:
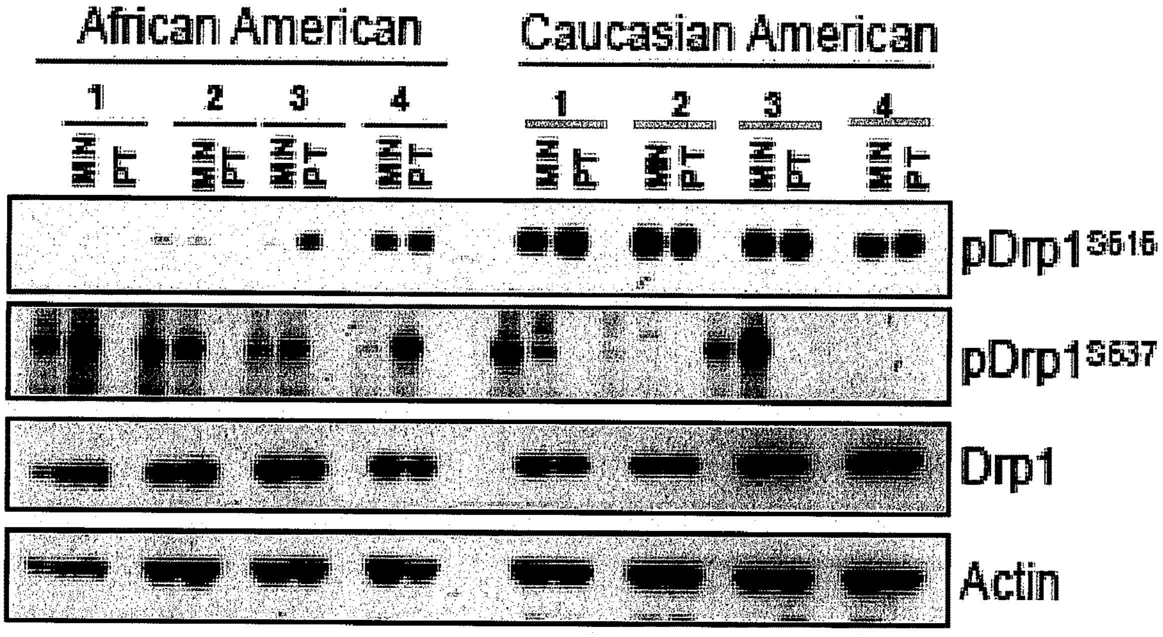
Figure 14B:
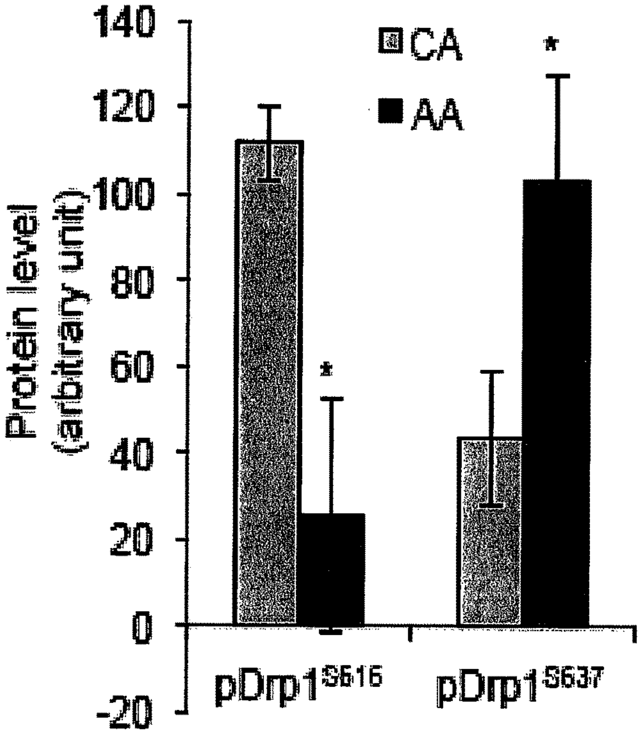

FIGS. 14A-B: FIG. 14A is a representative immunoblot of $pDrp1^{S616}$, $pDrp1^{S637}$ and Drp1 in matched nontumor (MN) and primary tumor (PT) tissue samples from AA and CA men with PCa. FIG. 14B is a densitometry analysis of immunoblots of $pDrp1^{S616}$ and $pDrp1^{S637}$ PT tissues from AA and CA men with PCa (n=12 for each race). Actin serves as a loading control. *p<0.05 vs respective groups.

Figure 15A:
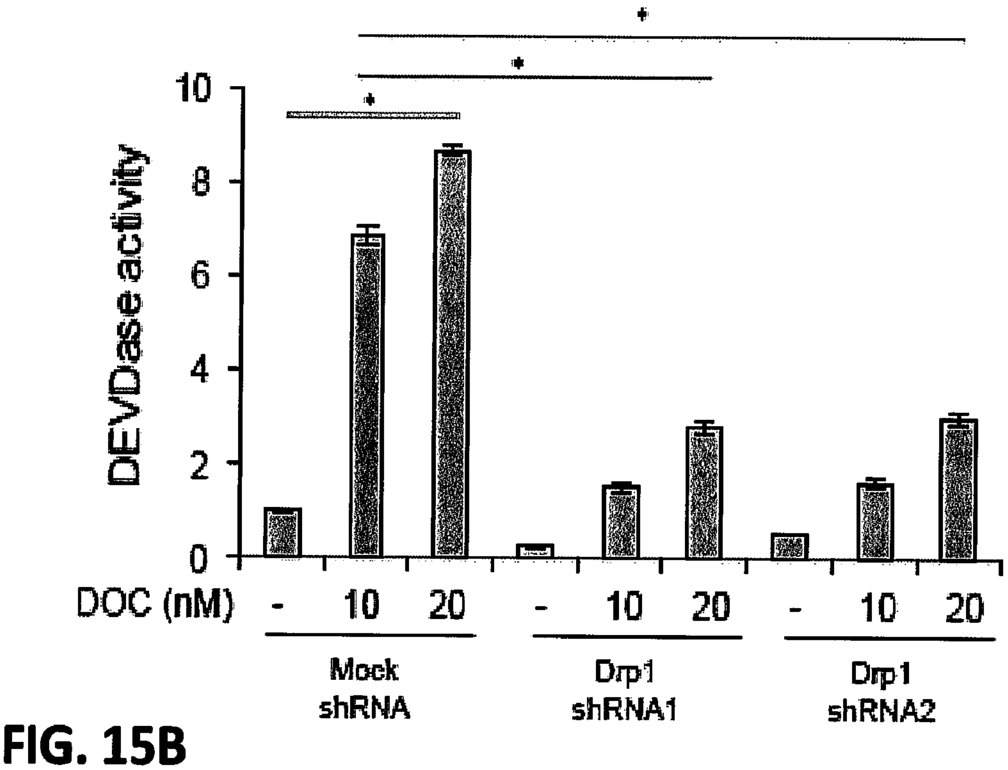
Figure 15B:
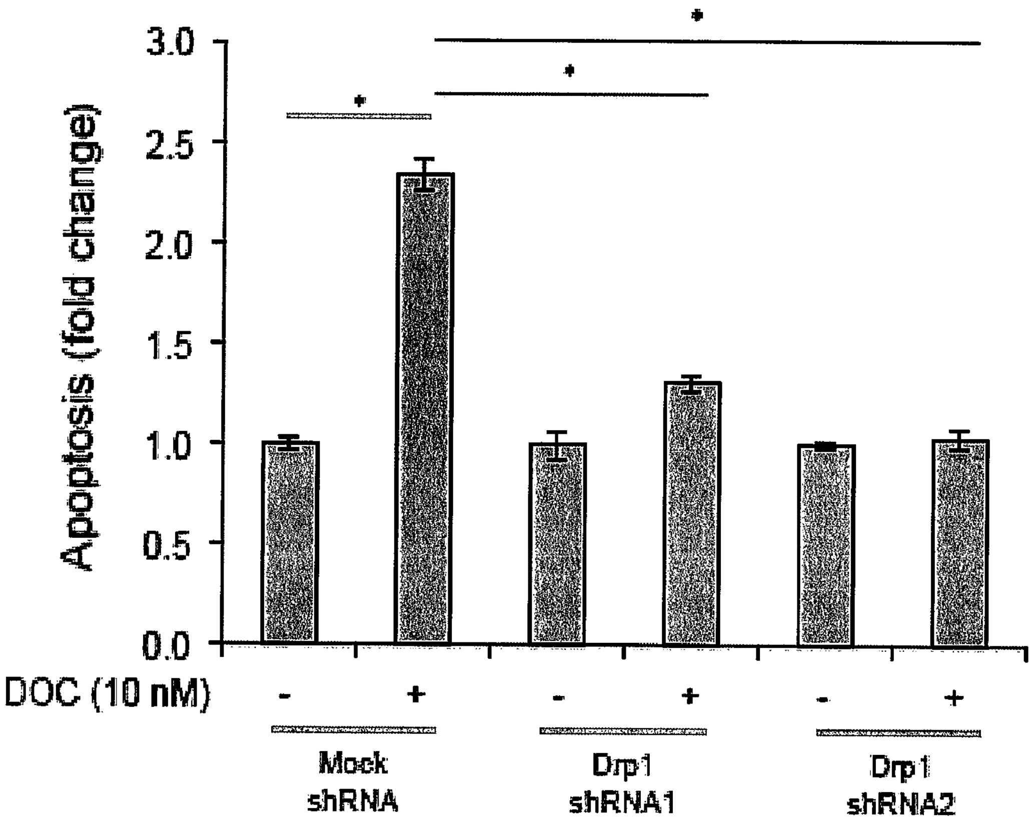

FIGS. 15A-B: Knockdown of Drp1 using shRNA inhibits DEVDase activity (as shown in FIG. 15A) and apoptotic cell death (as shown in FIG. 15B) in LNCaP cells treated with DOC for 24 hrs. Data represent mean±SD of 3 independent experiments. *p<0.05 vs respective control groups.

Figure 16A:
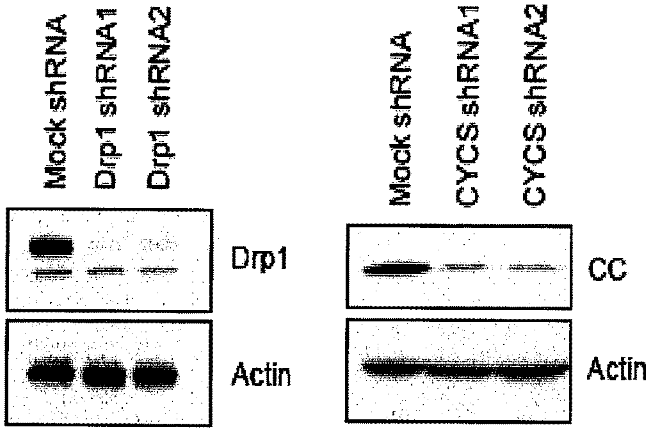
Figure 16B:
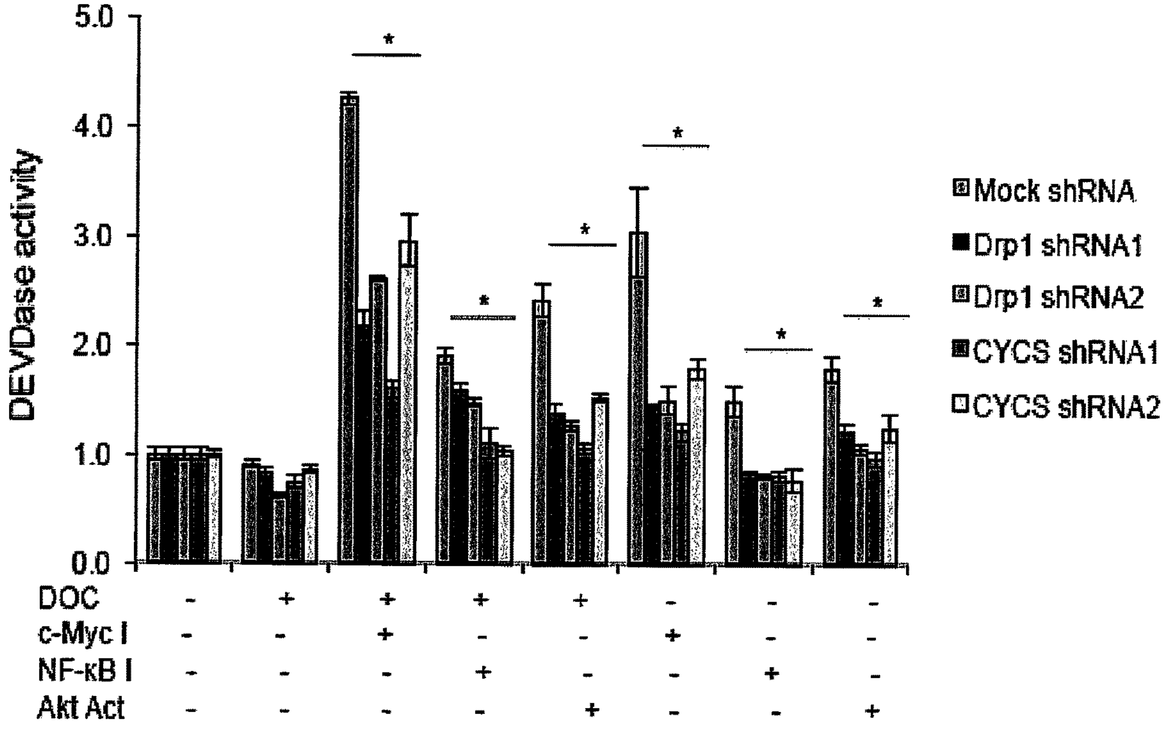

FIGS. 16A-B: Knockdown of Drp1 and CYCS using shRNA (a shown in FIG. 16A) inhibit DEVDase activity in E006AA cells treated with either c-Myc inhibitor (c-Myc I) or NF-κB inhibitor (NF-κB I) or AKT activator (AKT Act) alone or in combination with DOC (10 nM) after 24 hrs. (FIG. 16B). Data represent mean±SD of 3 independent experiments. * p<0.05 vs respective groups; #p<0.05 vs respective groups.

Figure 17A:
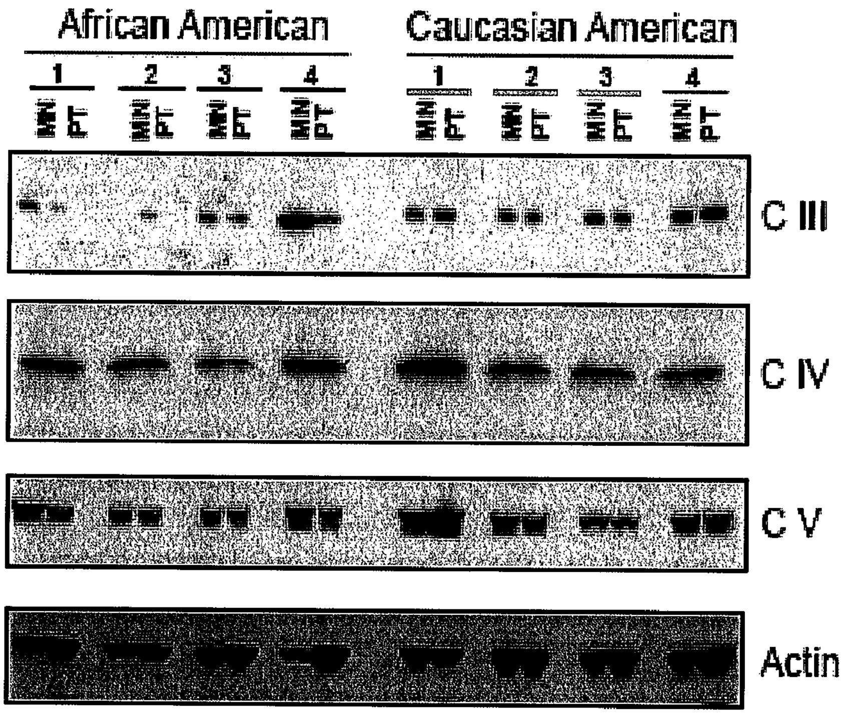
Figure 17B:
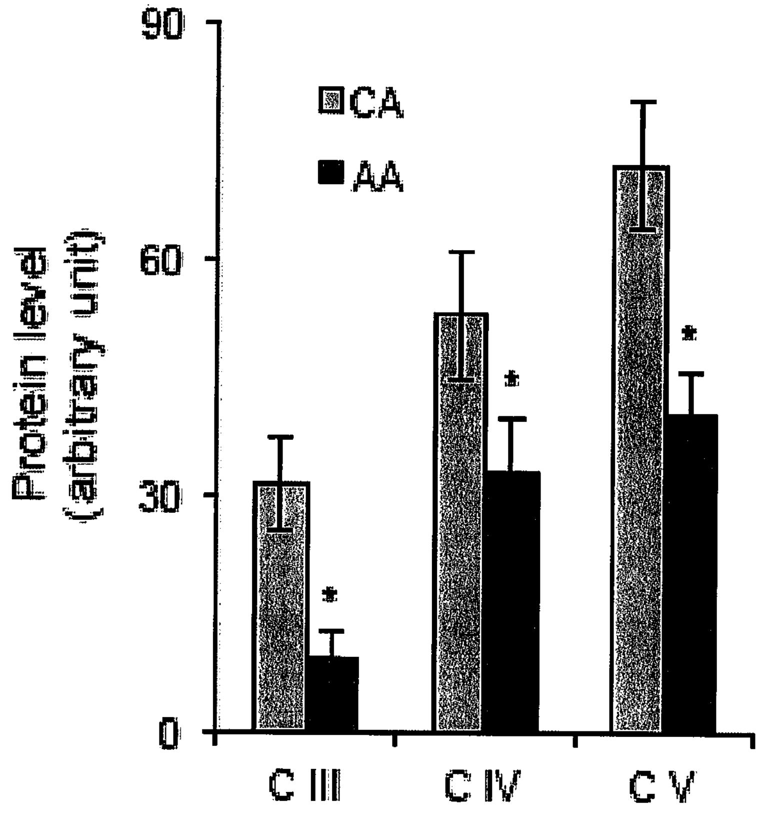
Figure 18A:
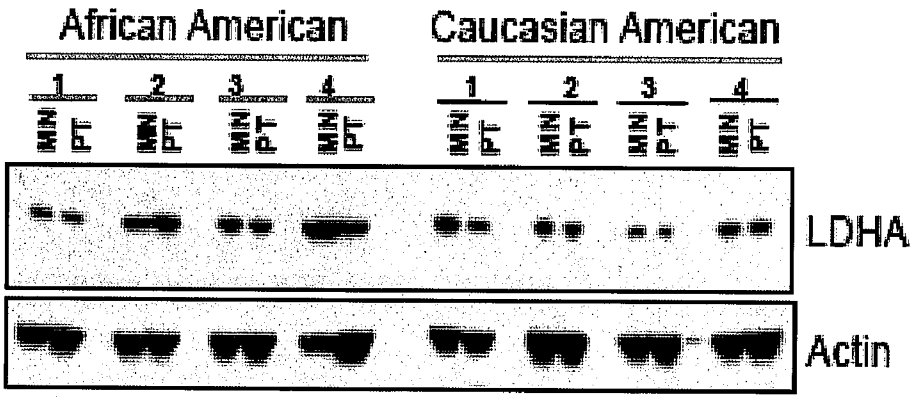
Figure 18B:
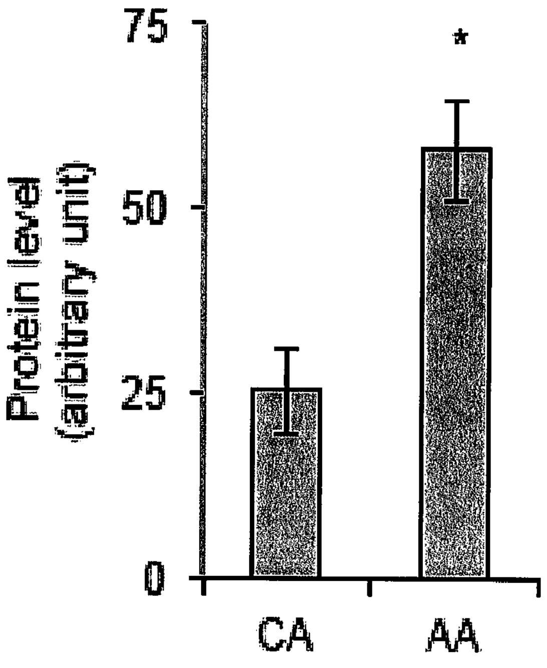

FIGS. 17A-B: FIG. 17A is a representative immunoblot of OXPHOS complex III (C III), complex IV (C IV) and complex V (C V) in matched non-tumor (MN) and primary tumor (PT) tissue samples from AA and CA men with PCa. FIG. 17B is a densitometry analysis of immunoblots of C III, C IV and C V in PT tissues from AA and CA men with PCa (n=12 for each race). Actin serves as a loading control. *p<0.05 vs respective groups FIGS. 18A-B: FIG. 18A is a representative immunoblot of LDHA in matched non-tumor (MN) and primary tumor (PT) tissue samples obtained from AA and CA men with PCa. FIG. 18B is a densitometry analysis of immunoblots of LDHA in PT tissues from AA and CA men with PCa (n=12 for each race). *p<0.05 vs respective group.

IV. DETAILED DESCRIPTION OF THE INVENTION

A first aspect of the present invention is directed to a method of treating prostate cancer in a subject. This method involves selecting a subject having prostate cancer and cytochrome-c deficiency, and administering, to the selected subject, a therapeutically effective amount of one or more agents capable of restoring cytochrome-c activity, thereby treating the prostate cancer.

Prostate cancer is one of the most common cancers in men with an estimated 180,890 new cases in 2016 in the United States. It is a leading cause of death among men who die from neoplasia with an estimated 26,120 deaths per year according to Cancer Statistics, 2016. Prompt detection and treatment is needed to limit mortality caused by prostate cancer.

Prostate cancer is hormone-dependent in its initial stages. Hormonal therapy directed against the androgen receptor (AR) is generally effective; however, failure of therapy is frequent. Prostrate cancer that fails to respond to hormone therapy is referred to as "castration resistant" prostate cancer. The castration resistant form of prostate cancer progresses to end-stage, lethal disease, with very few treatment options available. Chemotherapy is typically used to treat castration resistant cancer; however, many patients are likewise resistant to this form of therapy as well. Approximately 25,000 men die from castration-resistance prostate cancer (CRPC) each year in the US.

Accordingly, in one embodiment, the subject to be treated in accordance with the methods as described herein has a drug resistant form of prostate cancer. As used herein, the term "resistant" or "refractory" refers to a form of prostate cancer that does not respond (i.e., is not sensitive) to treatment with hormone therapy (e.g., anti-androgen therapy) and/or treatment with a chemotherapeutic agent, or is less responsive than a non-resistant prostate cancer cell to treatment with said therapeutic agents. In one embodiment, the drug resistant form of prostate cancer is a form that does not respond to hormone therapy. In one embodiment, the drug resistant form of prostate cancer is a form that does not respond to chemotherapy. The resistance may be de novo resistance, i.e., resistance that exists prior to treatment with a given therapeutic agent, or acquired resistance, i.e., resistance that is acquired after at least one treatment with a given therapeutic agent.

In another embodiment of the present invention, the subject to be treated in accordance with the methods of the present invention is a subject at risk of developing a drug resistant form of prostate cancer, i.e., the patient may be responding to initial therapy but has a cytochrome-c deficiency. Such subjects include patients having early stage prostate cancer, advanced stage prostate cancer, and/or metastatic prostate cancer. In another embodiment, the subject has metastatic prostate cancer that is drug resistant (e.g., anti-androgen drug resistant and/or chemotherapeutic resistant). In another embodiment, the prostate cancer is a recurrent form of prostate cancer.

In accordance with this and all aspects of the present invention, the subject being treating is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

As used herein, "cytochrome-c" refers to a small, mobile molecule that shuttles electrons through the last step of aerobic energy production. However, cytochrome-c is also required for efficient drug-induced apoptosis. Cytochrome-c release from mitochondria interacts with and activates the adapter protein, apoptotic protease-activating factor-1 (Apaf-1), which undergoes oligomerization to form the apoptosome that recruits and activates caspase-9 at the apoptosome complex. Caspase-9 then activates effector caspases, such as caspase-3 to execute apoptosis. As described herein, applicant has found that cytochrome-c deficiency in some prostate cancer patients blocks drug-induced apoptosis, leading to drug resistance.

Thus, as described herein, mitochondrial dysfunction involving the loss of cytochrome-c in prostate tissue contributes to therapeutic resistance and higher aggressiveness of prostate cancer in certain patients. Correction of this cytochrome-c deficiency restores drug-induced apoptosis thereby offering an effective therapeutic approach, especially when used in combination with standard therapeutics, for prostate cancer patients exhibiting aggressive, recurrent, and/or drug resistance disease phenotypes.

As used herein "cytochrome-c deficiency" refers to a decrease in cytochrome-c expression and/or a decrease in cytochrome-c activity. With regard to the latter, a decrease in cytochrome-c activity includes, but is not limited to, a decrease in cytochrome-c release from mitochondria.

Thus, in one embodiment, the one or more agents that restore cytochrome-c activity include an agent that induces cytochrome-c expression. Expression of cytochrome-c in mammalian cells is regulated by peroxisome proliferator-activated receptor gamma coactivator 1-alpha (PGC1-$\alpha$), specificity protein 1 (SP-1), and nuclear respiratory factor 1 (Nrf1) transcription factors.

In one embodiment, an agent that induces cytochrome-c expression is a cellular Myc (c-Myc) inhibitor. C-Myc is one of two factors that regulate Nrf1 nuclear translocation and its target genes. As described herein, enhanced c-Myc activity in prostate cancer cells decreases nuclear translocation of Nrf1 and abrogates its binding to the cytochrome-c promoter to reduce cytochrome-c expression. Suitable c-Myc inhibitors for use in the methods of the present invention to restore nuclear translocation of Nrf1 and transcription of cytochrome-c include those which directly inhibit c-Myc expression. These c-Myc inhibitors include, without limitation, agents that interfere with nucleic acid sequences upstream of the MYC promoter and stabilize G-quadraplex structures, antisense oligonucleotides, small interfering RNAs, and microRNAs.

Exemplary agents that stabilize G-quadraplex structures and inhibit c-Myc include, without limitation, perylene derivatives (e.g., N,N'-bis(2-(1-piperidino)ethyl)-3,4,9,10-perylenetetracarboxylic acid diimide (PIPER)), quindolines (e.g., SYUIQ-05), platinum complexes (e.g., $[Pt(Dp)_2](PF_6)_2$), ellipticine, cationic porphyrins (e.g., $TMPyP_4$, $Se_2SAP$), Hoechst 33258, alkaloids (e.g., sanguinarine, palmatine, tetrahydropalmatine, berberine, 9-substituted berberine, QBDI compounds, daurisoline, O-methydauricine, O-diacetyldaurisokine, daurinoline, dauricholine, and N,N'-dimethylduaricine iodide), carbamide, and CX-3543 (see e.g., Chen et al., "Small Molecules Targeting c-Myc Oncogene: Promising Anti-Cancer Therapeutics," *Int. J. Biol. Sci.* 10:1084-1096 (2014); Whitfield et al., "Strategies to Inhibit Myc and Their Clinical Applicability," *Frontiers in Cell and Dev. Biol.* 5:1-13 (2017), which are hereby incorporated by reference in their entirety).

Exemplary c-Myc antisense oligonucleotides, siRNA, and microRNA inhibitors include, without limitation, INX-3280, AVI-4126, DCR-MYC, siRNA incorporated into nanoparticles, and siRNA in oncolytic viruses as described in Whitfield et al., "Strategies to Inhibit Myc and Their Clinical Applicability," *Frontiers in Cell and Dev. Biol.* 5:1-13 (2017), which is hereby incorporated by reference in its entirety.

Other suitable c-Myc inhibitors include those which interfere with protein-protein interaction (e.g., Myc/Max dimerization) or DNA binding. The carboxyl terminus of MYC encodes a basic helix-loop-helix-leucine-zipper DNA-binding domain. The leucine zipper forms a coiled-coil heterodimer with a homologous region on MAX, which together engage E-box DNA-binding sites. Thus, inhibitors of this Myc/Max interaction or their subsequent DNA binding are contemplated herein.

Exemplary agents that inhibit Myc/Max dimerization and/or DNA binding include, without limitation, IIA6B17, 10058-F4, 10074-G5, 3jc48-3, Mycro3, KJ-Pyr-9, Mycrol, 10074-A4, IIA4B20, KSI-2826, FBN-1503, Mycmycin-1, Mycmycin-2, NY2267, 28RH-HCN-1, JY-3-094, MYRA-A, NSC308848, KSI-3716, Omomyc, H1 peptide, and MI1-PD (see e.g., Chen et al., "Small Molecules Targeting c-Myc Oncogene: Promising Anti-Cancer Therapeutics," *Int. J. Biol. Sci.* 10:1084-1096 (2014); Whitfield et al., "Strategies to Inhibit Myc and Their Clinical Applicability," *Frontiers in Cell and Dev. Biol.* 5:1-13 (2017); Carabet et al., "Therapeutic Inhibition of Myc in Cancer. Structural Bases and Computer-Aided Drug Discovery Approaches," *Int. J. Mol. Sci.* 20:120 (2019), which are hereby incorporated by reference in their entirety).

Agents which indirectly inhibit c-Myc are also contemplated herein. Exemplary agents include, without limitation, BET bromodomain and extra-terminal domain inhibitors (e.g., TEN-010, OTX015, CPI-0160, ABBV-075, INCB054329, GSK525762, JQI, and FT-1101), cyclin-dependent kinase 7 and 9 inhibitors (e.g., THZ1, THZ2, Roscovitine, Flavopiridol, PC585, PHA767491 HCI, SU9516, SNS-032), and mTOR inhibitors (e.g., BEZ235, Rapamycin), all of which are described in Chen et al., "Targeting Oncogenic Myc as a Strategy for Cancer Treatment," *Signal Trans. and Targeted Therapy* 3:5 (2018); Whitfield et al., "Strategies to Inhibit Myc and Their Clinical Applicability," *Frontiers in Cell and Dev. Biol.* 5:1-13 (2017); Carabet et al., "Therapeutic Inhibition of Myc in Cancer. Structural Bases and Computer-Aided Drug Discovery Approaches," *Int. J. Mol. Sci.* 20:120 (2019); McKeown et al., "Therapeutic Strategies to Inhibit MYC," *Cold Spring Harbor Perspectives in Medicine* 4:a014266 (2014), which are hereby incorporated by reference in their entirety.

Further, synthetically lethal agents which target c-Myc are also useful in the methods described herein. By way of example, Aurora kinase, glutaminase, and Cdk-1 are required for cell survival in c-Myc-addicted cancer cells. Thus, inhibition of these molecules is also contemplated and described in Whitfield et al., "Strategies to Inhibit Myc and Their Clinical Applicability," *Frontiers in Cell and Dev. Biol.* 5:1-13 (2017); Carabet et al., "Therapeutic Inhibition of Myc in Cancer. Structural Bases and Computer-Aided Drug Discovery Approaches," *Int. J. Mol. Sci.* 20:120 (2019); Chen et al., "Targeting Oncogenic Myc as a Strategy for Cancer Treatment," *Signal Trans. and Targeted Therapy* 3:5 (2018), which are hereby incorporated by reference in their entirety.

In another embodiment, the agent that induces cytochrome-c expression is an NF-κB inhibitor. NF-κB, like c-Myc, regulates Nrf1 nuclear translocation and its target genes. As described herein, enhanced NF-κB activity in prostate cancer cells decreases nuclear translocation of Nrf1 and abrogates its binding to the cytochrome-c promoter to reduce cytochrome-c expression. Thus, administration of an NF-κB inhibitor restores Nrf1 nuclear translocation and cytochrome-c transcription.

As used herein, an "NF-κB inhibitor" is a substance or substances that interfere with the production and/or the function of NF-κB. In most cells, NF-κB is present as a latent, inactive, IκB-bound complex in the cytoplasm. When a cell receives any of a multitude of extracellular signals, NF-κB rapidly enters the nucleus and activates gene expression including genes involved in inflammation, apoptosis, and cell survival. Therefore, a key step for controlling NF-κB activity is the regulation of the IκB-NF-kB interaction. Almost all signals that lead to activation of NF-kB converge on the activation of a high molecular weight complex that contains a serine-specific IκB kinase (IKK). IKK is an unusual kinase in that in most cells IKK contains (at least) three distinct subunits: IKKalpha, IKKbeta and IKKgamma. IKKα and IKKβ are related catalytic kinase subunits, and IKKγ (aka NEMO) is a regulatory subunit that serves as a sensing scaffold and integrator of upstream signals for activation of the catalytic subunits. In the classical or canonical pathway, activation of IKK complex leads to the phosphorylation by IKKβ of two specific serines near the N terminus of IκBα, which targets IκBα for ubiquitination (generally by a complex called beta-TrCP) and degradation by the 26S proteasome. In the non-canonical (or alternative) pathway, the p100-RelB complex is activated by phosphorylation of the C-terminal region of p100 by an IKKα homodimer (lacking IKKgamma), which leads to ubiquitination followed by degradation of the p100 IκB-like C-terminal sequences to generate p52-RelB. In either pathway, the unmasked NF-κB complex can then enter the nucleus to activate target gene expression. In the classical pathway, one of the target genes activated by NF-κB is that which encodes IκBα. Newly-synthesized IκBα can enter the nucleus, remove NF-κB from DNA, and export the complex back to the cytoplasm to restore the original latent state. Thus, the inhibition of NF-κB can occur at the level of several proteins.

With respect to the methods of the present invention, suitable methods of inhibiting NF-κB include inhibition by protein phosphatases, proteasome inhibitors, IκB ubiquitination blockers, inhibitors of nuclear translocation, inhibitors of NF-κB acetylation, inhibition by methyltransferases, and inhibition of NF-κB binding to DNA. Exemplary agents of these categories that can be utilized in the methods of the present invention are described in Gupta et al., "Inhibiting NF-κB Activation by Small Molecules as a Therapeutic Strategy," Biochem. Biophys. Acta. 1799(10-12):775-787 (2010), which is hereby incorporated by reference in its entirety. By way of example, cytosine arabinoside and phenylarsine oxide inhibit NF-κB via the action of phosphatases; bortezomib, ALLnL, LLM, Z-LLnV, Z-LLL, lactacystine, N-cbz-Leu-Leu-leucinal (MG132), and MG115 inhibit NF-id3 via proteasome or IκB ubiquitination inhibition; SN50 and dehydroxymethylepoxyquinomicin inhibit nuclear translocation of NF-κB; gallic acid, anacardic acid, and Daxx protein inhibit NFκB acetylation; and sesquiterpene lactones and decoy oligonucleotides inhibit NF-κB binding to DNA. Any one or more of these agents can be administered to a subject having prostate cancer and cytochrome-c deficiency as described herein.

Additional agents for inhibiting NF-κB that are suitable for administration to a subject in accordance with the methods described herein include, without limitation, antioxidants, bacterial proteins, fungal protein, viral proteins, anti-inflammatory agents, immunosuppressive agents as described in Gupta et al., "Inhibiting NF-κB Activation by Small Molecules as a Therapeutic Strategy," Biochem. Biophys. Acta. 1799(10-12):775-787 (2010), which is hereby incorporated by reference in its entirety.

In another embodiment, the agent that induces cytochrome-c expression is an Akt1 inhibitor. Akt1 (also known as Protein kinase B) is involved in a signal transduction pathway that promotes survival and growth in response to extracellular signals. Akt1 is a serine/threonine kinase that is involved in, among other things, phosphoactivation of Nrf1 and its target genes. As described herein, the level of active AKT (p-Akt1$^{S473}$) is reduced in prostate cancer cells, which abrogates Nrf1-mediated cytochrome-c expression. Thus, in another embodiment of the present invention, a suitable agent for restoring cytochrome-c expression is an agent that activates Akt1. A suitable agent that activates Akt1, is an agent phosphorylates Akt1 (e.g., an Akt1 kinase) or prevents Akt1 dephosphorylation (e.g. an Akt1 phosphatase inhibitor), particularly at serine residue 473 of Akt1. Thus, in one embodiment, the Akt1 activator is an inhibitor of PTEN (i.e., phosphatase and tensin homolog), an Akt1 phosphatase.

Inhibition of PTEN can involve regulation of PTEN expression levels, protein conformation, and subcellular localization. By way of example, vanadium and peroxovanadium compounds are general inhibitors of protein tyrosine phosphatases. Other exemplary PEEN inhibitors include, bisperoxovanadium compounds, including bpV(phen) (bisperoxovanadium 1,10-phenantroline), bpV(pic) (bisperoxovanadium 5-hydroxipyridine), bpV(HOpic) (bisperoxovanadium 5-hydroxipyridine-2-carboxylic acid), bpV(pis) (bisperoxovanadium pyridin-2-squaramide), as well as the related vanadium complex V(HOpic) (hydroxyl(oxo)vanadium 3-hydroxypiridine-2-carboxylic acid) (see e.g., Pulido, "PTEN Inhibition in Human Disease Therapy," *Molecules* 23:285 (2018), which is hereby incorporated by reference in its entirety). A phenanthrenedione-related compound, SF1670 (N-(9,10-dioxo-9,10-dihydrophenanthren-2-yl) pivalamide), is also relatively specific PTEN inhibitor (see e.g., Pulido, "PTEN Inhibition in Human Disease Therapy," *Molecules* 23:285 (2018), which is hereby incorporated by reference in its entirety).

In another embodiment of the present invention, the one or more agents that alleviate cytochrome-c deficiency include an agent that induces cytochrome-c release from the mitochondria membrane. As described herein, a decrease in cytochrome-c release from the mitochondria membrane in some prostate cancer cells is associated with an increase in the inhibitory form of dynamin-related protein (Drp1), i.e., Drp1 having a phosphoserine residue at serine 632, which inhibits mitochondrial fission. In contrast, phosphorylation of Drp1 at serine 616 (p-Drp1$^{S616}$) is associated with cytochrome-c release and promoting mitochondrial fission and cell death. Thus, in one embodiment, a suitable agent for inducing cytochrome-c release from mitochondria is an agent that enhances Drp1$^{S616}$ phosphorylation (i.e., a Drp1 kinase) or an agent that reduces Drp1$^{S637}$ phosphorylation (i.e., a Drp1 phosphatase). As shown herein activated Akt1 (i.e., pAkt-1) promotes Drp1 phosphorylation at serine 616. Therefore, in one embodiment, an agent suitable for inducing cytochrome-c release is a PTEN inhibitor as described above.

In one embodiment of the present invention, one or more chemotherapeutic drugs are administered to the subject having prostate cancer and cytochrome-c deficiency in combination with the one or more agents capable of restoring cytochrome-c activity. Suitable chemotherapeutic drugs include, without limitation, taxane derivatives (e.g., docetaxel, cabazitaxel, mitoxantrone, and estramustine), alkylating agents (e.g., chlorambucil, cyclophosphamide, CCNU, melphalan, procarbazine, thiotepa, BCNU, carboplatin, and busulfan), antimetabolites (e.g., methotraxate, 6-mercaptopurine, gemcitabine, capecitabine and 5-fluorouracil), anthracyclines (daunorubicin, doxorubicin, idarubicin, epirubicin, and mitoxantrone), antitumor antibiotics (e.g., mitoxantrone, bleomycin, monoclonal antibodies (e.g., Alemtuzumab, Bevacizumab, Cetuximab, Gemtuzumab, Ibritumomab, Panitumumab, Rituximab, Tositumomab, and Trastuxmab), platiniums (e.g., cisplatin and oxaliplatin), antimicrotubular (e.g., eribulin, ixabepilone, vinorelbine, docetaxel, vincristine), antineoplastic (Mutamycin, estramucine), or plant alkaloids (e.g., topoisomerase inhibitors, *vinca* alkaloids, and epipodophyllotoxin. The chemotherapeutic agent may be selected from the group consisting of docetaxel, cabazitaxel, mitoxantrone, and estramustine. The chemotherapeutic agent may also be administered with a glycolytic inhibitor such as 3-bromopyruvate (3-BrPA)

In one embodiment the one or more agents capable of restoring cytochrome-c deficiency and the one or more chemotherapeutic drugs are administered simultaneously. In another embodiment, the one or more agents capable of restoring cytochrome-c deficiency and the one or more chemotherapeutic drugs are administered sequentially. For example, the one or more agents capable of restoring cytochrome-c deficiency are administered prior to administering the one or more chemotherapeutic drugs. The time between administering the agent(s) for restoring cytochrome-c deficiency and the chemotherapeutic drug(s) can be on the order of hours, days, or weeks. The optimal duration of time between the sequential administrations may vary depending on the subject and can be readily determined by a skilled physician.

In accordance with this aspect of the present invention, the method of treating a subject having prostate cancer may further involve measuring one or more of the levels of cytochrome-c expression and/or activity (e.g., cytochrome-c release from the mitochondria), c-Myc expression or activity, NF-κB expression or activity, Akt1 activity and/or phosphorylation, and Drp1 phosphorylation level and/or status. Methods of measuring such levels are known in the art and described herein. The outcome of one or more of these measurements will guide the selection of the appropriate agent to administer to the subject for the purpose of restoring a cytochrome-c deficiency.

Another aspect of the present invention relates to a method of inducing apoptosis in drug resistant cancer cells. This method involves selecting drug resistant cancer cells having cytochrome-c deficiency and administering, to the selected cells, one or more agents that restore cytochrome-c activity in an amount effective to sensitize the cancer cells to drug induced apoptosis.

As described supra, a drug resistant cancer cell is one that does not respond (e.g., is not sensitive) to treatment with a chemotherapeutic agent, hormone therapy, or other apoptosis-inducing therapy, or is less responsive than a non-resistant cancer cell to treatment with the aforementioned therapeutic agents. In one embodiment, the cancer cells are resistant to apoptosis induced by chemotherapy. In another embodiment, the cancer cells are resistant to apoptosis induced to hormonal therapy. In another embodiment, the cancer cells are resistant to apoptosis induced by another anti-cancer therapeutic.

Virtually any cancer cells having a cytochrome-c deficiency can develop a resistance to drug-induced apoptosis, including, but not limited to prostate cancer cells, acute lymphoblastic leukemia cells, acute myeloid leukemia cells, adrenocortical carcinoma cells, anal cancer cells, appendix cancer cells, astrocytoma (childhood cerebellar or cerebral) cells, basal-cell carcinoma cells, bile duct cancer cells, bladder cancer cells, bone tumor cells, osteosarcoma/malignant fibrous histiocytoma cells, brain stem glioma cells, ependymoma cells, medulloblastoma cells, breast cancer cells, bronchial adenomas/carcinoids cells, Burkitt's lymphoma cells, carcinoid tumor cells, cervical cancer cells, childhood cancers cells, chondrosarcoma cells, chronic lymphocytic leukemia cells, chronic myelogenous leukemia cells, chronic myeloproliferative disorders cells, colon cancer cells, cutaneous T-cell lymphoma cells, desmoplastic small round cell tumor cells, endometrial cancer cells, esophageal cancer cells, Ewing's sarcoma cells, retinoblastoma cells, gallbladder cancer cells, gastric (stomach) cancer cells, gastrointestinal stromal tumor (GIST) cells, germ cell tumor cells, gestational trophoblastic tumor cells, hairy cell leukemia cells, head and neck cancer cells, heart cancer cells, hepatocellular (liver) cancer cells, Hodgkin lymphoma cells, hypopharyngeal cancer cells, islet cell carcinoma (endocrine pancreas) cells, Kaposi sarcoma cells, kidney cancer (renal cell cancer) cells, laryngeal cancer cells, lip and oral cavity cancer cells, non-small cell lung cancer cells, small cell lung cancer cells, lymphoma cells, cutaneous T-Cell lymphoma cells, melanoma cells, Merkel cell cancer cells, mesothelioma cells, multiple endocrine neoplasia syndrome cells, multiple myeloma cells, myelodysplastic/myeloproliferative disease cells, multiple myeloma cells, chronic myeloproliferative disorder cells, nasopharyngeal carcinoma cells, neuroblastoma cells, oligodendroglioma cells, oral cancer cells, oropharyngeal cancer cells, ovarian cancer cells, pancreatic cancer cells, pleuropulmonary blastoma cells, primary central nervous system lymphoma cells, retinoblastoma cells, rhabdomyosarcoma cells, salivary gland cancer cells, soft tissue sarcoma cells, uterine sarcoma cells, Sezary syndrome cells, skin cancer (non-melanoma) cells, small intestine cancer cells, squamous cell carcinoma cells, stomach cancer cells, T-Cell lymphoma (cutaneous) cells, testicular cancer cells, throat cancer cells, thymoma and thymic carcinoma cells, thyroid cancer cells, trophoblastic tumor cells, urethral cancer cells, and uterine cancer (endometrial) cells.

As described supra, agents that restore cytochrome-c activity that are suitable for use in accordance with this aspect of the invention include, without limitation, c-Myc inhibitors, NF-κB inhibitors, Akt1 activating agent, and Drp1 kinase. In accordance with this aspect of the present invention, an amount effect to "sensitize" the cancer cells to drug induced apoptosis refers to an amount of the one or more agents that restore cytochrome-c activity to a level that increases the sensitivity of the cancer cells to drug induced apoptosis. Induction of cancer cell apoptosis includes, but is not limited to, increased levels of cancer cell death as compared to the death of untreated or mock treated cells.

For example, the methods described herein increase the sensitivity of cancer cells to drug induced apoptosis (e.g., via one or more chemotherapeutic agents described herein) by at least 1%, 2%, 3%, 4%, 5%, 6%, 7%, 8%, 9%, 10%, 20%, 30%, 40%, 50%, 60%, 70%, 80%, 90%, 95%, 99%, or 100%, or more, as compared to when the one or more agents that restore cytochrome-c activity are not administered. An increase in sensitivity to drug induced apoptosis may be measured by, e.g., caspase-3 activation levels, PARP cleavage levels, cytochrome-c levels, and cell death.

In certain embodiments, administering one or more agents that restore cytochrome-c activity as described herein is effective to increase chemotherapeutic sensitivity to chemotherapeutic resistant cells having de novo resistance or acquired resistance. In some embodiments, the methods described herein may further involve administering one or more apoptosis inducing drugs, e.g., a chemotherapeutic agent, in combination with the agent(s) that restore cytochrome-c deficiency to the selected cells.

The method of increasing sensitivity of cancer cells to drug induced apoptosis can be carried out in vitro, in vivo, or ex vivo. When methods described herein are carried out in vivo, selecting drug resistant cancer cells may involve selecting a subject having a drug resistant form of cancer and a cytochrome-c deficiency and administering the one or more agents that restore cytochrome-c activity as described herein to the selected subject.

Another aspect of the present invention relates to a combination therapy that includes one or more agents that restore cytochrome-c activity as described herein and a chemotherapeutic agent as described herein.

As used herein, the term "combination therapy" refers to the administration of two or more therapeutic agents, i.e., one or more agents that restore cytochrome-c activity in combination with a chemotherapeutic agent, suitable for the treatment of a resistant form of cancer, such as a resistant form of prostate cancer. The combination therapy can be co-administered in a substantially simultaneous manner, such as in a single capsule or other delivery vehicle having a fixed ratio of active ingredients, or in multiple capsules or delivery vehicles, each containing an active ingredient. In addition, such administration also encompasses use of each type of therapeutic agent in a sequential manner, either at approximately the same time or at different times. In either case, the treatment regimen will provide beneficial effects of the drug combination in treating resistant forms of cancer.

In one embodiment, the combination therapeutic encompasses the one or more agents that restore cytochrome-c activity (i.e., c-myc inhibitors, NF-κB inhibitors, Akt1 activating agents, and Drp1 kinases as described supra) and the chemotherapeutic agent(s) formulated separately, but for administration in combination. In another embodiment, the combination therapeutic encompasses the one or more agents that restore cytochrome-c activity and the chemotherapeutic agent(s) formulated together in a single formulation. A single formulation refers to a single carrier or vehicle formulated to deliver effective amounts of both therapeutic agents in a unit dose to a patient. The single vehicle is designed to deliver an effective amount of each of the agents, along with any pharmaceutically acceptable carriers or excipients. In some embodiments, the vehicle is a tablet, capsule, pill, or a patch. In other embodiments, the vehicle is a solution or a suspension. In yet another embodiment, the vehicle is a nanodelivery vehicle.

Suitable nanodelivery vehicles for the delivery of cancer therapeutics, such as those described herein, are known in the art and include, for example and without limitation, nanoparticles such as albumin particles (Hawkins et al., "Protein nanoparticles as drug carriers in clinical medicine," *Advanced Drug Delivery Reviews* 60(8): 876-885 (2008), which is hereby incorporated by reference in its entirety), cationic bovine serum albumin nanoparticles (Han et al., "Cationic bovine serum albumin based self-assembled nanoparticles as siRNA delivery vector for treating lung metastasis cancer," *Small* 10(3): (2013), which is hereby incorporated by reference in its entirety), gelatin nanoparticles (Babaei et al., "Fabrication and evaluation of gelatine nanoparticles for delivering of anti-cancer drug," *Int'l J. NanoSci. Nanotech.* 4:23-29 (2008), which is hereby incorporated by reference in its entirety), gliadin nanoparticles (Gulfam et al., "Anticancer drug-loaded gliadin nanoparticles induced apoptosis in breast cancer cells," *Langmuir* 28: 8216-8223 (2012), which is hereby incorporated by reference in its entirety), zein nanoparticles (Aswathy et al., "Biocompatible fluorescent zein nanoparticles for simultaneous bioimaging and drug delivery application," *Advances in Natural Sciences: Nanoscience and Nanotechnology* 3(2) (2012), which is hereby incorporated by reference in its entirety), and casein nanoparticles (Elzoghby et al., "Ionically-crosslinked milk protein nanoparticles as flutamide carriers for effective anticancer activity in prostate cancer-bearing rats," *Eur. J. Pharm. Biopharm.* 85(3): 444-451 (2013) which is hereby incorporated by reference in its entirety); liposomes (Feldman et al., "First-in-man study of CPX-351: a liposomal carrier containing cytarabine and daunorubicin in a fixed 5:1 molar ratio for the treatment of relapsed and refractory acute myeloid leukemia," *J. Clin. Oncol.* 29(8): 979-985 (2011); Ong et al., "Development of stealth liposome coencapsulating doxorubicin and fluoxetine," *J. Liposome Res.* 21(4): 261-271 (2011); and Sawant et al., "Palmitoyl ascorbate-modified liposomes as nanoparticle platform for ascorbate-mediated cytotoxicity and paclitaxel co-delivery," *Eur. J. Pharm. Biopharm.* 75(3): 321-326 (2010), which are hereby incorporated by reference in their entirety); polymeric nanoparticles, including synthetic polymers, such as poly-ε-caprolactone, polyacrylamine, and polyacrylate, and natural polymers, such as, e.g., albumin, gelatin, or chitosan (Agnihotri et al., "Novel interpenetrating network chitosan-poly(ethylene oxide-g-acrylamide)hydrogel microspheres for the controlled release of capecitabine," *Int J Pharm* 324: 103-115 (2006); Bilensoy et al., "Intravesical cationic nanoparticles of chitosan and polycaprolactone for the delivery of Mitomycin C to bladder tumor," *Int J Pharm* 371: 170-176 (2009), which are hereby incorporated by reference); dendrimer nanocarriers (e.g., poly(amido amide) (PAMAM)) (Han et al., "Peptide conjugated PAMAM for targeted doxorubicin delivery to transferrin receptor overexpressed tumors," *Mol Pharm* 7: 2156-2165 (2010); and Singh et al., "Folate and Folate-PEG-PAMAM dendrimers: synthesis, characterization, and targeted anticancer drug delivery potential in tumor bearing mice," *Bioconjugate Chem* 19, 2239-2252 (2008), which are hereby incorporated by reference in their entirety); silica nanoparticle (e.g., xerogels and mesoporous silica nanoparticles) (He et al., "A pH-responsive mesoporous silica nanoparticles based multi-drug delivery system for overcoming multidrug resistance," *Biomaterials* 32: 7711-7720 (2011); Prokopowicz M., "Synthesis and in vitro characterization of freeze-dried doxorubicin-loaded silica xerogels," *J Sol-Gel Sci Technol* 53: 525-533 (2010); Mayer et al., "Novel hybrid silica xerogels for stabilization and controlled release of drug," *Int J Pharm* 330:164-174 (2007), which are hereby incorporated by reference in their entirety).

The nanodelivery vehicles described herein can be surface modified to express or display an antibody or other binding molecule having binding specificity for a tumor-specific antigen or receptor, or a ligand that binds to a tumor-specific cell surface receptor. For administration to a subject having prostate cancer, the nanodelivery vehicles can be surface modified to express ligands that interact with prostate-specific membrane antigen (PSMA) such as described in Autio et al., "Safety and Efficacy of BIND-014, a Docetaxel Nanoparticle Targeting Prostate-Specific Membrane Antigen for Patients With Metastatic Castration-Resistant Prostate Cancer: A Phase 2 Clinical Trial," *JAMA Oncol.* 4(10): 1344-1351 (2018), which is hereby incorporated by reference in its entirety. Other exemplary epitopes on cancer-cell surfaces that can be targeted via an antibody or other binding molecule on the surface of a delivery vehicle include, without limitation, epidermal growth factor receptor (EGFR), the folate receptor, the transferrin receptor (CD71), ErbB2, and the carcinoembryonic antigen (CEA), and integrins. Other exemplary tumor specific targets include components that are involved in the degradation of the extracellular matrix of the tumor interstitium, e.g., matrix metalloproteases (MMPs).

The therapeutic agents and combination therapeutics for use in the methods described herein can be formulated into a pharmaceutical composition as any one or more of the active compounds described herein and a physiologically acceptable carrier (also referred to as a pharmaceutically acceptable carrier or solution or diluent). Such carriers and solutions include pharmaceutically acceptable salts and solvates of compounds used in the methods described herein, and mixtures comprising two or more of such compounds, pharmaceutically acceptable salts of the compounds and pharmaceutically acceptable solvates of the compounds. Such compositions are prepared in accordance with acceptable pharmaceutical procedures such as described in Remington: The Science and Practice of Pharmacy, 20th edition, ed. Alfonso R. Gennaro (2000), which is incorporated herein by reference in its entirety.

The term "pharmaceutically acceptable carrier" refers to a carrier that does not cause an allergic reaction or other untoward effect in patients to whom it is administered and are compatible with the other ingredients in the formulation. Pharmaceutically acceptable carriers include, for example, pharmaceutical diluents, excipients or carriers suitably selected with respect to the intended form of administration, and consistent with conventional pharmaceutical practices. For example, solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof. Pharmaceutically acceptable carriers may further comprise minor amounts of auxiliary substances such as wetting or emulsifying agents, preservatives or buffers, which enhance the shelf life or effectiveness of the therapeutic agent.

Reference to therapeutic agents described herein includes any analog, derivative, isomer, metabolite, pharmaceutically acceptable salt, pharmaceutical product, hydrate, N-oxide, crystal, polymorph, prodrug or any combination thereof. In certain embodiments, the therapeutic agents disclosed herein may be in a prodrug form, meaning that it must undergo some alteration (e.g., oxidation or hydrolysis) to achieve its active form.

The therapeutic agents in a free form can be converted into a salt, if need be, by conventional methods. The term "salt" used herein is not limited as long as the salt is pharmacologically acceptable; preferred examples of salts include a hydrohalide salt (for instance, hydrochloride, hydrobromide, hydroiodide and the like), an inorganic acid salt (for instance, sulfate, nitrate, perchlorate, phosphate, carbonate, bicarbonate and the like), an organic carboxylate salt (for instance, acetate salt, maleate salt, tartrate salt, fumarate salt, citrate salt and the like), an organic sulfonate salt (for instance, methanesulfonate salt, ethanesulfonate salt, benzenesulfonate salt, toluenesulfonate salt, camphorsulfonate salt and the like), an amino acid salt (for instance, aspartate salt, glutamate salt and the like), a quaternary ammonium salt, an alkaline metal salt (for instance, sodium salt, potassium salt and the like), an alkaline earth metal salt (magnesium salt, calcium salt and the like) and the like. In addition, hydrochloride salt, sulfate salt, methanesulfonate salt, acetate salt and the like are preferred as "pharmacologically acceptable salt" of the compounds disclosed herein.

In accordance with the methods described herein, administration of the one or more agents capable of restoring cytochrome-c activity is carried out by systemic or local administration. Suitable modes of systemic administration of the therapeutic agents and/or combination therapeutics disclosed herein include, without limitation, orally, topically, transdermally, parenterally, intradermally, intrapulmonary, intramuscularly, intraperitoneally, intravenously, subcutaneously, or by intranasal instillation, by intracavitary or intravesical instillation, intraocularly, intra-arterially, intralesionally, or by application to mucous membranes. In certain embodiments, the therapeutic agents of the methods described herein are delivered orally. Suitable modes of local administration of the therapeutic agents and/or combinations disclosed herein include, without limitation, catheterization, implantation, direct injection, dermal/transdermal application, or portal vein administration to relevant tissues, or by any other local administration technique, method or procedure generally known in the art. The mode of affecting delivery of agent will vary depending on the type of therapeutic agent and the type of prostate cancer to be treated.

A therapeutically effective amount of the one or more agents capable of restoring cytochrome-c activity or a combination therapy (e.g., one or more agents capable of restoring cytochrome-c activity and a chemotherapeutic) in the methods disclosed herein is an amount that, when administered over a particular time interval, results in achievement of one or more therapeutic benchmarks (e.g., slowing or halting of tumor growth, resulting in tumor regression, cessation of symptoms, etc.). The therapeutic agents or combinations thereof for use in the presently disclosed methods may be administered to a subject one time or multiple times. In those embodiments where the compounds are administered multiple times, they may be administered at a set interval, e.g., daily, every other day, weekly, or monthly. Alternatively, they can be administered at an irregular interval, for example on an as-needed basis based on symptoms, patient health, and the like. For example, a therapeutically effective amount may be administered once a day (q.d.) for one day, at least 2 days, at least 3 days, at least 4 days, at least 5 days, at least 6 days, at least 7 days, at least 10 days, or at least 15 days. Optionally, the status of the cancer or the regression of the cancer is monitored during or after the treatment, for example, by a multiparametric ultrasound (mpUS), multiparametric magnetic resonance imaging (mpMRI), and nuclear imaging (positron emission tomography [PET]) of the subject. The dosage of the therapeutic agent(s) or combination therapy administered to the subject can be increased or decreased depending on the status of the cancer or the regression of the cancer detected.

The skilled artisan can readily determine this amount, on either an individual subject basis (e.g., the amount of a compound necessary to achieve a particular therapeutic benchmark in the subject being treated) or a population basis (e.g., the amount of a compound necessary to achieve a particular therapeutic benchmark in the average subject from a given population). Ideally, the therapeutically effective amount does not exceed the maximum tolerated dosage at which 50% or more of treated subjects experience nausea, hirsutism, voice hoarsening or other more serious reactions that prevent further drug administrations.

A therapeutically effective amount may vary for a subject depending on a variety of factors, including variety and extent of the symptoms, sex, age, body weight, or general health of the subject, administration mode and salt or solvate type, variation in susceptibility to the drug, the specific type of the disease, and the like.

The effectiveness of the methods of the present application in increasing sensitivity to drug induced apoptosis and/or treating prostate cancer may be evaluated, for example, by assessing changes in tumor burden and/or disease progression following treatment with the one or more therapeutic agents described herein according to the Response Evaluation Criteria in Solid Tumours (Eisenhauer et al., "New Response Evaluation Criteria in Solid Tumours: Revised RECIST Guideline (Version 1.1)," Eur. 1 Cancer 45(2): 228-247 (2009), which is hereby incorporated by reference in its entirety). In some embodiments, tumor burden and/or disease progression is evaluated using imaging techniques including, e.g., X-ray, computed tomography (CT) scan, magnetic resonance imaging, multiparametric ultrasound (mpUS), multiparametric magnetic resonance imaging (mpMRI), and nuclear imaging (positron emission tomography [PET]) (Eisenhauer et al., "New Response Evaluation Criteria in Solid Tumours: Revised RECIST Guideline (Version 1.1)," *Eur. J. Cancer* 45(2): 228-247 (2009), which is hereby incorporated by reference in its entirety). Cancer regression or progression may be monitored prior to, during, and/or following treatment with one or more of the therapeutic agents described herein.

In some embodiments, the response to treatment with the methods described herein results in at least about 1%, 2%, 3%, 4%, 5%, 6%, 7%, 8%, 9%, 10%, 20%, 30%, 40%, 50%, 60%, 70%, 80%, 90%, 95%, 99%, or 100% decrease in tumor size as compared to baseline tumor size. Thus, the response to treatment with any of the methods described herein may be partial (e.g., at least a 30% decrease in tumor size, as compared to baseline tumor size) or complete (elimination of the tumor).

In some embodiments, the effectiveness of the methods described herein may be evaluated, for example, by assessing drug induced apoptosis and/or cell cycle progression in cancer cells following treatment with the one or more agents that restore cytochrome-c activity.

In some embodiments, the methods described herein may be effective to inhibit disease progression, inhibit tumor growth, reduce primary tumor size, relieve tumor-related symptoms, inhibit tumor-secreted factors (e.g., tumor-secreted hormones), delay the appearance of primary or secondary cancer tumors, slow development of primary or secondary cancer tumors, decrease the occurrence of primary or secondary cancer tumors, slow or decrease the severity of secondary effects of disease, arrest tumor growth, and/or achieve regression of cancer in a selected subject. Thus, the methods described herein are effective to increase the therapeutic benefit to the selected subject.

In some embodiments, the methods described herein reduce the rate of tumor growth in the selected subject by at least about 1%, 2%, 3%, 4%, 5%, 6%, 7%, 8%, 9%, 10%, 20%, 30%, 40%, 50%, 60%, 70%, 80%, 90%, 95%, 99%, or more. In certain embodiments, the methods described herein reduce the rate of tumor invasiveness in the selected subject by at least about 1%, 2%, 3%, 4%, 5%, 6%, 7%, 8%, 9%, 10%, 20%, 30%, 40%, 50%, 60%, 70%, 80%, 90%, 95%, 99%, or more. In specific embodiments, the methods described herein reduce the rate of tumor progression in the selected subject by at least about 1%, 2%, 3%, 4%, 5%, 6%, 7%, 8%, 9%, 10%, 20%, 30%, 40%, 50%, 60%, 70%, 80%, 90%, 95%, 99%, or more. In various embodiments, the methods described herein reduce the rate of tumor recurrence in the selected subject by at least about 1%, 2%, 3%, 4%, 5%, 6%, 7%, 8%, 9%, 10%, 20%, 30%, 40%, 50%, 60%, 70%, 80%, 90%, 95%, 99%, or more. In some embodiments, the methods described herein reduce the rate of metastasis in the selected subject by at least about 1%, 2%, 3%, 4%, 5%, 6%, 7%, 8%, 9%, 10%, 20%, 30%, 40%, 50%, 60%, 70%, 80%, 90%, 95%, 99%, or more.

Another aspect of the present invention relates to a method that involves selecting a subject having prostate cancer or another form of cancer, obtaining a cell sample from the selected subject, and measuring cytochrome-c expression levels and Drp1 phosphorylation levels in the sample. In accordance with this aspect of the present invention, the method may further involved measuring the expression level and/or activity of c-Myc in the cell sample, the expression level and/or activity of NF-κB in the cell sample, activity and/or phosphorylation status of Akt1 in the cell sample, and activity and/or phosphorylation status of Drp1 in the cell sample. Suitable samples for carrying out the method in accordance with this aspect of the invention include, without limitation, a tissue sample, including a tumor tissue sample, a cell sample, including a cancer cell sample, a serum sample, a plasma sample, a blood sample, and an exosome sample.

In one embodiment of this aspect of the present invention, the method is carried out on a prostate cell sample obtained from a subject having prostate cancer. In another embodiment, the method is carried out on a prostate cancer cell sample obtain from the subject having prostate cancer. In another embodiment, the method is carried out on a cancer cell sample (or tissue matched normal cell sample) obtained from a subject having another form of cancer, e.g., any of the cancers described supra.

As used herein "measuring" involves, for example, contacting the sample with one or more reagents suitable for detecting and measuring cytochrome-c, c-Myc, and/or NF-κB protein and/or RNA levels, and/or contacting the sample with one or more reagents suitable for detecting and measuring Drp1 and/or Akt1 phosphorylation levels.

As described herein, measurement of cytochrome-c, c-Myc, and/or NF-κB can be achieved by measuring any suitable value that is representative of the gene expression level. The measurement of gene expression levels can be direct or indirect. A direct measurement involves measuring the level or quantity of RNA or protein. An indirect measurement may involve measuring the level or quantity of cDNA, amplified RNA, DNA, or protein; the activity level of RNA or protein; or the level or activity of other molecules (e.g. a metabolite) that are indicative of the foregoing. The measurement of expression can be a measurement of the absolute quantity of a gene product. The measurement can also be a value representative of the absolute quantity, a normalized value (e.g., a quantity of gene product normalized against the quantity of a reference gene product), an averaged value (e.g., average quantity obtained at different time points or from different sample from a subject, or average quantity obtained using different probes, etc.), or a combination thereof.

In one embodiment, the method described herein involves measuring RNA expression level of cytochrome-c, c-Myc, NF-κB individually or in combination. Measuring gene expression by quantifying mRNA expression can be achieved using any method known in the art including northern blotting and in situ hybridization (Parker et al., "mRNA: Detection by in Situ and Northern Hybridization," *Methods in Molecular Biology* 106:247-283 (1999), which is hereby incorporated by reference in its entirety); an RNAse protection assay (Hod et al., "A Simplified Ribonuclease Protection Assay," *Biotechniques* 13:852-854 (1992), which is hereby incorporated by reference in its entirety); reverse transcription polymerase chain reaction (RT-PCR) (Weis et al., "Detection of Rare mRNAs via Quantitative RT-PCR," *Trends in Genetics* 8:263-264 (1992), which is hereby incorporated by reference in its entirety); and serial analysis of gene expression (SAGE) (Velculescu et al., "Serial Analysis of Gene Expression," Science 270:484-487 (1995); and Velculescu et al., "Characterization of the Yeast Transcriptome," Cell 88:243-51 (1997), which is hereby incorporated by reference in its entirety).

In a nucleic acid hybridization assay, the expression level of nucleic acids corresponding to cytochrome-c, c-Myc, and/or NFκB can be detected using an array-based technique (e.g., a microarray or expression chip as described in the art, see e.g., U.S. Pat. No. 5,143,854 to Pirrung et al.; U.S. Pat. No. 5,445,934 to Fodor et al.; U.S. Pat. No. 5,744,305 to Fodor et al.; U.S. Pat. No. 5,677,195 to Winkler et al.; U.S. Pat. No. 6,040,193 to Winkler et al.; U.S. Pat. No. 5,424,186 to Fodor et al., which are all hereby incorporated by reference in their entirety). A microarray comprises an assembly of distinct polynucleotide or oligonucleotide probes immobilized at defined positions on a substrate. Arrays are formed on substrates fabricated with materials such as paper, glass, plastic (e.g., polypropylene, nylon), polyacrylamide, nitrocellulose, silicon, optical fiber or any other suitable solid or semi-solid support, and configured in a planar (e.g., glass plates, silicon chips) or three-dimensional (e.g., pins, fibers, beads, particles, microtiter wells, capillaries) configuration. The probe molecules are generally nucleic acids such as DNA, RNA, PNA, and cDNA.

In another embodiment, the RNA of a cell sample to be analyzed, e.g., a prostate or other cancer cell sample, can be converted into fluorescently labeled cDNA for hybridization to the array. Generation of the fluorescently labeled cDNA involves incorporation of fluorescent nucleotides by reverse transcription of RNA extracted from the cell sample. Labeled cDNA applied to the array hybridizes with specificity to each nucleic acid probe spotted on the array. After stringent washing to remove non-specifically bound cDNA, the array is scanned by confocal laser microscopy or by another detection method, such as a CCD camera. Quantitation of hybridization of each arrayed element allows for assessment of corresponding mRNA abundance. Such methods have been shown to have the sensitivity required to detect rare transcripts, which are expressed at a few copies per cell, and to reproducibly detect at least approximately two-fold differences in the expression levels (Schena et al., "Parallel Human Genome Analysis: Microarray-Based Expression Monitoring of 1000 Genes," "*Proc. Natl. Acad. Sci. USA* 93(20):10614-9 (1996), which is hereby incorporated by reference in its entirety).

A nucleic acid amplification assay that is a semi-quantitative or quantitative real-time polymerase chain reaction (RT-PCR) assay can also be performed. Because RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukemia virus reverse transcriptase (MLV-RT), although others are also known and suitable for this purpose. The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. An exemplary quantitative PCR amplification system using Taq polymerase that can be employed in the detection and quantitation of c-Myc, NF-κB, or cytochrome-c expression levels as described herein is TaqMan® PCR (Applied Biosystems, Foster City, Calif.). TaqMan® RT-PCR can be performed using commercially available equipment, such as, for example, the ABI PRISM 7700® Sequence Detection System® (Perkin-Elmer-Applied Biosystems, Foster City, Calif., USA), or the Lightcycler (Roche Molecular Biochemicals, Mannheim, Germany).

In addition to the TaqMan® primer/probe system, other quantitative methods and reagents for real-time PCR detection that are known in the art (e.g. SYBR green, Molecular Beacons, Scorpion Probes, etc.) are suitable for use in the methods of the present invention.

To minimize errors and the effect of sample-to-sample variation, RT-PCR is usually performed using an internal standard. The ideal internal standard is expressed at a constant level among different tissues. RNAs most frequently used to normalize patterns of gene expression are mRNAs for the housekeeping genes glyceraldehyde-3-phosphate-dehydrogenase (GAPDH) and β-actin.

Real time PCR is compatible both with quantitative competitive PCR, where internal competitor for each target sequence is used for normalization and quantitative comparative PCR using a normalization gene contained within the sample, or a housekeeping gene for RT-PCR. For further details see, e.g., Heid et al., "Real Time Quantitative PCR," *Genome Research* 6:986-994 (1996), which is incorporated by reference in its entirety.

When it is desirable to measure the expression level of cytochrome-c, c-Myc, and/or NF-κB by measuring the level of protein expression, the method may involve reagents suitable for performing any protein hybridization or immunodetection based assay known in the art. In a protein hybridization based assay, an antibody or other agent that selectively binds to a protein is used to detect the amount of that protein expressed in a sample. For example, the level of expression of a protein can be measured using methods that include, but are not limited to, western blot, immunoprecipitation, enzyme-linked immunosorbent assay (ELISA), radioimmunoassay (RIA), fluorescent activated cell sorting (FACS), immunohistochemistry, immunocytochemistry, or any combination thereof. Also, antibodies, aptamers, or other ligands that specifically bind to a protein can be affixed to so-called "protein chips" (protein microarrays) and used to measure the level of expression of a protein in a sample. Alternatively, assessing the level of protein expression can involve analyzing one or more proteins by two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MS/MS), protein chip expression analysis, gene chip expression analysis, and laser densitometry, or any combinations of these techniques.

Immunoassays can be used to measure cytochrome-c, c-Myc, and NF-κB protein expression in the prostate cell sample. If cytochrome-c, c-Myc, and/or NF-κB are present in the sample, it will form an antibody-protein complex with an antibody that specifically binds the protein under suitable incubation conditions described above. In one embodiment, an immunoassay involves contacting the cell sample with a combination of antibodies suitable to detect cytochrome-c, c-Myc, and NF-κB protein expression simultaneously. The amount of an antibody-protein complex can be determined by comparing to a standard. A standard can be the level of cytochrome-c, c-Myc, NF-κB protein in a non-cancerous tissue matched control sample or the average level in a tissue matched sample from a cohort of healthy individuals. As noted above, the test amount of cytochrome-c, c-Myc, and/or NF-κB need not be measured in absolute units, as long as the unit of measurement can be compared to a control.

Methods for measuring the level of phosphorylation at an amino acid residue (i.e., in Drp1 or Akt1) are conventional and routine in the art. In one embodiment, the level of phosphorylation at serine residue 616 and serine residue 637 of Drp1 are measured. In one embodiment, the level of phosphorylation at serine 473 of Atk1 is measured. In another embodiment, the level of Drp1 serine phosphorylation and Akt1 phosphorylation are determined together in a single assay.

In general, detection and quantitation of phosphorylation relies on the existence of sets of antibodies that are specific for either the non-phosphorylated or the phosphorylated forms of a particular amino acid residue of interest in the context of a protein of interest (such as Drp1 or Akt1). Such antibodies are commercially available or can be generated routinely, using conventional procedures. In one embodiment, a synthetic peptide comprising an amino acid of interest from a protein of interest (either in the non-phosphorylated or phosphorylated form) is used as an antigen to prepare a suitable antibody. The antibody can be polyclonal or monoclonal. Antibodies are selected and verified to detect only the phosphorylated version of the protein but not the non-phosphorylated version of the native or denatured protein, and vice-versa.

Such antibodies can be used in a variety of ways. For example, one can prepare whole cell lysates from patient samples and spot them in an array format onto a suitable substrate, such as nitrocellulose strips or glass slides. Preferably, the proteins in the samples are denatured before spotting. In general, the cells are spotted at serial dilutions, such as two-fold serial dilutions, to provide a wide dynamic range. Suitable controls, such as positive controls or controls for base line values, can be included. Each array is then probed with a suitable detectable antibody, as described above, to determine and/or to quantitate which amino acid residue(s) in the various proteins of interest are phosphorylated. Methods for immuno-quantitation are conventional. For a further discussion of this method of reverse phase protein lysate microarrays (RPMA), see, e.g., Nishizuka et al. (2003) *Proc. Natl. Acad. Sci.* 100, 14229-14239, which is hereby incorporated by reference in its entirety. Other suitable assays employing such antibodies to assess the level and/or degree of phosphorylation at a residue of interest include, e.g., Western blots, ELISA assays, immunoprecipitation, mass spectroscopy, and other conventional assays. Suitable methods include those that can detect the phosphoprotein in a very small sample (e.g. about 200 cells). Alternatively, methods can be used that are suitable for a large sample size (e.g. about 20,000-25,000 cells).

Assays to measure the presence and/or amount of phosphorylated residues can be readily adapted to high throughput formats, e.g. using robotics, if desired.

In accordance with this aspect of the present invention, the measurement of cytochrome-c levels and Drp1 phosphorylation levels alone or in combination with detection and quantitation of c-myc and NF-κB expression and/or activity and Akt1 phosphorylation levels can be used to determine and develop an appropriate therapeutic regimen for the individual having cancer. For example, if the results of such measurements show that the individual has a deficiency in cytochrome-c expression or activity, this informs the physician that the individual has a form of cancer that is or is likely to develop resistance to drug induced apoptosis. The determination of whether the cytochrome-c deficiency is the result of decreased expression and/or decreased activity (e.g., release from mitochondria). If the results show a decrease in cytochrome-c expression, detection of the mechanism underlying that decrease (e.g., increased c-myc activity, increased NF-κB activity, or reduced Akt1 activity) will further inform the physician as to what therapeutic agent or combination of agents (e.g., c-myc inhibitor, NF-κB inhibitor, Akt1 activator, or Drp1 modulator) will be most effect for the treatment of the patient. Thus, the methods described herein have diagnostic and prognostic value, and importantly, allow for the implementation of an optimized treatment regimen for the patient.

Another aspect of the present invention is directed to a kit containing the reagents suitable for measuring cytochrome-c expression levels as described herein and reagents suitable for measuring Drp1 phosphorylation levels as described herein are combined in a kit. Such kit can further include reagents suitable for measuring Akt1 phosphorylation level, c-Myc expression level, NF-κB expression level, or any combination of reagents thereof.

Background for the Examples

African-American (AA) men are more often diagnosed with prostate cancer (PCa) and suffer higher mortality rates than Caucasian-American (CA) men. These poor outcomes are due to the fact that AA PCa patients respond more poorly than their CA counterparts to current therapeutic approaches. AA PCa is more aggressive, takes less time to relapse, shows molecular differences, and has greater likelihood of metastasis than CA PCa. While the molecular mechanisms driving acquisition of these characteristics in AA PCa remain largely unknown, the applicants and others have demonstrated that mitochondrial dysfunction is a key contributing factor to therapeutic resistance. One of the reasons for greater PCa aggressiveness in AA men is the existence of defective oxidative phosphorylation (OXPHOS) system in AA PCa cells and tumors. Mitochondrial DNA (mtDNA) copy number is reduced in non-tumor prostatic tissues in AA men with PCa compared to CA men with PCa. MtDNA encodes proteins critical for OXPHOS Complexes I, III, IV, and V. Therefore, the reduced level of mtDNA may compromise OXPHOS function leading to aberrant activity/expression of other components of the OXPHOS system, such as cytochrome c (CC). CC transfers electrons from Complex III to Complex IV during electron transport for ATP production. Thus OXPHOS defects due to reduced mtDNA and aberrant CC expression may promote aerobic glycolysis in AA PCa compared to CA PCa. This hypothesis is supported by the fact that AA PCa, compared to CA PCa, exhibits higher levels of key proteins, such as c-Myc and NF-κB, that foster a glycolytic phenotype. Whether and how upregulation of c-Myc and other regulators of aerobic glycolysis compromise OXPHOS function in AA men with PCa remain unclear.

It is noted that AA PCa cells resist apoptosis due to lack of caspase activation. However, the underlying causes of resistance to apoptosis in response to various anticancer agents remain undefined. In solid epithelial cancers, such as PCa, mitochondria are required for efficient apoptosis triggered by release of CC, a key component of the OXPHOS system. CC release from mitochondria interacts with and activates an adapter protein, apoptotic protease-activating factor-1 (Apaf-1), which undergoes oligomerization to form the apoptosome that recruits and activates caspase-9 at the apoptosome complex. Caspase-9 then activates effector caspases, such as caspase-3, to execute apoptosis. Apoptosome dysfunction has been reported in some cancer types, but whether higher therapeutic resistance in AA PCa patients is due to apoptosome dysfunction remains unknown. Apoptosome dysfunction may occur via protein deficiency of apoptosomal components or due to defects in CC release from mitochondria. The first comprehensive evidence that CC-deficiency in AA PCa cells contributes to development of aggressive PCa and therapeutic resistance is disclosed. Defining underlying mechanisms causing CC deficiency have revealed novel therapeutic approaches to restore CC, inhibit aerobic glycolysis, and sensitize PCa cells to first line chemotherapeutic agents, such as docetaxel (DOC).

EXAMPLES

Materials and Methods

Patient samples: Primary prostate tumors (PT), matching non-tumor (MN) prostate tissues, and total RNA from CA and AA PCa patients were collected at Roswell Park Comprehensive Cancer Center (Roswell Park) by the Pathology Network Shared Resource (PNSR) under approved IRB protocol. The patient's samples were de-identified by PNSR and patient information was not provided to researchers.

Mice: All animal experiments were approved by and performed in compliance with the guidelines and regulations by the Roswell Park Institutional Animal Care and Use Committee (IACUC, protocol #1306M). 6-8 weeks old SCID male mice were purchased from the Roswell Park Division of Laboratory Animal Resources (DLAR). All mice were kept under standard conditions and diet.

Cell lines: LNCaP, DU145, and PC-3 cells were maintained in RPMI 1640 media (Life Technologies, Carlsbad, Calif.) supplemented with 7% FBS and 100 U $ml^{-1}$ penicillin/streptomycin. E006AA and E006AA-hT cells were maintained in high glucose DMEM (Life Technologies, Carlsbad, Calif.) supplemented with 7% FBS and 100 U $ml^{-1}$ penicillin/streptomycin. RWPE-1, RC-77 T/E and RC-77 N/E cells were maintained in keratinocytes-SFM (Life Technologies, Carlsbad, Calif.) supplemented with EGF and BPE. Human cell lines acquired from ATCC or collaborators are profiled by short tandem repeat (STR) analysis every 6 months. Early passage cells are cryopreserved for subsequent use in all experiments to reduce possible genetic drift. Cultures are passaged for no more than 3 months at which time they are replaced from cryopreserved stocks. Cell lines are screened routinely for mycoplasma contamination using Hoechst staining or a more sensitive PCR assay. Details about all cells studied are provided in supplemental methods.

Compounds: Docetaxel (DOC) was purchased from Cayman chemicals, Ann Arbor, Mich. (Cat #11637). Pharmacological inhibitors of c-Myc (10058-F4; Cat #15929) and NF-κB (JSH-23; Cat #15036) transcription factors were purchased from Cayman chemicals, Ann Arbor, Mich. bpV (pic) (AKT activator) was purchased from Cayman chemicals, Ann Arbor, Mich. (Cat #14434). All compounds were reconstituted in 100% DMSO and diluted in cell culture media before use.

Gene specific silencing using shRNA lentiviral particles: Cells were seeded ($5\times10^4$ cells) per well of 6 well plates. After 24 hrs, polybrene (8 μg/ml) was added to the media. After 1 hr, mock shRNA or gene specific shRNA (CYCS, Drp1 and Nrf1) lentiviral particles were added at MOI of 2. After 48 hrs of transduction, media was replaced with fresh media containing 1 μg/ml puromycin for selection of transduced cells as described (5). Knock down of targeted gene was confirmed using immunoblotting.

Gene specific silencing using siRNA: Cells ($1\times10^5$ cells) per well of 6 well plates were transfected with siRNA for c-Myc or p65 subunit of NF-κB or PTEN using lipofectamine 3000 system as per manufacturer's instructions. After 24 hrs of transfection, cells were treated with DOC (10 nM for 24 hrs) alone or in combination with either c-Myc inhibitor (c-Myc I, 75 μM) or NF-κB inhibitor (NF-κB I, 50 μM) or AKT activator (AKT Act, 5 μM). Whole cell lysates were prepared and used for DEVDase activity and immunoblotting for CC. Knock down of the targeted gene was confirmed using immunoblotting.

Statistical analysis. Significant differences between means were assessed using analysis of variance (ANOVA) and GraphPad Prism Version 6.0. A *$p<0.05$ value was accepted as significant. Significance was denoted as compared to control, unless otherwise indicated.

Experimental details for CC overexpression using CRISPR-SAM, MitoROS and MitoMass quantification, Annexin/PI staining, mtDNA determination, subcellular fractionation, ChiP and CC promoter assay, real time PCR, immunoblotting, immunofluorescence, immunohistochemistry (IHC), cell viability and caspase-3 (DEVDase) assay, bioenergetics and clonogenic assays, PCa cell xenograft, and cell cycle analysis as well as a list of antibodies (Table 1), shRNA sequences (Table 2), and siRNA sources (Table 3) are detailed below.

Cell lines: E006AA and E006AA-hT cells were generated and provided by Dr. Shahriar Koochekpour, Roswell Park (1, 2). RC-77 T/E and RC-77 N/E cell lines were isolated and characterized by Dr. Johng S. Rhim at Uniformed Services University of Health Sciences (3). CA PCa cell lines (LNCaP, DU145, PC-3), and non-neoplastic prostate epithelial RWPE-1 cells were purchased from ATCC (Manassas, Va.).

Endogenous cytochrome c (CC) over-expression by CRISPR-SAM: sgRNA SAM probes (guide sequence: CACCGCGTGCGTGCCCTTCTTCTCG; AAACCGAGAAGAAGGGCACGCACGC [SEQ ID:1]) for CYCS genes were cloned into sgRNA (MS2) cloning backbone (gift from Dr. Feng Zhang; Addgene plasmid #61424) using golden-gate sgRNA cloning protocol, as described in Konermann et al., 2014 (4). Scrambled sgRNA (guide sequence: CACCGCTGAAAAAGGAAGGAGTTGA; AAACTCAACTCCTTCCTTTTTCAGC [SEQ ID:2]) was cloned in sgRNA (MS2) cloning backbone. Two μl of the golden gate reaction were transformed in Stbl3 competent cells and transformed colonies were selected on ampicillin plates. The CYCS sgRNA clones were confirmed using the Sanger sequencing at the Genomics Shared Resources. E006AA cells were co-transfected with CYCS-sgRNA(MS2) plasmids along with MS2-P65-HSF1_GFP (gift from Dr. Feng Zhang; Addgene plasmid #61423) and dCAS9-VP64_GFP (gift from Dr. Feng Zhang; Addgene plasmid #61422) plasmids using lipofectamine 3000 cell transfection system (Life Technology, Carlsbad, Calif.). After 48 hrs, cells were harvested and analyzed for CC protein expression and caspase-3 activity.

Mitochondrial reactive oxygen species (mitoROS) estimation: Stable mock shRNA and CYCS shRNA expressing LNCaP and PC-3 cells were seeded in 6 well cell culture plates for 48 hrs. Cells were incubated in MitoSOX staining solution (2 μM MitoSOX in Phenol red free-RPMI1640 and 2% FBS) for 30 min in $CO_2$ cell culture incubator. After incubation, cells were collected using trypsinization and washed twice with phenol red free-RPMI1640 and 2% FBS. MitoSOX fluorescence was measured using flow cytometry and PE filter (red fluorescence) as described. Data were analyzed using FACS-DIVA software and represented as fold change compared to mock shRNA group.

Annexin/PI staining: Mock, CC, Drp1 knock down cells were treated with docetaxel or vehicle and apoptotic cells were identified using the annexin-V-Alexafluor 488/PI kit (Invitrogen, USA) according to the manufacturer's instructions and as described previously (5, 7). The stained cells were analyzed using flow cytometry (LSR II, BD Biosciences) to collect 10,000 events. Data were analyzed using BD FACS Diva software.

Mitochondrial DNA (mtDNA) copy number/content determination: Total genomic DNA (containing both mtDNA and nuclear DNA) was isolated from stable mock shRNA and CYCS shRNA expressing LNCaP and PC-3 cells using Quick-DNA kit from Zymo Research (Cat #D3021). DNA was quantified using the NanoDrop 8000 Spectrophotometer, mtDNA content was determined using the Applied Biosystems 7300 real-time PCR system. β-actin and cytochrome c oxidase subunit II (COX II) were used to amplify nuclear and mtDNA, respectively. Primers for β-actin and COX II were as follows: β-actin (forward): 5'-TCACCCACACTGTGCCCATCTACGA-3' [SEQ ID:3], β-actin (reverse): 5'-CAGCGGAACCGCTCATTGCCAATGG-3' [SEQ ID:4]. COX II (forward): 5'-CCCCACATTAGGCTTAAAAACAGAT-3' [SEQ ID:5], COX II (reverse): 5' TATACCCCCGGTCGTGTAGCG GT-3' [SEQ ID:6]. Real-time PCR reactions were performed in total reaction volume 10 μl that contained 5 μl 2xiTaq SYBR Green Supermix with ROX (Bio-Rad, Cat #172-5850), 10 ng template DNA, 100 nM each of forward and reverse primers, and nuclease-free water. Melting curve analyses were performed at the end of amplification to verify the absence of nonspecific amplification or primer dimer formation. The threshold cycle number (Ct) values for each reaction were calculated using the 7300 system SDS software. Average Ct values were obtained using amplification of COX II (mtDNA-specific) and β-actin (nDNA-specific). MtDNA content was determined as 2^ΔCt, or fold difference of mtDNA from nDNA.

Subcellular fractionation for the preparation of cytosolic and mitochondrial fractions: Cells were seeded on 15 cm cell culture plates followed by treatment with various compounds for the preparation of cytosolic and mitochondrial fractions as described. Cells were harvested via gentle scraping, washed twice with ice cold 1×PBS, and resuspended in homogenization buffer (20 mM HEPES, pH 7.4; 10 mM KCl; 1.5 mM $MgCl_2$; 1 mM EDTA; 1 mM EGTA; 250 mM sucrose) supplemented with freshly added 1× protease inhibitor cocktail and 1 mM DTT. Cells were incubated in homogenization buffer for 30 min in ice and homogenized using a dounce homogenizer (~25 strokes using pestle A). Cell homogenates were pre-cleared of unbroken cells and debris using centrifugation at 1000 g for 10 min. The supernatant was collected in new tubes and centrifuged at 12000 rpm for 20 min to obtain a mitochondrial pellet, which was washed 3 times with homogenization buffer and lysed in NP40 buffer, and stored as the mitochondrial fraction. The supernatant was ultra-centrifuged to obtain purified cytosol.

Subcellular fractionation for the preparation of cytosolic and nuclear fractions: Cells were seeded on 10 cm cell culture plates for treatment. Cells were harvested via gently scraping. Cells were collected using centrifugation and washed twice with ice cold PBS. Cells were resuspended in cytosolic buffer (10 mM HEPES, pH 7.4; 10 mM KCl; 0.1 mM EDTA; 0.1 mM EGTA) supplemented with freshly added 1× protease inhibitor cocktail and 1 mM DTT. Cells were incubated in cytosolic buffer for 15 min in ice and 10% NP40 was added (12.4 µl 10% NP40 per 200 µl volume of cytosolic buffer) followed by vigorous vortexing for 45 sec. Cell homogenates were centrifuged at 14000 rpm for 2 min. The supernatant was collected in new tubes and stored as the cytosolic fraction. The nuclear pellet was washed 3 times with cytosolic buffer and lysed in nuclear lysis buffer (10 mM HEPES, 500 mM NaCl, 1 mM EDTA, 1 mM EGTA, 1% NP40) to prepare nuclear extract.

Chromatin immunoprecipitation (ChIP) assay: The association of Nrf1 transcription factor with CYCS promoter within the LNCaP and E006AA cells was detected using a chromatin immunoprecipitation (ChIP) Assay Kit (Millipore, Billerica, Mass.; Cat #17-295) according to the manufacturer's instructions. In brief, 1 million cells were fixed in formaldehyde for 15 min and chromatin was sheared using Bioruptor sonication device for 10 min in ice with 30 sec on/off cycle (Diagenode, Denville, N.J.). Ten µl sonicated samples (of 2 ml total volume) were separated as input. Chromatin was immunoprecipitated with 1.0 µg of Nrf1 or normal rabbit IgG (Santa Cruz Biotechnology) antibody at 4° C. overnight. Each sample (5 µl) was used as a template for PCR amplification and 20 µl of the 50 µl PCR product was loaded onto agarose gels. CYCS oligonucleotide sequence encompasses the CYCS promoter segment that includes the Nrf1 binding sites for PCR primers viz 5'-ATTAGGGCGTCTTTTCCTGG-3' [SEQ ID:7] and 5'-AGCATGTTAGGGTGTACGGC-3' [SEQ ID:8]. PCR mixtures were amplified for 1 cycle at 94° C. for 5 min followed by 35 cycles at 94° C. for 30 s, 55° C. for 30 s and 72° C. for 30 s, and then subjected to final elongation at 72° C. for 10 min. PCR products were run on 2% agarose gel and analyzed using ethidium bromide staining.

Cytochrome c (CYCS) promoter reporter assay: CYCS promoter reporter clone and empty pLightSwitch vector were purchased from SwitchGear Genomics, Menlo Park, Calif. (Cat #S721763). The reporter construct was prepared by cloning −1000 bp of CYCS promoter from the transcription initiation site. Plasmids were transformed in DH5a *E. Coli* strain and were isolated using a Zymo Plasmid MidiPrep kit (Zymo research, cat #D4200). The Nrf1 binding site in the p-CYCS-SwichGear-Luc construct was deleted using a QuickChange II XL site-directed mutagenesis kit (Agilent Technologies, Wilmington, Del. Cat #200521). LNCaP and E006AA cells were seeded in 96 well plates and transfected with either pLightSwitch empty vector or CYCS promoter reporter clones using a lipofectamine 3000 transfection kit (ThermoFisher Scientific, Waltham, Mass.). Cells were harvested after 48 hrs. Luciferase activity assay was performed using LightSwitch Assay Reagent (SwitchGear Genomics, Menlo Park, Calif. Cat #LS010).

Plasmid preparation: DH5-α/Stbl3 *E. coli* strain was grown in standard Luria Broth media at 37° C. Competent cells were prepared and transformed with plasmids using a Mix & Go *E. coli* Transformation Kit (Zymo Research, Irvine, Calif. Cat #T3001) as per manufacturer's instructions.

Semi quantitative real time PCR: Total RNA from CA and AA patients with PCa were provided by the Roswell Park Pathology Network Shared Resource (PNSR). 400 ng of total RNA were used for cDNA synthesis using a High-Capacity cDNA Reverse Transcription Kit (ThermoFisher Scientific, Waltham, Mass.; Cat #4368813). 20 ng cDNA from each sample was used for RT PCR analysis of LDHA using gene specific primer, 2×iTaq SYBR Green Supermix with ROX (Bio-Rad, Cat #172-5850), 100 nM each of forward and reverse primers, and nuclease-free water. Primers used for RTPCR assay were—CYCS (forward): 5'-TTTGGATCCAATGGGTGATGTTGAG-3' [SEQ ID:9], CYCS (reverse): TTTGAATTCCTCATT-AGTAGCTTTTTTGAG-3' [SEQ ID:10]. LDHA (forward): 5'-GGAGATCCATCATCTCTCCC-3' [SEQ ID:11], LDHA (reverse): 5'-GGCCTGTGCCATCAGTATCT-3' [SEQ ID:12]. β-actin (forward): 5'-TCAC CCACACTGTGCC-CATCTACGA-3' [SEQ ID:13], β-actin (reverse): 5'-CAGCGGAACCGCTCATTGCCAATGG-3' [SEQ ID:14]. Melting curve analyses were performed at the end of the amplification to verify the absence of nonspecific amplification or primer dimer formation. The threshold cycle number (Ct) values for each reaction were calculated using the 7300 system SDS software. Average Ct values were obtained by amplification of target genes normalized with β-actin as housekeeping control. Relative mRNA expression was determined as 2 ΔCt.

Seahorse XF bioenergetics assay: Basal glycolytic reserve capacity in PC-3, DU145, and E006AA PCa cells was assessed using an Agilent seahorse XF glycolytic stress test kit (Agilent Technologies Inc., Wilmington, Del.) and a Seahorse XF96 analyzer (Agilent Technologies Inc., Wilmington, Del.) analyzer as described. ATP production in E006AA cells after treatment with drug combinations was assessed using a Mito Stress test kit (Agilent Technologies Inc., Wilmington, Del.).

Clonogenic assay: PCa cells were seeded in each well of 6 well cell culture plates. Cells were treated and plates were incubated in a $CO_2$ cell culture incubator for 6 more days. Colonies were fixed in 10% formalin first and stained with 0.5% crystal violet solution. Plates were dried and pictures were captured using a Gel documentation system and Coomassie blue filter (Bio Rad, Hercules, Calif.).

Human PCa xenograft study: SCID (C.B-Igh-$1^{b}$/IcrTac-$Prkdc^{acid}$) mice (6 weeks old) were purchased from an in house colony maintained by Roswell Park Laboratory Animal Shared Resource. Animal protocols were approved by the Roswell Park Institutional Animal Care and Use Committee (IACUC protocol #1306M). E006AA hT cells (80% confluency) were harvested and live cells quantified. Harvested cells were washed and resuspended in serum-free DMEM/F-12 (1:1) mix. Four $\times 10^{6}$ E006AA hT cells were mixed with Matrigel (1:1) and injected subcutaneously in the right and left flanks of each mouse. When xenograft tumors reached 5 mm in diameter (22 days post injection), mice were randomly divided into 6 groups of 4 mice. First group received 100 μl Neobee M5 oil (vehicle) and 100 μl normal saline each twice weekly. Second group received 100 μl Neobee M5 oil and DOC (6 mg/kg bw) twice weekly. Third group received 10058-F4 (20 mg/kg bw) and DOC (6 mg/kg bw) twice weekly. Fourth group received JSH-23 (3 mg/kg bw) and DOC (6 mg/kg bw) twice weekly. Fifth group received 10058-F4 (20 mg/kg bw) and normal saline twice weekly. Sixth group received JSH-23 (3 mg/kg bw) and normal saline twice weekly. All treatments were administered for 3 weeks. Mice were euthanized, tumors were excised and flash frozen in liquid nitrogen. The tissue lysates were used for caspase-3 activity and Western blotting of CC, cleaved PARP, and cleaved caspase-3 proteins.

Immunoblotting: Immunoblotting was performed as described previously. Protein lysates were prepared using a lysis in NP-40 buffer (50 mM Tris-HCl pH 7.4, 150 mM NaCl, 1 mM EDTA, 1 mM EGTA, 1% NP-40) supplemented with protease and phosphatase inhibitor cocktail. Protein content was quantified using a micro BCA protein estimation kit (Thermo Scientific, Waltham, Mass.; Cat #23235). Protein samples were resolved on 4-20% Criterion gels, transferred on nitrocellulose membranes (BioRad, Hercules, Calif.) and subjected to immunoblotting. Membranes were blocked in 5% fat free dry milk (Blotto, Santa Cruz, Dallas, Tex.; Cat #sc-2324) prepared in PBS-T (Tween-20) and incubated overnight in primary antibodies (1:1000 dilution) at 4° C. with continuous shaking. After washing with PBS-T, membranes were incubated in HRP conjugated anti-mouse or anti-rabbit secondary antibody at room temperature for 1 hr. After washing with PBS-T, proteins were detected using Clarity chemiluminescent reagent (BioRad, Hercules, Calif.; Cat #1705061) and X-Ray films (ASI, Fort Lauderdale, Fla.; Cat #XR1570). Membranes were stripped using stripping buffer and probed with HRP conjugated beta-actin antibody to ensure equal loading of proteins. The antibodies used are listed in Table 1.

Immunofluorescence: Immunofluorescence staining of CC was performed as described. LNCaP, PC-3, E006AA, and RC-77 T/E cells (5000 cells) were seeded on coverslips. Cells were fixed with 4% paraformaldehyde containing 5% sucrose for 30 min at RT followed by permeabilization with 0.5% Triton X-100 in PBS for 30 min. Fixed cells were washed and blocked with 10% goat serum in 0.3% Triton X-100 diluted in PBS and washed with PBS twice. Cells were incubated with CC antibody overnight at 4° C. Alexafluor-488-conjugated secondary antibody was added for 2 h at 4° C. After washing with 1×PBS twice, coverslips were mounted on glass slides using ProLong® Gold Antifade Mountant with DAPI as mounting medium. Fluorescent images were acquired using a laser-scanning confocal system (Leica TSPS, Leica Microsystems Inc., Buffalo Grove, Ill.) on an inverted microscope at 63× magnification.

Immunohistochemistry (IHC): TMA slides were de-paraffinized and rehydrated followed by incubation in 3% hydrogen peroxide to block endogenous peroxidase activity. For antigen retrieval, slides were incubated in 10 mM citrate buffer (pH 6.0) for 15 min in a microwave oven. Then slides were sequentially incubated in blocking solution (10% goat serum in PBS, 30 min) and primary antibody (mouse monoclonal anti-cytochrome c; 1:1,000× overnight at 40 C). The slides were developed using Dako EnVision+ System-HRP Labelled polymer (Anti-mouse Cat #K4000) as per manufacturer's instructions. The slides were counter-stained with Mayer's hematoxylin followed by a thorough rinse in distilled water. Slides were mounted with aqueous mounting medium (Dako, Cat #S3025) and visualized under Olympus BX41 microscope at 100× magnification.

Cell viability assay: PCa cells ($5\times10^{4}$ cells/well) were seeded on 6-well cell culture plates and incubated with DOC (1-20 nM) for 24 hrs. Floating and attached cells were collected using trypsinization. Live and dead cells were counted under a light microscope using a trypan blue exclusion assay.

Caspase-3 (DEVDase) activity assay: PCa cell lysates prepared in NP40 lysis buffer were incubated with DEVD-AFC (caspase-3 substrate) at 37° C. for 90 min in caspase activity assay buffer (50 mM HEPES pH 7.4, 150 mM NaCl, 1% CHAPS, 1 mM EDTA, 1 mM DTT, 50% glycerol). Fluorescence intensity was detected using a Synergy microplate reader at excitation and emission wavelengths of 400 nm and 508 nm, respectively. Arbitrary fluorescence units were normalized with protein content of cell lysates and represented as fold change compared to control groups.

Cell cycle analysis: Cell cycle phases in LNCaP and E006AA cells were analyzed using Propidium Iodide (PI) staining. Cells were treated with DOC for 24 hrs, fixed in 70% ethanol, stained with PI staining solution (0.1% sodium citrate, 0.2 mg/ml RNAse, 0.05 mg/ml propidium iodide, 0.2% NP 40, 1N HCl), and analyzed using flow cytometry. Data were analyzed using FACS-DIVA software and represented as % cells in each cell cycle phase.

TABLE 1

List of antibodies used

| Antibody | Source | Catalog number |
|---|---|---|
| Mouse monoclonal Anti-cytochrome c (clone 7H8.2C12) for immunoblotting | BD Biosciences | Cat #556433 |
| Mouse Anti-cytochrome c clone 6H2.B4 (RUO) for immunofluorescence | BD Biosciences | Cat #556432 |
| Apaf-1 | BD Biosciences | Cat # 559683 |
| Caspase-9 | Cell Signaling | Cat # 9502 |
| Caspase-3 | Enzo | Cat # BML-6A320-0100 |
| Actin-HRP | Santa Cruz Biotechnology | Cat # SC-47778 |
| LDHB | Abcam | Cat # ab85319 |
| TOM20 | Cell Signaling | Cat # 42406 |
| PGC1-α | Santa Cruz Biotechnology | Cat # SC-13067 |
| SP-1 | Abcam | Cat # ab13370 |
| Nrfl | Abcam | Cat # ab34682 |
| Lamin B1 | Santa Cruz Biotechnology | Cat # sc-6216 |

-continued

| | | |
|---|---|---|
| c-Myc | Cell Signaling | Cat # 9402 |
| NF-κB | Cell Signaling | Cat # 8242 |
| p-AKT$^{S473}$ | Cell Signaling | Cat # 4060 |
| AKT | Cell Signaling | Cat # 4691 |
| TBP | Proteintech | Cat # 22006-1-AP |
| PARP-1 | Cell Signaling | Cat # 9532 |
| Cleaved caspase-3 | Cell Signaling | Cat # 9661 |
| Drp1 | Cell Signaling | Cat # 8507 |
| OPA-1 | Cell Signaling | Cat # 67589 |
| p-Drp1$^{S616}$ | Cell Signaling | Cat # 4494 |
| p-Drp1$^{S637}$ | Cell Signaling | Cat # 4867 |
| GAPDH | Santa Cruz Biotechnology | Cat # sc-47724 |
| p-Erk | Santa Cruz Biotechnology | Cat # sc-7383 |
| Erk1/2 | Santa Cruz Biotechnology | Cat # sc-94 |
| Cleaved PARP | Cell Signaling | Cat # 5625 |
| NDUFA9 | Abcam | Cat # ab14713 |
| SDHA | Abcam | Cat # ab14715 |
| UQCRC2 | Abcam | Cat # ab14745 |
| COX IV | Cell Signaling | Cat # 11967 |
| ATP5A | Abcam | Cat # ab14754 |
| FAK | Millipore Upstate | Cat # 05-537 |
| Hexokinase 1 | Cell Signaling | Cat # 2024 |
| Hexokinase 2 | Cell Signaling | Cat # 2867 |
| PFKP | Cell Signaling | Cat # 8164 |
| PKM ½ | Cell Signaling | Cat # 3190 |
| PKM2 | Cell Signaling | Cat # 4053 |
| PDH | Cell Signaling | Cat # 3205 |
| LDHA | Cell Signaling | Cat # 3582 |
| Anti-rabbit IgG, HRP | Cell Signaling | Cat # 7074 |
| Anti-mouse IgG, HRP | Cell Signaling | Cat # 7076 |
| Anti-mouse IgG, Alexa Fluor 488 | ThermoFisher Scientific | Cat # A-11001 |
| Normal rabbit IgG | Santa Cruz Biotechnology | Cat # sc-2027 |

TABLE 2

List of shRNA and sequences

| shRNA | Mature Antisense Sequence |
|---|---|
| CYCS shRNA1 | 5'-TATAAATTGCTTTCAGGCC-3' [SEQ ID: 15] |
| CYCS shRNA2 | 5'-TACTTCATCAGGCATATGC-3' [SEQ ID: 16] |
| Drp1 shRNA1 | 5'-TAATGAGTCGTTCAATAAC-3' [SEQ ID: 17] |
| Drp1 shRNA2 | 5'-TTGGTGTGAAGAAATTTAC-3' [SEQ ID: 18] |
| Nrf1 shRNA1 | 5'-ATCTGAGTCATCGTAAGAG-3' [SEQ ID: 19] |
| Nrf1 shRNA2 | 5'-TACTATGTGTGGCTGTGGC-3' [SEQ ID: 20] |

Lentiviral particles specific for CYCS, Drp1, Nrf1 and control shRNAs were obtained from the Roswell Park Comprehensive Cancer Center shRNA core resource and were directly utilized to infect cells at a multiplicity of infection (MOI) of 2.

TABLE 3

List of siRNA and sources

| siRNA | Source | Catalog Number |
|---|---|---|
| Control siRNA-A | Santa Cruz Biotechnology | Cat # sc-37007 |
| c-Myc siRNA | Santa Cruz Biotechnology | Cat # sc-29226 |
| NF-κB p65 siRNA | Santa Cruz Biotechnology | Cat # sc-29410 |
| PTEN siRNA | Santa Cruz Biotechnology | Cat # sc-29459 |

Results

CC, a key component of apoptosome and OXPHOS system, is reduced in PCa cell lines and tumor specimens derived from AA men with PCa: PCa cell lines derived from AA PCa patients are more resistant to anticancer agents than to PCa cell lines derived from CA PCa patients. One possible explanation for greater therapeutic resistance in AA men with PCa is apoptosome dysfunction in AA PCa cells compared to CA PCa cells. First, the expression of the apoptosome components in AA PCa cells was measured. Analysis of mRNA in E006AA and E006AA hT (AA PCa), and PC-3 and LNCaP (CA PCa) cells demonstrated reduced levels of CC mRNA in AA PCa cells compared to CA PCa cells (FIG. 8A). The reduced level of CC protein via immunoblotting in AA PCa cells validated reduced expression of CC mRNA (FIG. 1A). Immunolabeling of CC supported CC-deficiency in AA PCa cells compared to CA PCa cells (FIGS. 1B and 8B). In contrast, the levels of other components of the apoptosome, such as Apaf-1, caspase-9, and caspase-3, were not altered significantly in AA and CA PCa cells (FIG. 1A). The clinical relevance of apoptosome dysfunction in AA men with PCa was evaluated by measuring the levels of CC in primary tumor (PT) and matched non-tumor (MN) prostate tissues using immunoblotting. CC protein expression was reduced in PT and MN tissues of AA men compared to CA men (FIG. 1C). Sections of a PCa tissue microarray (TMA) constructed from PT and MN from AA (n=92) and CA (n=89) patients (FIG. 1D) were immunostained with CC antibody. Analysis of MN and PT from AA and CA men with PCa provides two important outcomes. First, PT from AA PCa patients showed reduced CC level compared to CA counterparts that suggests apoptosome dysfunction is due to the lack of CC in AA PCa. Second, MN in AA PCa patients show reduced expression of CC compared to CA men with PCa (FIGS. 1C and D). CC is critical for the assembly of apoptosome, so lack of CC suggests the existence of apoptosome dysfunction in PCa cells, and PT and MN from AA men with PCa.

Lack of CC causes apoptosome dysfunction and apoptosis resistance in AA PCa cells: Reconstitution experiments using purified cytosol and CC demonstrated that lack of CC is a key reason for inhibition of apoptosome-mediated caspase activation in AA PCa cells (FIG. 2A). DOC-induced caspase activation and cell death were reduced in various AA PCa cells compared to CA PCa cells (FIGS. 2B and C, and FIGS. 9A-C). To rule out the possibility that lack of apoptosis in AA PCa cells is due to expression of multidrug transporters, the effect of DOC on the cell cycle were evaluated. Both AA and CA PCa cells showed similar cell cycle arrest at G2/M phase after DOC treatment (FIG. 2D). To test whether CC deficiency in AA PCa confers therapeutic resistance, we increased expression of endogenous CC in E006AA cells using the CRISPR-SAM technique. Increased expression of endogenous CC induced robust caspase-3 activation in E006AA cells (FIGS. 2E and F). Thus, CC is a limiting factor for DOC-induced apoptosis in AA PCa cells.

CC-silencing in CA PCa cells induces mitochondrial and apoptosome dysfunction leading to inhibition of caspase activation and apoptosis resistance: CC is an important component of apoptosome formation, but it also plays a critical role in energy metabolism by participating in the electron transport chain (ETC) of the oxidative phosphorylation (OXPHOS) system. To test whether lack of CC contributes to mitochondrial and apoptosome dysfunction, a reverse approach was used by generating CC-silenced CA PCa (LNCaP and PC-3) cells using shRNA lentiviral particles (FIG. 2G). CC-silenced CA PCa cells were resistant to DOC treatment as evidenced by inhibition of caspase-3 activity, apoptotic cell death, and levels of cleaved PARP and caspase 3 (FIG. 2H; FIGS. 10A and 10B). CC-silencing significantly decreased mitochondrial mass (mitoMass), mitochondrial reactive oxygen species (mitoROS), and mitochondrial DNA (mtDNA) in CA PCa cells (FIGS. 2I, J and K). MtDNA content was reduced in AA PCa cells compared to CA PCa cells. These findings suggest that lack of CC contributes to mitochondrial dysfunction and apoptosis resistance.

Abrogated nuclear respiration factor-1 (Nrf1) translocation to nucleus contributes to CC loss in AA PCa cells: Expression of CC in mammalian cells is regulated by peroxisome proliferator-activated receptor gamma coactivator 1-alpha (PGC1-α), specificity protein 1 (SP-1), and nuclear respiratory factor 1 (Nrf1) transcription factors. To define the mechanism of reduced expression of CC, the level of these transcription factors were first analyzed using nuclear fractions of E006AA (low CC expression) and LNCaP (high CC expression) cells. Similar levels of PGC1-α and SP-1 were observed in the nuclear fractions of both high and low CC expressing cells, but Nrf1 was reduced in the nuclear fraction of E006AA cells compared to LNCaP cells (FIG. 3A), suggesting that reduced Nrf1 nuclear translocation contributes to CC-deficiency in E006AA cells. Chromatin immunoprecipitation (ChIP) analysis of the CC promoter demonstrated reduced binding of Nrf1 in AA PCa cells compared to CA PCa cells (FIG. 3B). To confirm that abrogation of Nrf1 binding to the CC promoter reduced expression of CC, the CC promoter region containing PGC1-α, SP-1 and Nrf1 binding sites was cloned in pLightSwitch-Luc vector with luciferase as the reporter gene (CYCS-Luc). The promoter-reporter assay analysis confirmed that the CC gene (CYCS) promoter activity was reduced in E006AA cells compared to LNCaP cells. Deletion of the Nrf1 binding site from p-CYCS-LightSwitch-Luc vector (ΔCYCS-Luc) abolished its promoter activity as evidenced by decreased luciferase activity upon its transfection in LNCaP cells (FIG. 3C). Taken together, these data demonstrated that nuclear Nrf1 is the rate-limiting factor for the expression of CC in AA PCa and tumor cells.

The cytosolic level of Nrf1 was similar in LNCaP and E006AA cells, that prompted an experiment to test if nuclear translocation of Nrf1 was inhibited in E006AA cells (FIG. 3A). Cellular Myc (c-Myc) and NF-κB transcription factors regulate Nrf1 translocation and its target genes. Both c-Myc and NF-κB are hyperactivated in AA PCa patients, indicating their involvement in abrogating Nrf1 nuclear translocation. Nuclear accumulation of both c-Myc and NF-κB transcription factors was elevated in AA PCa cells (E006AA and RC-77 T/E cells), which may lead to suppression of nuclear translocation of Nrf1 (FIG. 3D, and FIG. 11A). Expression of c-Myc was upregulated in both MN and PT from AA patients compared to CA patients (FIG. 3E). Next, the involvement of AKT signaling was determined, which phosphorylates and activates Nrf1 and its target genes. Reduced levels of active AKT (p-AKTS473) in E006AA compared to LNCaP cells (FIG. 3F). A larger panel of CA and AA PCa cells further establish that reduced Akt phosphorylation correlates with reduced CC expression (FIG. 3G). These findings demonstrate that activation of c-Myc or NF-κB and suppression of p-AKT signaling may contribute to the abrogation of Nrf1 nuclear translocation that leads to reduced expression of CC in AA PCa cells compared to CA PCa cells.

Genetic and pharmacological inhibition of c-Myc and/or NF-κB, and activation of AKT enhance Nrf1 nuclear translocation to promote CC expression: To establish the biological significance of c-Myc and/or NF-κB activation and AKT inhibition in abrogating CC expression and apoptosis, CC expression and cell death were measured in response to specific pharmacological inhibitors of c-Myc or NF-κB alone, AKT activator alone and their combinations with DOC. Increased CC expression, increased caspase-3 activation, PARP cleavage, and enhanced cell death were observed in response to combined treatment with DOC and either c-Myc inhibitor, NF-κB inhibitor, or AKT activator in E006AA and other AA PCa cells (FIG. 4A-C, FIGS. 11B and C). Enhanced translocation of Nrf1 to nucleus in AA PCa cells in response to c-Myc or NF-κB inhibitors or AKT activator alone, and when combined with DOC demonstrated that increased expression of CC was due to nuclear translocation of Nrf1 (FIG. 4D). Re-activation of Nrf1 transcriptional activity was validated using ChIP analysis, which demonstrated enhanced binding of Nrf1 to the CC promoter in response to c-Myc or NF-κB inhibitors or AKT activator alone and when combined with DOC (FIG. 4E). Nrf1-silencing inhibited drug sensitivity to c-Myc inhibitor, NF-κB inhibitor, and AKT activator alone and when combined with DOC (FIG. 12). We confirmed the involvement of Nrf1 in CC expression by treating CYCS-Luc and ΔCYCS-Luc transfected E006AA cells with either c-Myc inhibitor or NF-κB inhibitor or AKT activator for 24 hrs followed by luciferase activity measurement. Treatment with c-Myc inhibitor, NF-κB inhibitor, or AKT activator increased the CYCS promoter activity in CYCS-Luc transfected cells but not in ΔCYCS-Luc transfected cells (FIG. 4F). Silencing of c-Myc, NF-κB and PTEN in AA PCa cells enhanced CC expression and caspase-3 activity with or without DOC treatment (FIGS. 4G and 13A and 13B). Taken together, these data provide evidence that induced expression of CC upon Nrf1 activation sensitized AA PCa cells to DOC albeit not to the same degree as in CA PCa cells.

CC release machinery at the mitochondrial outer membrane in AA PCa cells is defective compared to CA PCa cells: DOC induced CC expression and release from mitochondria to the cytosolic compartment in CA PCa cells, but not in AA PCa cells (FIG. 5A). These findings suggest that CC expression was not altered upon DOC treatment, and the CC release machinery is defective in AA PCa cells, which causes apoptosis resistance in response to DOC. Analysis of cytosolic and mitochondrial fractions for CC levels upon inhibition of either c-Myc or AKT activation in combination with DOC treatment demonstrated CC release only in combination treatment but not with single agent exposure (FIGS. 5B, C and D). These findings were supported by the fact that only a modest increase in caspase-3 activation and poly (ADP-ribose) polymerase (PARP) cleavage was observed in response to inhibitors of c-Myc and NF-κB or AKT activation alone in E006AA cells (FIGS. 4B and C). Another AA cell line, RC-77 T/E cells, showed reduced nuclear Nrf1, high c-Myc, and NF-κB compared to LNCaP (FIG. 11A). Inhibition of either c-Myc or NF-κB induced CC expression and activated caspase-3 activity, which lead to enhanced cell death in both AA PCa cell lines albeit not as effective as in CA PCa cells (FIGS. 11B and 11C).

Deficiency of dynamin-related protein (Drp1) phosphorylation at serine 616 (p-Drp1S616) contributes to defective CC release in AA PCa cells: To define the molecular mechanism for defective CC release in AA PCa cells, the levels of phosphorylated Drp1 protein, which plays a crucial role in mitochondrial dynamics and CC release, were determined. Drp1 primarily localizes in the cytosolic compartment, translocates to the outer mitochondrial membrane, and modulates mitochondrial cristae structure to cause CC release into the cytosol in response to cellular stress. Drp1 was translocated to mitochondria in response to DOC in CA PCa cells (FIG. 5E). Surprisingly, AA PCa cells expressed higher Drp1 protein that was detected mostly in the mitochondrial fraction (FIG. 5E). Phosphorylation of Drp1 at serine 616 (activating phosphorylation, p-Drp1$^{S616}$) promotes mitochondrial fission and cell death, whereas phosphorylation site serine 637 (inhibitory phosphorylation; p-Drp1$^{S637}$) inhibits mitochondrial fission. DOC-responsive LNCaP cells expressed higher levels of activating pDrp1$^{S616}$ than DOC-unresponsive E006AA, while E006AA expressed higher levels of inhibitory pDrp1$^{S637}$ than LNCaP cells (FIG. 5F). We further observed that p-Erk2, which phosphorylates Drp1 at S616, was upregulated in AA PCa, but the levels of p-Drp1$^{S616}$ phosphorylation in AA PCa cells was reduced. In contrast to AA PCa cells, the expression level of p-Drp1$^{S616}$ was higher, but p-Erk2 was not detected, in LNCaP cells (FIGS. 5F and G). These findings preclude the involvement of p-Erk2 in Drp1 phosphorylation at S616 in these cells. Reduced expression of p-AKT (FIG. 3F) with concomitant decrease of p-Drp$^{S616}$ (FIG. 5F) in AA PCa cells suggests that p-AKT may play a critical role in Drp1 phosphorylation at S616 in PCa cells. Inhibition of Drp1 phosphorylation at S616 by the AKT inhibitor, wortmanin, provided evidence that p-AKT contributes to the phosphorylation of Drp1 at S616 in PCa cells (FIG. 5H). We also confirmed the levels of pDrp1$^{S616}$ and pDrp1$^{S637}$ in MN and PT from AA and CA PCa patients, and observed that pDrp1$^{S616}$ was lower and pDrp1$^{S637}$ was higher in AA compared to CA patients (FIG. 14). Reduced accumulation of p-AKT in AA PCa cells suggests that either activation of AKT or inhibition of c-Myc and NF-κB may contribute to Drp1 phosphorylation at S616, which promotes CC release and sensitizes AA PCa cells to DOC. We observed that c-Myc or NF-κB inhibitor or AKT activator increased the levels of p-Drp1$^{S616}$ in AA PCa cells (FIG. 5I) that resulted in CC release in response to DOC treatment (FIGS. 5B-5D).

To define whether Drp1 phosphorylation plays a critical role in CC release and apoptosis induction, Drp1 in DOC-responsive LNCaP cells was silenced and treated with DOC (FIG. 5J). Drp1-silencing inhibited CC release, caspase-3 activation, PARP cleavage, and apoptosis in LNCaP cells (FIGS. 5K and L, and S8). To confirm that increased caspase-3 activation is mediated by Drp1 and CC, Drp1-silenced or CC-silenced AA PCa cells were treated with c-Myc or NF-κB inhibitor or AKT activator with or without DOC. The findings demonstrated that Drp1 and CC knock down greatly attenuated caspase-3 activation induced by either c-Myc/NF-κB inhibition or AKT activation with or without DOC treatment (FIG. 16). Taken together, these data showed that deficiency of Drp1 phosphorylation at S616 abrogated CC release and inhibited apoptosis in response to DOC in AA PCa cells.

CC-deficiency confers metabolic reprogramming in AA primary tumor and PCa cell lines: The physiological function of CC is to transport electrons from Complex III to Complex IV of OXPHOS system. Therefore, loss of CC may lead to metabolic reprogramming in AA PCa cells and AA PT tissues. OXPHOS subunits of Complexes I-V were reduced (FIG. 6A), whereas glycolytic enzymes and other glycolysis modulators were upregulated in AA PCa compared to CA PCa cells (FIG. 6B). Immunoblot analysis of MN and PT tissue samples from AA and CA men with PCa demonstrated that OXPHOS subunits of Complexes III, IV, and V were downregulated (FIG. 17), whereas lactate dehydrogenase A (LDHA) was upregulated, in AA PT compared to CA PT tissues (FIG. 18). Increased expression of LDHA mRNA in AA PCa cells and PT established that lack of CC caused the acquisition of a glycolytic phenotype in AA PCa cells and AA PT (FIGS. 6C and 6D). Higher glycolytic reserve capacity in AA PCa cells than CA PCa cells (FIG. 6E) suggested that AA PCa cells depend more on glycolysis than CA PCa cells for survival, resistance, and proliferation. Disruption of glycolysis via 3-bromopyruvate (3-BrPA) induced dose-dependent cell death in response to DOC in AA PCa cells (FIG. 6F).

If the glycolytic phenotype in AA PCa cells is due to lack of CC, restoration of CC by c-Myc/NF-κB inhibition, and AKT activation could block glycolytic phenotype in AA PCa cells. Treatment of AA PCa cells with c-Myc/NF-κB inhibitors or the AKT activator in the presence of DOC inhibited glycolytic reserve capacity in AA PCa cells compared to control or DOC alone (FIG. 6G). AKT activation alone inhibited glycolytic reserve in AA PCa cells, suggesting that AKT activation is sufficient to block aerobic glycolysis in AA PCa cells. MitoROS production in response to NF-κB inhibition or AKT activation alone or in combination with DOC further provides evidence that enhanced mitochondrial activity and sensitivity to DOC in AA PCa cells (FIG. 6H). To analyze the effect of CC expression on metabolic reprogramming, CC in LNCaP cells was knocked down and elevated expression of glycolytic proteins in these CA PCa cells was observed (FIG. 6I). Taken together, these data suggest that CC-deficiency and the glycolytic phenotype contribute to higher therapy resistance and aggressiveness in AA men with PCa.

Inhibition of c-Myc or NF-κB enhances therapeutic efficacy of DOC via CC upregulation, caspase-3 activation, and PARP cleavage in AA PCa xenograft tumors: To determine therapeutic efficacy of DOC upon inhibition of c-Myc/NF-κB, clonogenicity or colony forming ability (CFA) of AA and CA PCa cells were analyzed. Higher CFA in AA PCa cells was observed than in CA PCa cells (FIG. 7A). Exposure of DOC abolished CFA of CA PCa cells but not AA PCa (FIG. 7A). Either c-Myc/NF-κB inhibition or AKT activation with or without DOC reduced the CFA of AA PCa cells (FIG. 7B). These findings prompted the evaluation of the effect of c-Myc or NF-κB inhibition on efficacy of DOC in vivo using PCa xenografts. AA PCa E006AA hT xenografts in SCID mice were treated with c-Myc or NF-κB inhibitors with or without DOC twice weekly. Inhibition of either c-Myc or NF-κB alone induced CC expression in E006AA hT xenografts (FIG. 7C). In combination with DOC, the expression of CC was further upregulated leading to caspase-3 activation, and PARP cleavage in E006AA hT xenografts (FIGS. 7C and D). Taken together, these data clearly suggest that inhibition of c-Myc or NF-κB and DOC may be an effective therapeutic approach for the management of PCa in AA patients.

Discussion

This study provides the first comprehensive evidence that lack of CC plays a critical role in therapeutic resistance and development of aggressive disease among AA men with PCa. Patients with relapsed PCa after androgen deprivation therapy are treated often with taxane-based therapy, such as DOC. Lack of CC or reduced CC release is the driving force for apoptosome dysfunction leading to inhibition of apoptotic cell death, which may contribute to therapeutic resistance and recurrence upon treatment with chemotherapeutic agents, such as DOC. The findings using a variety of AA and CA PCa cell lines, and PT specimens suggest that CC-deficiency is the key reason for abrogated apoptosome formation/function in AA men with PCa. This notion is supported by the demonstration that exogenous addition of CC in purified cytosol activates caspases, suggesting that all required components except CC are active for apoptosome formation and function. Expression of endogenous CC using CRISPR-SAM technique induces caspase activation and cell death in AA PCa cells. Knockdown of CC in AA PCa cells inhibits caspase activation and cell death. Taken together, the findings provide evidence that lack of CC in PCa cells in AA men is a key reason for higher therapeutic resistance and faster relapse of advanced PCa. Apoptosis also can be executed by a caspase-independent mechanism, defects in permeabilization of the mitochondrial membrane preclude this possibility.

Apoptosome dysfunction could result from defects in permeabilization of the outer mitochondrial membrane because pharmacological restoration of CC in AA PCa is not sufficient to induce apoptosis. The findings establish that outer mitochondrial membrane permeabilization machinery is faulty in AA PCa cells due to increased accumulation of inactivating phosphorylation of Drp1 at serine637 residue (p-Drp1$^{S637}$) at mitochondria. Compelling evidence suggests that p-Drp1 S637 inhibits mitochondrial fragmentation and CC release, but other studies reveal that p-Drp1 S637 may also promote permeabilization of mitochondrial membrane in some types of cells. The data clearly indicate that accumulation of Drp1$^{S637}$ inhibits outer mitochondrial membrane permeabilization in AA PCa cells. In contrast to AA PCa cells, robust accumulation of activating phosphorylation of Drp1 at serine616 (p-Drp1$^{S616}$) was observed in CA PCa cells, which promotes outer mitochondrial permeabilization leading to CC release and caspase activation. Although phosphorylation of Drp1 at S616 is mediated by AMPK and Erk2 in other cell types, the study for the first time identifies that AKT, and not Erk2, is the key kinase responsible for Drp1 phosphorylation at S616 in PCa cells.

Another pathophysiological effect of CC loss in AA PCa cells and tumor tissues is the modulation of metabolic reprogramming and collapse of OXPHOS that causes acquisition of a glycolytic phenotype for energy requirement in AA PCa cells. Aerobic glycolysis confers selective advantage to cancer cells, such as AA PCa cells, and leads to inhibition of apoptotic cell death, increased proliferation, and the aggressive tumor phenotype. The findings provide evidence that lack of CC concomitantly associates with higher expression of various glycolytic proteins including LDHA, c-Myc, and NF-κB. These proteins are critical for possible reprogramming of mitochondrial metabolism and bioenergetics in AA PCa cells and AA tumor tissues, which promote survival, proliferation, and aggressiveness of AA PCa. Knockdown of CC expression in CA PCa cells leads to acquisition of glycolytic characteristics and mitochondrial dysfunction that causes CA PCa cells to adopt the AA PCa cell phenotype. These observations further support the conclusion that CC-deficiency is the cause of mitochondrial dysfunction in AA PCa.

It has been shown that AA PCa patients harbor dysfunctional mitochondria due to reduced mtDNA content (a marker for mitochondrial mass and function) compared to their CA counterparts. However, the underlying mechanisms for the occurrence of these characteristics remain uncertain. PGC1-ct and Nrf1, two major transcription factors, monitor mitochondrial mass and function by regulating the expression of mitochondrial proteins critical for mitochondrial biogenesis, such as mitochondrial transcription factor A (TFAM), OXPHOS complexes including CC, and other metabolism pathways like glutaminolysis. Thus, expressions of PGC1-ct and Nrf1 in PCa have been reported to correlate with favorable clinical outcome. The findings suggest that acquisition of mitochondrial dysfunction and development of therapy resistance is due to the abolished nuclear accumulation of Nrf1 that causes loss of CC in AA PCa tissues and AA PCa cells.

How is Nrf1 nuclear translocation inhibited in AA PCa cells? Proto-oncogenes c-Myc and NF-kB were upregulated in the nuclear compartment, whereas phosphorylated AKT was reduced in AA PCa cells compared to CA PCa cells. c-Myc, NF-kB, and AKT are key players that promote mitochondrial dysfunction and aerobic glycolysis in malignant cells, and observations confirm that c-Myc expression is increased in AA PT compared to CA PT tissues. If c-Myc and NF-kB contribute to acquisition of a glycolytic phenotype in AA PCa, inhibition of c-Myc and NF-kB should block Nrf1 nuclear translocation or transcriptional activity in AA PCa cells. Genetic and pharmacological inhibition of these two proteins induces Nrf1 nuclear translocation and its binding to the CC promoter, which ultimately leads to increased expression of CC. On the contrary, AKT signaling was suppressed in AA PCa cells compared to CA PCa cells and activation of AKT in AA PCa cells by inhibiting PTEN enhances Nrf1 activity and CC expression in AA PCa.

Increased expression of c-Myc in matched non-tumor prostate tissues in AA PCa patients may contribute to increased incidence of clinical PCa in AA compared to CA men. This notion is based on the understanding that c-Myc is a known promoter of prostate carcinogenesis and overexpression of human c-Myc in murine prostate leads to PCa development. Thus c-Myc overexpression may be an early alteration during prostate tumorigenesis among AA men. Overexpression of c-Myc induces oncogenic transformation in organoids generated from AA non-tumor prostate epithelial tissue, which further establishes the importance of c-Myc upregulation in PCa health disparity. Overall NF-kB expression was similar between AA and CA PCa cells, but increased NF-kB nuclear translocation was observed in AA PCa cells. Previous reports showed increased expression of NF-kB in AA PCa compared to CA PCa. NF-kB, a key promoter of inflammation, is a pre-requisite for PCa development and progression by regulating pro-growth cytokines and chemokines. Overexpression of c-Myc and NF-kB may serve as initiating events in prostate tumorigenesis, so loss-of-function mutation in tumor suppressor p53 and Rb1 or gain-of-function mutations in tumor promoters, such as Ras may contribute to higher incidence, greater acquisition of the aggressive phenotype, and enhanced resistance to therapy in AA compared to CA men.

This study provides the first comprehensive and mechanistic analysis of apoptosome and mitochondrial dysfunction, which contribute to therapeutic resistance and higher aggressiveness in AA compared to CA PCa patients. The key reason for apoptosome and mitochondrial dysfunction in AA PCa patients is the loss of CC in PT tissues. c-Myc and NF-kB-mediated suppression of Nrf1 pinpoint the loss of CC, and inhibition of c-Myc/NF-kB sensitizes AA PCa cells to DOC both in vitro and in vivo. Taken together, the findings conclude that loss of CC in AA PCa men is a hallmark event that is succeeded by mitochondrial and apoptosome dysfunction, which drives the development of therapeutic resistance an aggressive phenotype in AA men.

While embodiments of the present disclosure have been particularly shown and described with reference to certain examples and features, it will be understood by one skilled in the art that various changes in detail may be effected therein without departing from the spirit and scope of the present disclosure as defined by claims that can be supported by the written description and drawings. Further, where exemplary embodiments are described with reference to a certain number of elements it will be understood that the exemplary embodiments can be practiced utilizing either less than or more than the certain number of elements.

The citation of any publication is for its disclosure prior to the filing date and should not be construed as an admission that the present invention is not entitled to antedate such publication by virtue of prior invention.

What is claimed is:

1. A method of treating prostate cancer in a subject, said method comprising:

selecting a subject having prostate cancer and cytochrome c-deficiency in the cancer cells and/or cancer tissue including the mitochondria of the cancer cells and/or cancer tissue, and administering, to the selected subject, a therapeutically effective amount of one or more agents capable of directly restoring cytochrome-c activity, thereby sensitizing the prostate cancer cells or tissue to treatment with a taxane derived chemotherapeutic drug.

2. The method of claim 1, wherein the one or more agents that directly restore cytochrome-c activity include an agent that induces cytochrome-c expression.

3. The method of claim 2, wherein the agent that induces cytochrome-c expression is a c-Myc inhibitor.

4. The method of claim 2, wherein the agent that induces cytochrome-c expression is a NF-κB inhibitor.

5. The method of claim 2, wherein the agent that induces cytochrome-c expression is an Akt1 activator.

6. The method of claim 5, wherein the Akt1 activator is a PTEN inhibitor.

7. The method of claim 1, wherein the one or more agents that restore cytochrome-c activity include an agent that induces cytochrome-c release from mitochondria.

8. The method of claim 1 further comprising:

measuring expression or activity levels of c-Myc in a prostate cell sample from the selected subject, wherein the one or more agents capable of restoring cytochrome-c activity is selected based on said measuring.

9. The method of claim 1, wherein said one or more agents is administered in combination with a taxane derived chemotherapeutic drug.

10. The method of claim 9, wherein said chemotherapeutic agent is selected from the group consisting of docetaxel, cabazitaxel, mitoxantrone, and estramustine.

11. The method of claim 1, wherein said prostate cancer is a drug resistant form of prostate cancer.

12. The method of claim 1, wherein said prostate cancer is a recurrent form of prostate cancer.

13. The method of claim 1, wherein said selected subject is at risk of developing a drug resistant form of prostate cancer.

14. The method of claim 1, wherein the cytochrome c-deficiency is detected by measuring a glycolytic marker.

15. The method of claim 14, wherein the glycolytic marker is lactate dehydrogenase A (LDHA).

16. The method of claim 1, wherein said one or more agents is administered in combination with a chemotherapeutic agent that is selected from the group consisting of docetaxel, cabazitaxel, mitoxantrone, and estramustine and that is combined or administered with a glycolytic inhibitor.

17. The method of claim 16, wherein the glycolytic inhibitor is 3-bromopyruvate (3-BrPA).

18. The method of claim 1, wherein the cytochrome c-deficiency is a 60-70% decrease in cytochrome-c levels in the cancer cells or cancer tissue compared to non-deficient prostate cancer cells or cancer tissue.

19. The method of claim 18, wherein the decrease is measured by a densitometry analysis of at least one immunoblot of cytochrome-c.

20. A method of inducing apoptosis in drug resistant cancer cells, said method comprising:

selecting drug resistant cancer cells having cytochrome-c deficiency including in the mitochondria of the cancer cells and cancer tissue, and administering to the selected cells, one or more agents that restore cytochrome-c activity in an amount effective to sensitize said cancer cells to apoptosis by treatment with a taxane derived chemotherapeutic drug.

* * * * *

SEQUENCE LISTING

```
<160> NUMBER OF SEQ ID NOS: 20

<210> SEQ ID NO 1
<211> LENGTH: 50
<212> TYPE: PRT
<213> ORGANISM: Homo sapiens

<400> SEQUENCE: 1

Cys Ala Cys Cys Gly Cys Gly Thr Gly Cys Gly Thr Gly Cys Cys Cys
1               5                   10                  15

Thr Thr Cys Thr Thr Cys Thr Cys Gly Ala Ala Ala Cys Cys Gly Ala
            20                  25                  30

Gly Ala Ala Gly Ala Ala Gly Gly Gly Cys Ala Cys Gly Cys Ala Cys
        35                  40                  45

Gly Cys
    50


<210> SEQ ID NO 2
<211> LENGTH: 50
<212> TYPE: PRT
<213> ORGANISM: Homo sapiens

<400> SEQUENCE: 2

Cys Ala Cys Cys Gly Cys Thr Gly Ala Ala Ala Ala Ala Gly Gly Ala
1               5                   10                  15

Ala Gly Gly Ala Gly Thr Thr Gly Ala Ala Ala Ala Cys Thr Cys Ala
            20                  25                  30

Ala Cys Thr Cys Cys Thr Thr Cys Cys Thr Thr Thr Thr Thr Cys Ala
        35                  40                  45

Gly Cys
    50


<210> SEQ ID NO 3
<211> LENGTH: 25
<212> TYPE: DNA
<213> ORGANISM: Homo sapiens

<400> SEQUENCE: 3

tcacccacac tgtgcccatc tacga                                          25


<210> SEQ ID NO 4
<211> LENGTH: 25
<212> TYPE: DNA
<213> ORGANISM: Homo sapiens

<400> SEQUENCE: 4
```

cagcggaacc gctcattgcc aatgg 25

<210> SEQ ID NO 5
<211> LENGTH: 25
<212> TYPE: DNA
<213> ORGANISM: Homo sapiens

<400> SEQUENCE: 5
ccccacatta ggcttaaaaa cagat 25

<210> SEQ ID NO 6
<211> LENGTH: 23
<212> TYPE: DNA
<213> ORGANISM: Homo sapiens

<400> SEQUENCE: 6
tatacccccg gtcgtgtagc ggt 23

<210> SEQ ID NO 7
<211> LENGTH: 20
<212> TYPE: DNA
<213> ORGANISM: Homo sapiens

<400> SEQUENCE: 7
attagggcgt cttttcctgg 20

<210> SEQ ID NO 8
<211> LENGTH: 20
<212> TYPE: DNA
<213> ORGANISM: Homo sapiens

<400> SEQUENCE: 8
agcatgttag ggtgtacggc 20

<210> SEQ ID NO 9
<211> LENGTH: 25
<212> TYPE: DNA
<213> ORGANISM: Homo sapiens

<400> SEQUENCE: 9
tttggatcca atgggtgatg ttgag 25

<210> SEQ ID NO 10
<211> LENGTH: 30
<212> TYPE: DNA
<213> ORGANISM: Homo sapiens

<400> SEQUENCE: 10
tttgaattcc tcattagtag cttttttgag 30

<210> SEQ ID NO 11
<211> LENGTH: 20
<212> TYPE: DNA
<213> ORGANISM: Homo sapiens

<400> SEQUENCE: 11
ggagatccat catctctccc 20

<210> SEQ ID NO 12
<211> LENGTH: 20
<212> TYPE: DNA
<213> ORGANISM: Homo sapiens

<400> SEQUENCE: 12
ggcctgtgcc atcagtatct 20

<210> SEQ ID NO 13
<211> LENGTH: 25
<212> TYPE: DNA
<213> ORGANISM: Homo sapiens

<400> SEQUENCE: 13
tcacccacac tgtgcccatc tacga 25

<210> SEQ ID NO 14
<211> LENGTH: 25
<212> TYPE: DNA
<213> ORGANISM: Homo sapiens

<400> SEQUENCE: 14
cagcggaacc gctcattgcc aatgg 25

<210> SEQ ID NO 15
<211> LENGTH: 19
<212> TYPE: DNA
<213> ORGANISM: Homo sapiens

<400> SEQUENCE: 15
tataaattgc tttcaggcc 19

<210> SEQ ID NO 16
<211> LENGTH: 19
<212> TYPE: DNA
<213> ORGANISM: Homo sapiens

<400> SEQUENCE: 16
tacttcatca ggcatatgc 19

<210> SEQ ID NO 17
<211> LENGTH: 19
<212> TYPE: DNA
<213> ORGANISM: Homo sapiens

<400> SEQUENCE: 17
taatgagtcg ttcaataac 19

<210> SEQ ID NO 18
<211> LENGTH: 19
<212> TYPE: DNA
<213> ORGANISM: Homo sapiens

<400> SEQUENCE: 18
ttggtgtgaa gaaatttac 19

<210> SEQ ID NO 19
<211> LENGTH: 19
<212> TYPE: DNA
<213> ORGANISM: Homo sapiens

<400> SEQUENCE: 19
atctgagtca tcgtaagag 19

<210> SEQ ID NO 20
<211> LENGTH: 19
<212> TYPE: DNA
<213> ORGANISM: Homo sapiens -continued

<400> SEQUENCE: 20
tactatgtgt ggctgtggc 19